(12) United States Patent
Chou et al.

(10) Patent No.: US 9,216,178 B2
(45) Date of Patent: Dec. 22, 2015

(54) DRY BLEND FORMULATION OF TETRAHYDROBIOPTERIN

(71) Applicant: BioMarin Pharmaceutical Inc., Novato, CA (US)

(72) Inventors: Tianwei Chou, El Cerrito, CA (US); Augustus O. Okhamafe, Concord, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 13/666,697

(22) Filed: Nov. 1, 2012

(65) Prior Publication Data

US 2013/0108694 A1    May 2, 2013

Related U.S. Application Data

(60) Provisional application No. 61/554,665, filed on Nov. 2, 2011, provisional application No. 61/622,417, filed on Apr. 10, 2012.

(51) Int. Cl.
*A61K 31/519* (2006.01)
*A61K 9/48* (2006.01)
*A61P 7/06* (2006.01)
*A61K 9/14* (2006.01)

(52) U.S. Cl.
CPC ............... *A61K 31/519* (2013.01); *A61K 9/145* (2013.01); *A61K 9/4816* (2013.01)

(58) Field of Classification Search
CPC .... A61K 31/519; A61K 9/145; A61K 9/4816
USPC .......................................... 424/452; 514/249
See application file for complete search history.

(56) References Cited

U.S. PATENT DOCUMENTS

| | | |
|---|---|---|
| 2,541,717 A | 2/1951 | Petering |
| 2,568,685 A | 9/1951 | Petering et al. |
| 2,601,215 A | 6/1952 | Waller et al. |
| 2,603,643 A | 7/1952 | Kirchensteiner et al. |
| 2,955,110 A | 10/1960 | Patterson et al. |
| 3,505,329 A | 4/1970 | Weinstock |
| 4,252,822 A | 2/1981 | Berry et al. |
| 4,371,514 A | 2/1983 | Nagatsu et al. |
| 4,540,783 A | 9/1985 | Viscontini |
| 4,550,109 A | 10/1985 | Folkers et al. |
| 4,587,340 A | 5/1986 | Nichol et al. |
| 4,595,752 A | 6/1986 | Azuma et al. |
| 4,649,197 A | 3/1987 | Uchino et al. |
| 4,665,182 A | 5/1987 | Nichol et al. |
| 4,701,455 A | 10/1987 | Nichol et al. |
| 4,713,454 A | 12/1987 | Sakai et al. |
| 4,731,514 A | 3/1988 | Naotake et al. |
| 4,752,573 A | 6/1988 | Ziegler et al. |
| 4,758,571 A | 7/1988 | Curtius et al. |
| 4,774,244 A | 9/1988 | Curtius et al. |
| 4,778,794 A | 10/1988 | Naruse et al. |
| 4,920,122 A | 4/1990 | Naruse et al. |
| 4,937,342 A | 6/1990 | Kurono et al. |
| 4,943,575 A | 7/1990 | Cremer |
| 5,037,981 A | 8/1991 | Kurono et al. |
| 5,043,446 A | 8/1991 | Kikuchi et al. |
| 5,198,469 A | 3/1993 | Sakata |
| 5,198,547 A | 3/1993 | Bailey et al. |
| 5,350,851 A | 9/1994 | Bailey et al. |
| 5,401,844 A | 3/1995 | Ayling et al. |
| 5,418,192 A | 5/1995 | Borden et al. |
| 5,439,799 A | 8/1995 | Rautenberg et al. |
| 5,449,688 A | 9/1995 | Wahl et al. |
| 5,468,630 A | 11/1995 | Billiar et al. |
| 5,468,772 A | 11/1995 | Xu et al. |
| 5,502,050 A | 3/1996 | Gross |
| 5,554,647 A | 9/1996 | Perricone |
| 5,606,020 A | 2/1997 | Watanabe et al. |
| 5,643,586 A | 7/1997 | Perricone |
| 5,658,565 A | 8/1997 | Billiar et al. |
| 5,698,408 A | 12/1997 | Rokos |
| 5,744,340 A | 4/1998 | Fossetta et al. |
| 5,753,656 A | 5/1998 | Sakai et al. |
| 5,763,392 A | 6/1998 | Hansen et al. |
| 5,830,461 A | 11/1998 | Billiar et al. |
| 5,846,775 A | 12/1998 | Hillman et al. |
| 5,856,158 A | 1/1999 | Rosazza et al. |
| 5,874,433 A | 2/1999 | Gross |
| 5,877,176 A | 3/1999 | Gross |
| 5,879,690 A | 3/1999 | Perricone |
| 5,880,124 A | 3/1999 | Gross |

(Continued)

FOREIGN PATENT DOCUMENTS

| CH | 500999 A | 12/1970 |
|---|---|---|
| EP | 0349204 | 6/1989 |

(Continued)

OTHER PUBLICATIONS

Aqeel et al., "Response of 6-pyruvoyl-tetrahydrobiopterin synthase deficiency to tetrahydrobiopterin," *J. Child Neurology* 1992, 7, S26-S30.

(Continued)

*Primary Examiner* — Janet Epps-Smith
*Assistant Examiner* — Courtney Brown
(74) *Attorney, Agent, or Firm* — Jones Day

(57) ABSTRACT

Dry blend powder formulations comprising a pharmaceutical formulation containing tetrahydrobiopterin, and methods of making and using the same, are disclosed herein.

4 Claims, 9 Drawing Sheets

(56) References Cited

U.S. PATENT DOCUMENTS

| | | | |
|---|---|---|---|
| 5,882,908 A | 3/1999 | Billiar et al. | |
| 5,902,810 A | 5/1999 | Pfleiderer et al. | |
| 5,922,713 A | 7/1999 | Werner | |
| 5,932,208 A | 8/1999 | Chedid et al. | |
| 5,945,452 A | 8/1999 | Cooker et al. | |
| 6,011,040 A | 1/2000 | Muller | |
| 6,022,879 A | 2/2000 | Crow et al. | |
| 6,046,010 A | 4/2000 | Anderson | |
| 6,103,230 A | 8/2000 | Billiar et al. | |
| 6,117,872 A | 9/2000 | Maxwell et al. | |
| 6,153,615 A | 11/2000 | Gross | |
| 6,162,806 A | 12/2000 | Arai et al. | |
| 6,162,914 A | 12/2000 | Toderi et al. | |
| 6,177,280 B1 | 1/2001 | Yan et al. | |
| 6,180,597 B1 | 1/2001 | Liao | |
| 6,200,758 B1 | 3/2001 | Richardson | |
| 6,245,776 B1 | 6/2001 | Skwierczynski et al. | |
| 6,251,953 B1 | 6/2001 | Baranowitz | |
| 6,274,581 B1 | 8/2001 | Gross | |
| 6,288,067 B1 | 9/2001 | Okamura et al. | |
| 6,288,535 B1 | 9/2001 | Chass | |
| 6,319,905 B1 | 11/2001 | Mandel et al. | |
| 6,346,519 B1 | 2/2002 | Petrus | |
| 6,410,535 B1 | 6/2002 | Kashiwagi et al. | |
| 6,417,205 B1 | 7/2002 | Cooke et al. | |
| 6,423,751 B1 | 7/2002 | Liao | |
| 6,428,990 B1 | 8/2002 | Mukerji et al. | |
| 6,441,038 B1 | 8/2002 | Loder et al. | |
| 6,486,168 B1 | 11/2002 | Skwierczynski et al. | |
| 6,500,857 B1 | 12/2002 | Perricone | |
| 6,537,992 B2 | 3/2003 | Parker | |
| 6,544,994 B2 | 4/2003 | Rabelink et al. | |
| 6,562,969 B1 | 5/2003 | Robertus et al. | |
| 6,576,105 B1 | 6/2003 | Ma | |
| 6,617,359 B2 | 9/2003 | Wohlfart et al. | |
| 6,649,345 B2 | 11/2003 | Richardson | |
| 6,656,925 B2 | 12/2003 | Petrus | |
| 6,660,831 B2 | 12/2003 | Fallon | |
| 6,689,385 B2 | 2/2004 | Richardson et al. | |
| 6,693,094 B2 | 2/2004 | Pearson et al. | |
| 6,696,480 B2 | 2/2004 | Liao | |
| 6,706,728 B2 | 3/2004 | Hedenstrom et al. | |
| 6,749,875 B2 | 6/2004 | Selleck | |
| 6,784,178 B2 | 8/2004 | Gross et al. | |
| 6,995,158 B2 | 2/2006 | Rabelink et al. | |
| 7,566,462 B2 | 7/2009 | Jungles et al. | |
| 7,727,987 B2 | 6/2010 | Moser et al. | |
| 8,003,126 B2 | 8/2011 | Jungles et al. | |
| 2002/0037284 A1 | 3/2002 | Fallon | |
| 2002/0052374 A1 | 5/2002 | Rabelink et al. | |
| 2002/0058674 A1 | 5/2002 | Hedenstrom et al. | |
| 2002/0061862 A1 | 5/2002 | Billiar et al. | |
| 2002/0076782 A1 | 6/2002 | Rosazza et al. | |
| 2002/0082261 A1 | 6/2002 | Kashiwagi et al. | |
| 2002/0106645 A1 | 8/2002 | Richardson | |
| 2002/0119952 A1 | 8/2002 | Petrus | |
| 2002/0155445 A1 | 10/2002 | Jarvik | |
| 2002/0187958 A1 | 12/2002 | Horrobin et al. | |
| 2003/0004125 A1 | 1/2003 | Hirst et al. | |
| 2003/0032616 A1 | 2/2003 | Moskowitz et al. | |
| 2003/0045543 A1 | 3/2003 | Hedenstrom et al. | |
| 2003/0077335 A1 | 4/2003 | Richardson et al. | |
| 2003/0078231 A1 | 4/2003 | Wilburn | |
| 2003/0124524 A1 | 7/2003 | Kornman et al. | |
| 2003/0212135 A1 | 11/2003 | Gross et al. | |
| 2003/0216400 A1 | 11/2003 | Rabelink et al. | |
| 2003/0232835 A1 | 12/2003 | Ishihara et al. | |
| 2004/0002129 A1 | 1/2004 | Hennies et al. | |
| 2004/0014167 A1 | 1/2004 | Yabuta et al. | |
| 2004/0034030 A1 | 2/2004 | Richardson et al. | |
| 2004/0043064 A1 | 3/2004 | Iorio et al. | |
| 2004/0058896 A1 | 3/2004 | Dietrich et al. | |
| 2004/0077859 A1 | 4/2004 | Albert Waer et al. | |
| 2004/0115182 A1 | 6/2004 | Fallon | |
| 2004/0162269 A1 | 8/2004 | Petrus | |
| 2005/0137141 A1 | 6/2005 | Hilfinger | |
| 2005/0239807 A1 | 10/2005 | Stamler et al. | |
| 2006/0035900 A1 | 2/2006 | Moser et al. | |
| 2006/0040946 A1* | 2/2006 | Oppenheimer et al. | 514/249 |
| 2006/0194808 A1 | 8/2006 | Richardson et al. | |
| 2006/0211701 A1 | 9/2006 | Muntau-Heger et al. | |
| 2007/0167353 A1 | 7/2007 | Hilfinger et al. | |
| 2007/0270581 A1 | 11/2007 | Jungles et al. | |
| 2008/0075666 A1 | 3/2008 | Dudley et al. | |
| 2008/0090832 A1 | 4/2008 | Oppenheimer et al. | |
| 2008/0146577 A1 | 6/2008 | Matalon et al. | |
| 2008/0207624 A1 | 8/2008 | Sugita et al. | |
| 2008/0213239 A1 | 9/2008 | Morris | |
| 2010/0009997 A1* | 1/2010 | Oppenheimer et al. | 514/249 |
| 2010/0111918 A1* | 5/2010 | Oppenheimer et al. | 424/94.1 |
| 2011/0281880 A1* | 11/2011 | Oppenheimer et al. | 514/249 |

FOREIGN PATENT DOCUMENTS

| | | |
|---|---|---|
| EP | 0488078 | 6/1992 |
| EP | 0722731 | 7/1996 |
| EP | 0906913 | 4/1999 |
| EP | 0908182 | 4/1999 |
| EP | 0983765 | 3/2000 |
| EP | 1314782 | 5/2003 |
| EP | 1757293 | 5/2005 |
| EP | 1964566 | 12/2005 |
| JP | 59021685 | 2/1984 |
| JP | 05009065 | 5/1984 |
| JP | 60204786 | 10/1985 |
| JP | 63063613 | 3/1988 |
| JP | 63267781 | 11/1988 |
| JP | 4082888 | 3/1992 |
| JP | 9157270 | 6/1997 |
| WO | WO 95/13075 | 5/1995 |
| WO | WO 95/28377 | 10/1995 |
| WO | WO 97/44029 | 11/1997 |
| WO | WO 98/08516 | 3/1998 |
| WO | WO 99/43325 | 9/1999 |
| WO | WO 99/47153 | 9/1999 |
| WO | WO 00/03746 | 1/2000 |
| WO | WO 00/37653 | 6/2000 |
| WO | WO 00/56403 | 9/2000 |
| WO | WO 01/56551 | 8/2001 |
| WO | WO 02/17898 | 3/2002 |
| WO | WO 03/072096 | 9/2003 |
| WO | WO 03/077837 | 9/2003 |
| WO | WO 03/080063 | 10/2003 |
| WO | WO 03/084388 | 10/2003 |
| WO | WO 2004/002404 | 1/2004 |
| WO | WO 2004/016764 | 2/2004 |
| WO | WO 2004/017955 | 3/2004 |
| WO | WO 2004/041169 | 5/2004 |
| WO | WO 2004/044602 | 5/2004 |
| WO | WO 2004/058268 | 7/2004 |
| WO | WO 2005/049000 | 6/2005 |
| WO | WO 2005/049614 | 6/2005 |
| WO | WO 2005/065018 | 7/2005 |
| WO | WO 2005/107759 | 11/2005 |
| WO | WO 2006/055511 | 5/2006 |
| WO | WO 2006/063215 | 6/2006 |
| WO | WO 2006/112495 | 10/2006 |
| WO | WO 2006/118322 | 11/2006 |
| WO | WO 2007/007291 | 1/2007 |
| WO | WO 2007/067570 | 6/2007 |

OTHER PUBLICATIONS

Arnold, Phenylketonuria, eMedicine from webMD, Jun. 5, 2006, http://www.emedine.com/PED/topic1787.htm pp. 1-8.

Belanger-Quintana et al., "Spanish BH4-responsive phenylalanine hydroxylase deficient patients: Evolution of seven patients on long-term treatment with tetrahydrobiopterin," *Mol. Genet. Metab.* 2005, 86, S61-S66.

Berneggar et al., "High frequency of tetrahydrobiopterin-responsiveness among hyperphenylalaninemias: a study of 1,919 patients observed from 1988 to 2002," *Mol. Genet. Metabol.* 2002, 77, 304-313.

(56) References Cited

OTHER PUBLICATIONS

Bjelakovic et al., "Biochemical functions and clinical importance of unconjugated pteridines," *Medicine and Biology* 2004, 11, 49-54.
Blau et al., 34th EMG Meeting, Zurich, CH, May 31-Jun. 2, 2002, proceedings published Oct. 2002.
Blau et al., "Disorders of phenylalanine and tetrahydrobiopterin metabolism" in *Physician's Guide to the Laboratory Diagnosis of Metabolic Diseases*, 2nd ed., Blau et al., eds., Heidelberg, Springer-Verlag, 2003. pp. 89-106.
Blau et al., "Disorders of tetrahydrobiopterinand related biogenic amines" in The *Metabolic and Molecular Bases of Inherited Disease*, 8th ed., Scriver et al., eds., New York, McGraw-Hill, 2001. pp. 1275-1776.
Blau et al., "Optimizing the use of sapropterin (BH4) in the management of phenylketonuria," *Mol. Genet. Metab.* 2009, 96,158-163.
Bonafe et al., "Treatable neurotransmitter deficiency in mild phenylketonuria," *Neurology* 2001, 57, 908-911.
Cerone et al., "Long-term follow-up of a patient with mild tetrahydrobiopterin-responsive phenylketonuria," *Mol. Genet. Metab.* 2004, 81, 137-139.
Chang et al., "A study on gelatin capsule brittleness: moisture tranfer between the capsule shell and its content," *J Pharm. Sci.* 1998, 87, 556-558.
Choi et al., "Tetrahydrobiopterin is released from and causes preferential death of catecholaminergic cells by oxidative stress," *Mol. Pharm.* 2000, 58, 633-640.
Cosentino et al., "Tetrahydrobiopterin and dysfunction of endothelial nitric oxide synthase in coronary arteries," *Circulation* 1995, 91, 139-144.
Christensen et al., "Development of a skin-based metabolic sink for phenylalanine by overexpression of phenylalanine hydroxylase and GTP cyclohydrolase in primary human keratinocytes," *Gene Therapy* 2000, 7, 1971-1978.
Christensen et al., "Comparison of epidermal keratinocytes and dermal fibroblasts as potential target cells for somatic gene therapy of phenylketonuria," *Mol. Genet. Metabol.* 2002, 76, 313-318.
Curtius et al., "Therapeutic efficacy of tetrahydrobiopterin in Parkinson's disease," *Adv. Neurol.* 1984, 40, 463-466.
Curtius et al., "Successful treatment of depression with tetrahydrobiopterin," *Lancet* 1983, 1, 657-658.
Danfors et al., "Tetrahydrobiopterin in the treatment of children with autistic disorder: a double-blind placebo-controlled crossover study," *J. Clin. Psychopharmacol.* 2005, 25, 485-489.
Danks et al., "Variant forms of phenylketonuria," *Lancet* 1976, 1, 1236-1237.
Davis et al., "The auto-oxidation of tetrahydrobiopterin," *Eur. J. Biochem.* 1988, 173, 345-351.
De Vriese et al., "Endothelial dysfunction in diabetes," *Br. J. Pharm.* 2000, 130, 963-974.
De Vriese et al., "Mild to moderate hyperhomocysteinaemia in cardiovascular disease," *Acta Cardiol.* 1998, 53, 337-344.
Defily, "Control of microvascular resistance in physiological conditions and reperfusion," *J. Mol. Cell. Cardiol.* 1998, 30, 2547-2554.
Dhondt et al., "Atypical cases of phenylketonuria," *Eur. J. Pediatr.* 1987, 146, A38-A43.
Diiondt et al., "Diagnosis of variants of hyperphenylalaninemia by determination of pterins in urine," *Clin. Chim. Acta* 1981, 110, 205-214.
Dhondt et al., "Pterin metabolism in normal subjects and hyperphenylalaninaemic patients," *J. Inherit. Metab. Dis.* 1981, 4, 47-49.
Disorder index of the National Institute of Neurological Disorders and Stroke, http://www.nnhds.nih.gov/disorders/disorder_index.htm?css=print (inactive URL).
Dissing et al., "Tetrahydrobiopterin and Parkinson's disease," *Acta Neurol. Scand.* 1989, 79, 493-499.
Dudesek et al., "Molecular analysis and long-term follow-up of patients with different forms of 6-pyruvoyl-tetrahydropterin synthase deficiency," *Eur. J. Pediatr.* 2001, 160, 267-276.

Ellis, "The general concept of molecular chaperones," *Philos. Trans. R Soc. Lond. B. Biol. Sci.* 1993, 339, 257-261.
Elzaouk et al., "Dwarfism and low insulin-like growth factor-1 due to dopamine depletion in pts-1- mice rescued by feeding neurotransmitter precursor and H4-biopterin," *J. Biol. Chem.* 2003, 275, 28303-28311.
Endres et al., "Atypical phenylketonuria due to biopterin deficiency," *Helv. Paediat. Acta* 1982, 37, 489-498.
Erlandsen et al., "A structural hypothesis for BH4 responsiveness in patients with mild forms of hyperphenylalaninaemia and phenylketonuria," *J. Inherit. Metab.* 2001, 24, 213-230.
FDA Center for Drug Evaluation and Research (CDER) Draft Guidance for Industry ANDAs: Pharmaceutical Solid Polymorphism Chemistry, Manufacturing and Controls Information, Dec. 2004.
Fernell et al., "Possible effects of tetrahydrobiopterin treatment in six children with autism—clinical and positron emission tomography data: a pilot study.Dev. Med. & Child Neurology," *Dev. Med Child Neurol.* 1997, 39, 313-318.
Ferraris et al., "Essai de depistage indirect des deficits en tetrahydrobiopterine," *Pediatrie* 1987, 42, 549-555.
Fiege et al., "Plasma tetrahydrobiopterin and its pharmacokinetic following oral administration," *Mol. Genet. Metab.* 2004, 81, 45-51.
Frye et al., "Tetrahydrobiopterin as a novel therapeutic intervention for autism," *Neurotherapeutics,* 2010, 7, 241-249.
Furrer et al., "Trennung de diastereomeren (6R)- und (6S)-5,6,7,8-tetrahydro-L-biopterin," *Helv. Chim. Acta* 1979, 62, 2577-2580.
Galley et al., "Circulating tetrahydrobiopterin concentrations in patients with septic shock," *Brit. J. Anaesthesia* 2001, 86, 578-580.
Giugliani et al., "Successful therapy of hyperphenylalaninemia due to defective tetrahydrobiopterin metabolism in two siblings," *Rev. Brasil. Genet. IX* 1986, 4, 685-692.
Guttler et al., "Hyperphenylalaninemia: Diagnosis and classification of the various types of phenylalanine hydroxylase deficiency in childhood," *Acta Paediatrica Scandinavica Supplement* 1980, 280, 7-80.
Hajek et al., "Proton in vivo spectroscopy of patients with hyperphenylalaninaemia," *Neuropediatrics* 1993, 24, 111-112.
Hanley, "Tetrahydrobiopterin and mild phenylketonuria," *N. Engl. J. Med.* 2003, 348, 1722-1723.
Heitzer et al., "Tetrahydrobiopterin improves endothelium-dependent vasodilation by increasing nitric oxide activity in patients with Type II diabetes mellitus," *Circ. Res.* 2000, 43, 1435-1438.
Hennermann et al., "Partial and total tetrahydrobiopterin-responsiveness in classical and mild phenylketonuria (PKU)," *J. Inherit. Metab. Dis.* 2002, 25(Suppl. 1), 21.
Hennermann et al., "Long-term treatment with tetrahydrobiopterin increases phenylalanine tolerance in children with severe phenotype of phenylketonuria," *Mol. Genet. Metab.* 2005, 86, S86-S90.
Hsia et al., "Hyperphenylalaninemia," *Metab.* 1967, 16, 99-101.
Huether et al., "Individual carboxylic ester hydrolases of the developing cerebellum, influence of experimental hyperphenylalaninaemia," *Cell. Mol. Biol.* 1982, 28, 313-317.
Hyland et al., "Matters arising," *J. Neurol. Nurosurg. Psychiatry* 1987, 50, 242-243.
Katusic, "Vascular endothelial dysfunction: does tetrahydrobiopterin play a role?" *Am. J. Physiol. Heart Circ. Physiol.* 2001, 281, H981-H986.
Kaufman, "Hepatic phenylalanine hydroxylase and PKU," in Brian mechanisms in mental retardation: Proceeding of a conference in the series on mental retardation sponsored by the National Institute of Child Health and Human Development Mental Retardation Research Centers Series, NY, Academic Press, 1975, pp. 445-458.
Kaufman, "Phenylketonuria and its variants," *Ann. Clin. Lab. Sci.* 1977, 7, 178-185.
Kaufman, "Phenylketonuria due to a deficiency of dihydropterdine reductase," *N. Engl. J. Med.* 1975, 293, 785-790.
Kaufman, "Unsolved problems in diagnosis and therapy of hyperphenylalaninemia caused by defects in tetrahydrobiopterin metabolism," *J. Pediatr.* 1986, 109, 572-578.
Khripack et al., "Transformations of some substituted 5-benzyl-1,2,4-triazoline-3-thiones," *Chemistry of Heterocyclic Compounds (A Translation of Khimiya Geterotsiklicheskikh Soedinenli)* 1976, 740-742.

(56) References Cited

OTHER PUBLICATIONS

Koch et al., "Large neutral amino acid therapy and phenylketonuria: A promising approach to treatment," *Mol. Genet. Metab.* 2003, 79, 110-113.
Kredan et al., "Homocysteine-induced endothelial superoxide anion production is inhibited by tetrahydrobiopterin and folate," *Eur. Heart J.* 1999, 20, 41.
Kure et al., "Tetrahydrobiopterin-responsive phenylalanine hydroxylase deficiency," *J. Pediatr.* 1999, 135, 375-378.
KUVAN™ [sapropterin dihydrochloride (BH4)] Tablets Product Information, 2007, pp. 1-17.
Laffranchi et al., "Tetrahydrobiopterin synthesis precedes nitric oxide-dependent inhibition of insulin secretion in INS-1 rat pancreatic beta-cells," *Biochem. Biophys. Res. Commun.* 1997, 233, 66-70.
Lambruschini et al., "Clinical and nutritional evaluation of phenylketonuric patients on tetrahydrobiopterin monotherapy," *Mol. Genet. Metab.* 2005, 86, S54-S60.
Lang et al., "Homocysteine-induced endothelial superoxide anion production is inhibited by tetrahydrobiopterin and folate," *Circ.* 1999, 100, 411.
Lassker et al., "Tetrahydrobiopterin responsiveness in phenylketonuria," *J. Inherit. Metab. Dis.* 2002, 25, 65-70.
Leeming et al., "Relationship between plasma and red cell biopterins in acute and chronic hyperphenylalaninaemia," *J. Inherit. Metab. Dis.* 1990, 13, 883-887.
Levy et al., "Efficacy of sapropterin dihydrochloride (tetrahydrobiopterin 6R-BH4) for reduction of phenylalanine concentration in patients with phenylketonuria: A phase III randomised placebo-controlled study," *Lancet.* 2007, 370, 504-510.
Levy et al., "Recommendations for evaluation of responsiveness to tetrahydrobiopterin (BH4) in phenylketonuria and its use in treatment," *Mol. Genet. Metab.* 2007, 92, 287-291.
Linder et al., "Tetrahydrobiopterin responsiveness in phenylketonuria differs between patients with the same genotype," *Mol. Genet. Metab.* 2001, 73, 104-106.
Liu et al., "Study on a novel strategy to treatment of phenylketonuria," *Artif. Cells. Blood. Subs. and Immob. Biotech.*, 2002, 30, 243-257.
Lucke et al., "BH4-sensitive hyperphenylalaninemia: New case and review of literature," *Pediatric Neurology* 2003, 28, 228-230.
Lucock et al., "The impact of phenylketonuria on folate metabolism," *Mol. Genet. Metab.* 2002, 76, 305-312.
Mabry et al., "Phenylketonuria: Contemporary screening and diagnosis," *Ann. Clin. Lab. Sci.* 1990, 20, 392-397.
Maier et al., "Tetrahydrobiopterin improves endothelial function in patients with coronary artery disease," *J. Cardiovasc. Pharmacol.* 2000, 35, 173-178.
Mallolas et al., "Mutational spectrum of phenylalanine hydroxylase deficiency in the population resident of catalonia: Genotype-phenotype correlation," *Hum. Genet.* 1999, 105, 468-473.
Matalon et al., "Phenylketonuria: Screening, treatment and maternal PKU," *Clin. Biochem.* 1991, 24, 337-342.
Matsubara et al., "Improved diagnosis of classical vs. Atypical phenylketonuria by liquid chromatography," *Clin. Chem.* 1984, 30, 278-280.
Matsuura et al., "Highly stereoselective procedure for (6R)-tetrahydrobiopterin cofactor," *Chem. Lett. Jpn.* 1984, 52, 735-738.
Matsuura et al., "Hydrogenation of biopterin and its analogues; application for the convenient procedure of biopterin cofactor and related 5, 6, 7, 8-tetrahydropterins," *Heterocycles* 1985, 23, 3115-3120.
Matsuura et al. "Stereochemistry of biopterin cofactor and facile methods for the determination of the stereochemistry of a biologically active 5,6,7,8-tetrahydropterin," *J. Biochem.* 1985, 98, 1341-1348.
McCaman et al., "Fluorimetric method for the determination of phenylalanine in serum," *J. Lab. Clin. Med.* 1962, 59, 885-890.
Meininger et al., "Impaired nitric oxide production in coronary endothelial cells of the spontaneously diabetic BB rat is due to tetrahydrobiopterin deficiency," *Biochem. J.* 2000, 349, 353-356.
Milstein, "Interconversion of 6- and 7-substituted tetrahydropterins via enzyme-generated 4a-hydroxytetrahydropterin intermediates," *Meth. Enzymol.* 1997, 281, 116-123.
Missiou-Tsagaraki et al., "Phenylketonuria in Greece: 12 Years' experience," *J. Mental Deficiency Res.* 1988, 32, 271-287.
Mitchell et al., "Tetrahydrobiopterin-responsive phenylketonuria: the New South Wales experience," *Mol. Genet. Metab.* 2005, 86, S81-S85.
Mohyuddin et al., "Screening for biopterin defects among hyperphenylalaninemic patients: Report of a Canadian program after 3 years," *Chem. Biol. Pteridines* 1986, 243-246.
Muntau et al., "Tetrahydrobiopterin as an alternative treatment for Mils phenylketonuria," *N. Engl. J. Med.* 2002, 347, 2122-2132.
Niederwieser et al., "Atypical phenylketonuria with defective biopterin metabolism. Monotherapy with tetrahydrobiopterin or sepiapterin, screening and study of biosysthesis in man," *Eur. J. Pediatr.* 1982, 138, 110-112.
Niederwieser et al., "Peripheral tetrahydrobiopterin deficiency with hyperphenylalaninaemia due to incomplete 6-pyruvoyl tetrahydropterin synthase deficiency or heterozygosity," *Eur. J. Pediatr.* 1987, 146, 228-232.
Nixon et al., "Neopterin and biopterin levels in patients with atypical forms of phenylketonuria," *J. Neurochem.* 1980, 35, 898-904.
Nystrom et al., "Tetrahydrobiopterin increases insulin sensitivity in patients with type 2 diabetes and coronary heart disease," *Am. J. Physiol. Endocrinol. Metab.* 2004, 287, E919-E925.
O'Brien et al., "Counseling patients on drug-food interactions," *US Pharmacist* 1997, 22, 62-75.
Ogawa et al., "A case of 6-pyruvoyl-tetrahydropterin synthase deficiency demonstrates a more significant correlation to L-dopa dosage with serum prolactin levels than CSF homovanillic acid levels," *Brain Develop.* 2008, 30, 82-85.
Parker, "Diseases of phenylalanine metabolism," *Western J. Med.* 1979, 131, 285-297.
Patterson et al., "The synthesis of a pteridine required for the growth of crithidia fasciculata," *J. Am. Chem. Soc.* 1956, 78, 5868-5871.
PhenylAde Amino Acid Bars Brochure, Nov. 2002.
Pieper, "Acute amelioration of diabetic endothelial dysfunction with a derivative of the nitric oxide synthase cofactor, tetrahydrobiopterin," *J. Cardiovasc. Pharmacol.* 1997, 29, 8-15.
Ponzone et al., "Catalytic activity of tetrahydrobiopterin in dihydropteridine reductase deficiency and indications for treatment," *Pediatric Res.* 1993, 33, 125-128.
Ponzone et al., "Hyperphenylalaninemia and pterin metabolism in serum and erythrocytes," *Clin. Chem. Acta* 1993, 216, 63-71.
Ponzone et al., "Differential diagnosis of hyperphenylalaninaemia by a combined phenylalanine-tetrahydrobiopterin loading test," *Eur. J. Pediatr.* 1993, 152, 655-661.
Ponzone et al., "Tetrahydrobiopterin loading test in hyperphenylalaninemia," *Pediatric Res.* 1991, 30, 435-438.
Primrose, "Phenylketonuria with normal intelligence," *J. Ment. Deic. Res.* 1983, 27, 239-246.
Rabinoff, "Possible uses of urinary neopterin and biopterin measurement," *Med. Hypotheses* 1989, 29, 241-243.
Rey et al., "Kinetics of phenylalanine disappearance after intravenous load in phenylketonuria and its genetic variants," *Pediatr. Res.* 1979, 13, 21-25.
Roth, "Newborn metabolic screening: A search for "nature experiments,"" *Curr. Concepts Diagnosis* 1986, 79, 47-54.
Schaub et al., "Tetrahydrobiopterin therapy of atypical phenylketonuria due to defective dihydrobiopterin biosynthesis," *Arch. Dis. Child.* 1978, 53, 674-676.
Schlesinger et al., "Urinary dihydroxanthopterin in the diagnosis of malignant hyperphenylalaninemia and phenylketonuria," *Clin. Chim. Acta* 1979, 92, 187-195.
Schmidt et al., "The nitric oxide synthase cofactor tetrahydrobiopterine reduces allograft ischemia-reperfusion injury after lung transplantation," *J. Thorac. Cardiovasc. Surg.* 1999, 118, 726-732.
Schmidt et al., "Single dose oral tetrahydrobiopterin (BH4) leads to a prolonged increase in aortic BH4 levels in ApoE-KO mice," *Eur. J. Cardiovasc. Prev. Rehab.* 2007, 193, S4.

(56) References Cited

OTHER PUBLICATIONS

Schircks et al. "Über Pterinchemie. 60. vorläufige Mitteilung [1]. Eine neue, regiospezifische Synthese von L-Biopterin," *Helv. Chim. Acta* 1977, 60, 211.
Schulze et al., "Evaluation of 6-year application of the enzymatic colorimetric phenylalanine assay in the setting of neonatal screening for phenylketonuria," *Clin. Chim. Acta* 2002, 317, 27-37.
Scriver et al., "Hyperphenylalanine: Phenylalanine hydroxylase deficiency," *New York; McGraw-Hill*, 2001, pp. 1667-1724.
Scriver, "Science, medicine and phenylketonuria," *Acta Pardiatr.* 1994, 407, 11-18.
Seasiiore, "Tetrahydrobiopterin and dietary restriction in mild phenylketonuria," *N. Engl. J. Med.* 2002, 347, 2094-2095.
Sharma et al., "Development of a refractory stage in a dog model for phenylketonuria," *Res. Commun. Chem. Pathol. Pharmacol.* 1981, 33, 145-153.
Shaw et al., "Analytical methods in phenylketonuria clinical biochemistry," in Phenylketonuria and some other inborn errors of amino acid metabolism, Bickett et al., Eds., Stuggart; Georg. Theim Verlg, 47, 1969, pp. 47-56.
Shimizu et al., "Protective effects of tetrahydrobiopterin against nitric oxide-induced endothelial cell death," *Life Sci.* 1998, 63, 1585-1592.
Shimizu et al., "Role of tetrahydrobiopterin in the function of nitric oxide synthase, and its cytoprotective effect," *Int. J. Mol. Med.* 1998, 2, 533-540.
Shinozaki et al., "Abnormal biopterin metabolism is a major cause of impaired endothelium-dependent relaxation through nitric oxide/$O_2^-$ imbalance in insulin-resistant rat aorta," *Diabetes* 1999, 48, 2437-2445.
Shinozaki et al., "Oral administration of tetrahydrobiopterin prevents endothelial dysfunction and vascular oxidative stress in the aortas of insulin-resistant rats," *Circ. Res.* 2000, 87, 566-573.
Shintaku et al., "Tetrahydrobiopterin, responsive, hyperphenylalaninemia without biopterin deficiency," *Pteridines* 2000, 11, 83-84.
Shintaku et al., "Disorders of tetrahydrobiopterin metabolism and their treatment," *Curr. Drug Metab.* 2002, 3, 123-131.
Shintaku et al., "Long-term treatment and diagnosis of tetrahydrobiopterin-responsive hyperphenylalaninemia with a mutant phenylalanine hydroxylase gene," *Pediatric Res.* 2004, 55, 425-430.
Shintaku et al., "Plasma biopterin levels and tetrahydrobiopterin responsiveness," *Mol. Genet. Metab.* 2005, 86, S104-S106.
Slazyk et al., "Liquid-chromatographic measurement of biopterin and neopterin in serum and urine," *Clin. Chem.* 1990, 36, 1364-1368.
Smitii et al., "Neurological aspects of biopterin metabolism," *Arch. Dis. Child.* 1986, 61, 130-137.
Smith et al., "New variant of phenylketonuria with progressive neurological illness unresponsive to phenylalanine restriction," *Lancet* 1975, 1, 1108-1111.
Spaapen et al., "Tetrahydrobiopterin-responsive phenylalanine hydroxylase deficiency in Dutch neonates," *J. Inherit. Dis.* 2001, 24, 352-358.
Spaapen et al., "Tetrahydrobiopterin-responsive phenylalanine hydroxylase deficiency, state of the art," *Mol. Genet. Metab.* 2003, 78, 93-99.
Steinfeld et al., "Tetrahydrobiopterin monotherapy for phenylketonuria patients with common mild mutations," *Eur. J. Pediatr.* 2002, 161, 403-405.
Steinfeld et al., "A hypothesis on the biochemical mechanism of BH4-responsiveness in phenylalanine hydroxylase deficiency," *Amino Acids* 2003, 25, 63-68.
Sugimoto et al., "The convenient syntheses of biopterin and its three optical isomers," *Bull. Chem. Soc. Jpn.* 1975, 48, 3767-3768.
Sugimoto et al., "Studies on biologically active pteridines. I. The synthesis of 6-(1R)[and (1S)]-(1-hydroxyethyl)- and 6-(1S)[and (1R)]-(1,2-dihydroxyethyl)-2-amino-4-hydroxypteridines," *Bull. Chem. Soc. Jpn.* 1979, 52, 181-183.

Tada et al., "Follow-up study of a nationwide neonatal metabolic screening program in Japan," *Eur. J. Pediatr.* 1984, 145, 204-207.
Tanaka et al., "Hyperphenylalaninemia due to impaired dihydrobiopterin biosynthesis," *Eur. J. Pediatr.* 1981, 136, 275-280.
Tanaka et al., "Early initiation of L-dopa therapy enables stable development of executive function in tetrahydrobiopterin (BH4) deficiency," *Develop. Med. Child Neurology* 2007, 49, 372-376.
Taylor et al., "Pteridines. XXXVII. A total synthesis of L-erythro-biopterin and some related 6-(polyhydroxyalkyl)pterins," *J. Am. Chem. Soc.* 1976, 98, 2301-2307.
Thony et al., "Mutations in the pterin-4-α carbinolamine dehydratase (PCBD) gene cause a benign form of hyperphnylalaninemia," *Hunman Genet.* 1998, 103, 162-167.
Tiefenbacher et al., "Endothelial dysfunction of coronary resistance arteries is improved by tetrahydrobiopterin in atherosclerosis," *Circ.* 2000, 102, 2172-2179.
Toyosaki et al., "Antioxidant effect of riboflavin in aqueous solution," *J. Agric. Food Chem.,* 1989, 37, 286-289.
Treact et al., "Analysis of phenylalanine hydroxylase genotypes and hyperphenylalaninemia phenotypes using L-[1-$^{13}$C]phenylalanine oxidation rates in vivo: A pilot study," *Pediatr. Res.* 1997, 42, 430-435.
Trefz et al., "Successful treatment of phenylketonuria by tetrahydrobiopterin," *Eur. J Pediatr.* 2001, 160, 315.
Trefz et al., "Potential role of tetrahydrobiopterin in the treatment of maternal phenylketonuria," *Pediatrics* 2003, 112, 1566-1569.
Trefz et al., "Long-term treatment of patients with mild and classical phenylketonuria by tetrahydrobiopterin," *Mol. Genet. Metab.* 2005, 86, S75-S80.
Trefz et al., "Efficacy of sapropterin dihydrochloride in increasing phenylalanine tolerance in children with phenylketonuria: A phase III, randomized double-blind, placebo-controlled study," *J. Pediatr.* 2009, 154, 700-707.
Tsai et al., "Psychopharmacology in autism," *Psychosomatic Med.* 1999, 61, 651-665.
Vasquez-Vivar et al., "Superoxide generation by endothelial nitric oxide synthase: The influence of cofactors," *Proc. Natl. Acad. Sci. USA* 1998, 95, 9220-9225.
Verma et al., "Novel cardioprotective effects of tetrahydrobiopterin after anoxia and reoxygenation: Identifying cellular targets for pharmacologic manipulation," *J. Thoracic Cardiovasc. Surg.* 2002, 123, 1074-1083.
Villasana et al., "Neurologica deterioration in adult phenylketonuria," *J. Inherit. Metab. Dis.* 1989, 12, 451-457.
Viscontini et al. "Fluoreszierende Stoffe aus *Drosophila melanogaster*. 14. Mitteilung [1]. Eine Synthese des Biopterins," *Helv. Chim. Acta* 1969, 52, 1225-1228.
Wachtel, "Review of current practices in management of inherited disorders of amino acid metabolism in western Europe," *Human Nutr. Applied Nutr.* 1986, 40A, 61-69.
Walter et al., "Inhalation of the nitric oxide synthase cofactor tetrahydrobiopterin in healthy volunteers," *Am. J. Respir. Crit. Care Med.* 1997, 156, 2006-2010.
Weglage et al., "Tetrahydrobiopterin responsiveness in a large series of phenylketonuria patients," *J. Inherit. Metab. Dis.* 2002, 25, 321-322.
Wever et al., "Tetrahydrobiopterin regulates superoxide and nitric oxide generation by recombinant endothelial nitric oxide synthase," *Biochem. Biophys. Res. Commun.* 1997, 237, 340-344.
Whiteley et al., "An abbreviated synthesis of tetrahydropteridines," *Anal. Biochem.,* 1984, 137, 394-396.
Yoshioka et al., "Atypical phenylketonuria due to biopterin deficiency: Diagnosis by assay of an enzyme involved in the synthesis of sepiapterin from dihydroneopterin triphosphate," *Zoological Sci.* 1984, 1, 74-81.
Zurfluh et al., "Pharmacokinetics of orally administered tetrahydrobiopterin in patients with phenylalanine hydroxylase deficiency," *J. Inherit. Metab. Dis.* 2006, 29, 725-731.
Letter from FDA to BioMarin Pharmaceutical regarding IND application No. 69,708 for tetrahydrobiopterin, dated Sep. 27, 2004.
Letter from BioMarin Pharmaceutical to FDA in response to their comments in the Sep. 27, 2004 letter regarding IND application No. 69,708 for tetrahydrobiopterin, dated Oct. 19, 2004.

(56) References Cited

OTHER PUBLICATIONS

Office Action mailed Dec. 15, 2010, U.S. Appl. No. 10/563,418.
Office Action mailed Apr. 27, 2011, U.S. Appl. No. 10/563,418.
Notice of Allowance mailed Jun. 23, 2011, U.S. Appl. No. 10/563,418.
Office Action mailed Nov. 28, 2006, U.S. Appl. No. 10/990,316.
Office Action mailed Jun. 28, 2007, U.S. Appl. No. 10/990,316.
Office Action mailed Oct. 23, 2007, U.S. Appl. No. 10/990,316.
Office Action mailed Apr. 2, 2008, U.S. Appl. No. 10/990,316.
Office Action mailed Jul. 24, 2009, U.S. Appl. No. 10/990,316.
Notice of Allowance mailed Feb. 26, 2010, U.S. Appl. No. 10/990,316.
Office Action mailed Aug. 6, 2008, U.S. Appl. No. 12/106,621.
Office Action mailed Oct. 20, 2008, U.S. Appl. No. 12/106,621.
Interview Summary mailed Oct. 31, 2008, U.S. Appl. No. 12/106,621.
Notice of Allowance mailed Jun. 5, 2009, U.S. Appl. No. 12/106,621.
"Tetrahydrobiopterin tablets" by Schircks Laboratories, Aug. 15, 2003.
"Data Sheet—Tetrahydrobiopterin" by Schircks Laboratories, Sep. 16, 2003.
"Summary of product characteristics—Tetrahydropterin 10mg/50mg Tablets" by Schircks Laboratories, Jan. 7, 2004.
"Certificate of Analysis" by Schircks Laboratories, Mar. 11, 2005.
"Tetrahydrobiopterin tablets" by Schircks Laboratories, Jan. 8, 2008.
"Summary of product characteristics—Tetrahydrobiopterin tablets" by Schricks Laboratories, Mar. 31, 2008.
Bailey et al., "Separation and properties of the 6-diastereoisomers of L-erythro-tetrahydrobiopterin and their reactivities with phenylalanine hydroxylase," J. Biol. Chem. 1978, 253:1598.
Brenneman et al., "The role of tetrahydropteridines in the enzymatic conversion of tyrosine to 3,4-dihydroxyphenylalanine," Biochem. Biophys. Res. Commun. 1964, 17:177.
Curtius et al., "Atypical phenylketonuria due to tetrahydrobiopterin deficiency. Diagnosis and treatment with tetrahydrobiopterin, dihydrobiopterin and sepiapterin," Clin. Chim. Acta. 1979, 93:251.
Levine et al., "Tetrahydrobiopterin in striatum: localization in dopamine nerve terminals and role in catecholamine synthesis," Science 1981, 214:919.
Nagai et al., "Studies on sepiapterin reductase: Further characterization of the reaction product," Arch. Biochem. Biophys. 1968, 126:426.
Nagatsu et al., "Tyrosine hydroxylase. The initial step in norepinephrine biosynthesis," J. Biol. Chem. 1964, 239:2910.
Nagatsu et al., "Biopterin in human brain and urine from controls and parkinsonian patients: Application of a new radioimmunoassay," Clin. Chim. Acta 1981, 109:305.
Narabayashi et al., "Tetrahydrobiopterin administration for Parkinsonian symptoms," Proc. Jpn. Acad. Ser. B 1982, 283:58.
Niederwieser et al., "Atypical phenylketonuria caused by 7,8-dihydrobiopterin synthetase deficiency," Lancet 1979, 313:131.
Watanabe et al., "Structure and thermostability of tRNA," Seikagaku 1981, 53:1033.
European Medicines Agency Evaluation of Medicines for Human Use, "CHPM Assessment Report for Kuvan," 2008.

\* cited by examiner

Appearance of HPMC capsule content after 6 months storage at 40 °C/5% RH

DRY BLEND FORMULATION OF TETRAHYDROBIOPTERIN

CROSS REFERENCE TO RELATED APPLICATIONS

This application claims the benefit of the priority of U.S. Provisional Application Nos. 61/554,665, filed Nov. 2, 2011; and 61/622,417, filed Apr. 10, 2012; the disclosure of each of which is incorporated herein by reference in its entirety.

BACKGROUND OF THE DISCLOSURE

1. Field of the Disclosure

This disclosure is generally directed to dry blend, powder formulations and dosage forms of tetrahydrobiopterin. In particular, provided is a dry blending process for tetrahydrobiopterin (i.e., BH4 dihydrochloride), the powder of which can be stably packaged in sachets, stable capsule dosage forms containing a pullulan-free capsule shell, or dissolved into a stable solution and stored in hermetically and non-hermetically sealed containers.

2. Background

Tetrahydrobiopterin (also referred to as BH4 or sapropterin) is a biogenic amine of the naturally occurring pterin family and is a cofactor for a number of different enzymes, including phenylalanine hydroxylase (PAH), tyrosine 3-hydroxylase, tryptophan 5-hydroxylase, and nitric oxide synthase (NOS). Accordingly, BH4 is involved in the synthesis of the amino acids phenylalanine, tyrosine and tryptophan, and the neurotransmitters dopamine and serotonin. Moreover, BH4 is essential for NOS-catalyzed oxidation of L-arginine to L-citrulline and nitric oxide. Pterins are present in physiological fluids and tissues in reduced and oxidized forms, but only the 5,6,7,8-tetrahydrobiopterin is biologically active. More specifically, it is the 6R enantiomer of BH4 that is known to be the biologically active enantiomer. For a detailed review of the synthesis of and disorders associated with BH4, see Blau et al., "Disorders of tetrahydrobiopterin and related biogenic amines" in C. R. Scriver et al., eds., The Metabolic and Molecular Bases of Inherited Disease, $8^{th}$ ed., pp. 1275-1776, McGraw-Hill (New York, 2001).

Tetrahydrobiopterin is unstable, readily undergoes aerobic oxidation at room temperature, and has a shelf-life of less than 8 hours at room temperature in aqueous solutions. Due to the instability of BH4, most tetrahydrobiopterin products available on the market need to be specially packaged or kept frozen. The instability of such BH4 compositions is undesirable, and significant degradation resulting from improper storage could hinder therapy of patients. One example of a stable BH4 tablet composition is disclosed in WO 2006/055511, which is incorporated herein by reference in its entirety. Such a tablet composition is sold under the tradename KUVAN®. There is a need for additional formulations of BH4 suitable for pharmaceutical use.

SUMMARY

Provided herein is a stable dry blend formulation of tetrahydrobiopterin (BH4) or a BH4-related compound, stable dosages in the form of capsule dosages or dry powder sachet dosages, and therapeutic methods using such dosage forms.

In one aspect of the disclosure, provided herein is a stable dry blend formation of BH4 or a BH4-related compound. In one embodiment, the formulation comprises a dry blend of BH4 or a BH4-related compound, a flavor enhancer, a sweetener, and one or more fillers wherein the components are blended together. In certain embodiments, the blending comprises blending the fillers with the BH4 or BH4 compound and flavor enhancer in a blender to achieve a adequate mixture, further blending a portion of the blended mixture with acesulfame potassium or sucralose, a flavoring agent, and ascorbic acid and thereafter passing that mixture through a suitable sieve, and lastly blending the second mixture with the remainder of the first mixture until the blend is homogenous.

In certain embodiments, the BH4 or a BH4-related compound is (6R)-L-erythro-5,6,7,8-tetrahydrobiopterin dihydrochloride (i.e., "BH4 dihydrochloride" or "sapropterin dihydrochloride").

In certain embodiments for example, the fillers are isomalt, lactitol, maltitol, mannitol, sorbitol, xylitol, sucrose, fructose, or combinations thereof.

In certain embodiments, for example, the dry blend formulation also contains a sweetener wherein the sweetener is acesulfame potassium, isomalt, Magna Sweet, maltitol, mannitol, sorbitol, sucralose, xylitol, alitmae, neohesperidin dihydrochalcone, trehalose, tagatose, neotame, saccharin and salts thereof, stevioside, erythritol, isomaltulose, polydextrose, luo han guo, monatin, cyclamate, osladine, sucrose, fructose, or glucose or combinations thereof.

In certain embodiments, for example, the flavor enhancer is anhydrous citric acid, citric acid monohydrate, malic acid, tartic acid, sodium citrate, potassium citrate monohydrate, potassium citrate anhydrous, or sodium potassium tartate, ascorbic acid, sodium ascorbate, or combinations thereof.

In certain embodiments, for example, the flavoring agent is a cherry, grape, orange, pink lemonade, raspberry, grape, lemon, orange, strawberry, tutti-frutti, tangerine, apple, watermelon, pineapple, banana, peach, kiwi, mango, mixed berry, raspberry lemonade, wild blackberry, blue raspberry, citrus, blueberry, lime, lemon lime, grapefruit, pomegranate, pear, or plum flavors, bubble gum, or combinations thereof.

In certain embodiments, for example, the sieve is a 20 mesh sieve.

In another embodiment, the dry blend formulation is dissolved in an aqueous solution, flushed with an inert gas, and hermetically sealed wherein the active solution remains stable.

In another aspect of the disclosure, stable BH4 or BH4-related compounds can optionally include one or more other therapeutic agents suitable for the condition to be treated. In one embodiment, the other therapeutic agents are selected from folates, including but not limited to folate precursors, folic acids, and folate derivatives, e.g., folinic acid (leucovorin); vitamins, such as vitamin C (ascorbic acid), vitamin B2 (riboflavin), and vitamin B12; neurotransmitter precursors, such as L-dopa, carbidopa, and serotonin; 5-hydroxytryptophan; arginine; and combinations thereof.

In another aspect of the disclosure, provided herein are therapeutic methods using the stable dosage forms described herein. The stable dosage forms are useful for treating, ameliorating, or preventing any BH4-responsive conditions or disorders, e.g., metabolic disorders involving amino acid metabolism. In one embodiment, the stable dosage forms are used to treat subjects exhibiting elevated phenylalanine levels or decreased tyrosine levels, e.g., subjects suffering from hyperphenylalanemia, mild phenylketonuria (PKU), or classic severe PKU. In another embodiment, the stable dosages are used to treat subjects suffering from conditions or disorders that would benefit from enhancement of nitric oxide synthase activity, including, but not limited to, vascular diseases, ischemic or inflammatory diseases, diabetes, and insulin resistance. The total dose of BH4 or BH4-related compound required can be administered in multiple doses or in a single dose. The dosage forms can be administered daily or at some other interval, e.g., every alternative day or weekly.

In another aspect of the disclosure, the stable dosage forms can be used for treating or ameliorating autism. In one embodiment, the BH4 or BH4-related compound can be used for treating or ameliorating autism in children. In one embodiment, the BH4 or BH4-related compound can be used for treating or ameliorating autism in adults. In a particular embodiment, the BH4 or BH4-related compound can be administered in conjunction with a second pharmaceutical composition to treat or ameliorate the symptoms of autism. In a particular embodiment, the second pharmaceutical compound for the combination treatment can be selected from groups consisting of stimulants, antidepressants, antianxiety medications, non-stimulant ADHD medications, antipsychotics, mood stabilizers, or Alzheimer's medications.

In another aspect of the disclosure, the stable dosage forms can be used alone or in conjunction with other therapies suitable for treating the particular condition or disorder, including the underlying disease or clinical symptoms thereof. For example, for treatment of PKU or BH4 deficiency, the dosage forms disclosed herein can be administered in combination with a protein-restricted diet, e.g., where the subject is limited to about 600 mg or less, or about 300 mg or less of protein daily, and the subject optionally is given supplements of amino acids, such as tyrosine, valine, tryptophan, isoleucine, and/or leucine. The dosage forms can also be administered in combination with folates, arginine, vitamins, or neurotransmitter precursors, or combinations thereof. As another example, for vascular diseases, diabetes, or insulin resistance, the dosage forms described herein can be administered in conjunction with other therapeutic agent(s), such as anti-hypertensive agents, anti-platelet agents, cholesterol-lowering agents, insulin, or oral hypoglycemic agents.

In another aspect of the disclosure, provided herein are stable capsule dosage forms, which comprise a pharmaceutical formulation containing BH4 or a BH4-related compound that maintains its stability for an extended period of time. In one embodiment, the formulation comprises a crystalline (e.g., powder) form of BH4 that is stable at room temperature for more than 8 hours, and a pharmaceutically acceptable carrier, diluent, or excipient. In certain embodiments, the stable capsules provided herein, in which BH4 exhibits unexpected stability, have a projected shelf-life of at least 2 years at room temperature. In another embodiment, the formulation comprises at least about 40% of BH4 or a BH4-related compound by weight of the formulation.

In a further embodiment, the stable capsule dosage forms comprise a pharmaceutical formulation containing BH4 or a BH4-related compound and one or more pharmaceutically acceptable excipients. In one embodiment, the excipients are selected from binders, fillers, diluents, disintegrants, glidants, acidic antioxidants, lubricants, and combinations thereof. In certain embodiments, the formulation includes mannitol, crospovidone, ascorbic acid, sodium stearyl fumarate, and silicon dioxide. In another embodiment, the formulation contains microcrystalline cellulose.

In another embodiment, the stable capsule dosage forms are stored without desiccant wherein the BH4 or BH4-related compound remains active within the stable capsules in the absence of desiccant.

In another aspect of the disclosure, provided herein are stable sachet dosage forms, which comprise a pharmaceutical formulation containing BH4 or a BH4-related compound that maintains its stability for an extended period of time. Sachet, for example, refers to a small bag or packet wherein the small bag or packet contains the BH4 or BH4-related compound dosage. Sachets are well known in the art and one of ordinary skill will understand the full breadth of the term.

In one embodiment, the sachet is a single chamber sachet. In another embodiment, the sachet is a double stick/dual chamber sachet wherein the dual chamber stick pack separates incompatible powder components (e.g., Twin Stick Dual Chamber Stick Pack Design from Packing Technologies and Inspection, LLC). In another embodiment, one chamber contains the active BH4 or a BH4-related compound dry blend and the other contains the dry flavor blend. In another embodiment, the powders from both chambers can be mixed and diluted with a liquid prior to oral ingestion.

In another embodiment, the BH4 or BH4-related compound dry powder blend is dissolved in an aqueous solution prior to ingestion. In a specific embodiment, the dry blend powder is clear when dissolved (i.e., the solution is not cloudy).

In another embodiment, the dual chamber sachet is packaged in foil pouches. In another embodiment the BH4 or BH4-related compound is stable for at least 3 months at room temperature. In another embodiment, the projected shelf-life is at least 2 years at room temperature.

In further embodiments, the dual chamber sachets comprise a pharmaceutical formulation containing BH4 or a BH4-related compound and one or more pharmaceutically acceptable excipients. In one embodiment, the excipients are selected from flavor enhancers, flavoring agents, sweeteners, fillers, diluents, glidants, anti-oxidants, and combinations thereof. In one specific embodiment, the excipients can improve stability and manufacturability of the dry blend. In other embodiments, the fillers may be selected from the non-exclusive list consisting of, for example, isomalt, lactitol, maltitol, mannitol, sorbitol, xylitol, sucrose, and fructose. For the compositions and methods described herein, particular features of the disclosure, such as components, ranges thereof, in compositions, conditions and steps, can be selected from the various embodiments and examples described herein.

In another embodiment, such methods involve administering BH4, whether swallowed as a solid or semisolid dosage form, or dissolved in a liquid, with food, e.g., a high-fat food or a high-fat and/or high-calorie meal. In another embodiment, BH4, whether swallowed or dissolved, is administered at a specified time including but not limited to morning, day, night, same time of the day, with food, e.g., a high-fat food or a high-fat and/or high-calorie meal, one or more times a day. In another embodiment, BH4 is ingested once daily as a solid dosage form just after meals. In another embodiment the solid dosage form is a formulated tablet or capsule. In more exemplary embodiments, BH4 is ingested within approximately 0 to 30 minutes, or 5 to 20 minutes, of eating a meal.

Other features and advantages of the disclosure will become apparent from the following detailed description. It should be understood, however, that the detailed description and the specific examples, while indicating particular embodiments of the disclosure, are given by way of illustration only, and various changes and modifications within the spirit and scope of the disclosure will become apparent to those skilled in the art from the detailed description.

DETAILED DESCRIPTION

Figure 1:
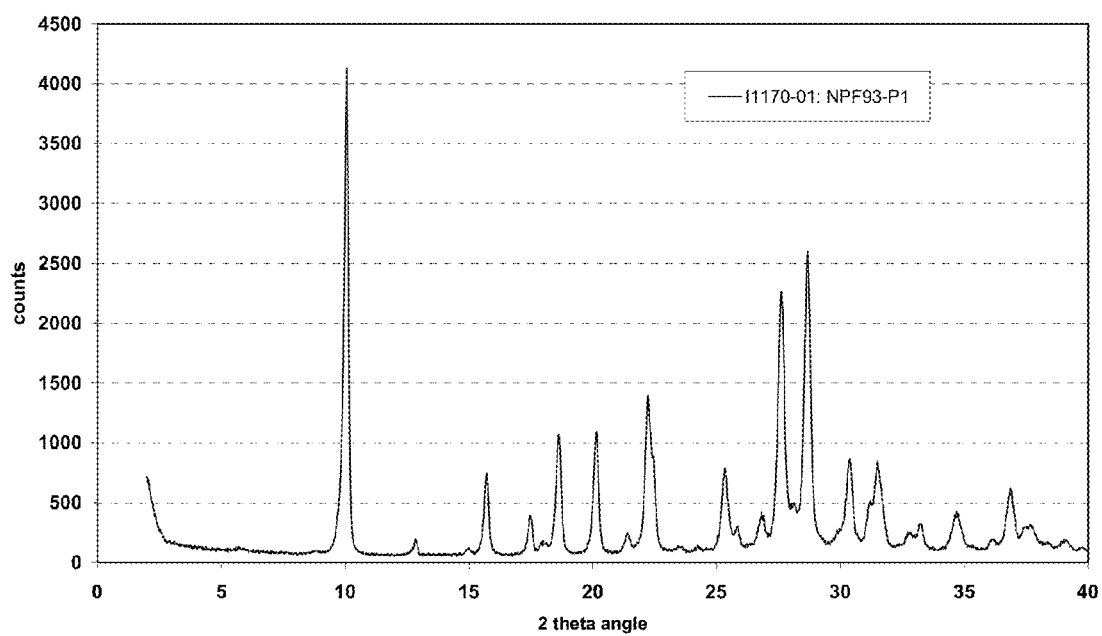
FIG. 1 is a graph of the characteristic X-ray diffraction pattern exhibited by polymorphic form B of (6R)-L-erythro-tetrahydrobiopterin dihydrochloride.

A first aspect of the disclosure is a stable, dry blend formulation of BH4 or a BH4-related compound. In one embodiment, the stable dry blend formulation is achieved by mixing a BH4 or BH4-related compound with a filler, flavoring agent, and flavor enhancer in a blender and passed through a sieve. In certain embodiments, a filler, a BH4 or BH4-related compound, and flavoring agent is blended together first, thereafter a portion of the mixture is further blended with acesulfame potassium or sucralose, a flavoring agent, and ascorbic acid, then passed through a suitable sieve, mixed with the remaining portion of the initial blend, and then blended until the mixture is homogenous.

Another aspect of the disclosure are stable dosage forms that maintain the stability of a hygroscopic, moisture-sensitive active ingredient over time. In one embodiment, the active BH4 or a BH4-related compound is in the form of an anhydrous polymorph of (6R)-L-erythro-5,6,7,8-tetrahydrobiopterin dihydrochloride (i.e., "BH4 dihydrochloride" or "sapropterin dihydrochloride") that is stable at room temperature to atmospheric oxygen and normal humidity, described herein as polymorph B. Under certain conditions in which moisture is present (e.g., percent relative humidity above about 80% or a moisture-containing dosage form), polymorph B begins to absorb water, and thereby loses its crystalline form (i.e., becomes amorphous) and becomes labile to oxidation. BH4 dihydrochloride is hygroscopic. Following moisture absorption or dissolution in the presence of water, BH4 dihydrochloride becomes labile to oxidation. The main oxidative degradation product of BH4 is dihydrobiopterin (BH2), which in turn gets oxidized to biopterin.

Another aspect of the disclosure are stable dosage forms made from dry blending wherein the dry blending does not expose the active BH4 or BH4-related compound to moisture. Compared to wet blending formulations which can degrade the stable crystalline polymorph B formulation, dry blending can result in less degradation. Furthermore, the active pharmaceutical ingredient, i.e., the BH4 or BH4-related compound, of the dry blend powder retains its crystalline form throughout the dry blending process, in contrast to state changes resulting from a wet blending process.

Tetrahydrobiopterin dihydrochloride would be expected to exhibit decreased stability if formulated in capsules. However, conventional capsule shells contain some amount of water. For example, capsule shells made of gelatin typically contain around 10 weight % water, and capsule shells made of hydroxypropyl methylcellulose (HPMC) typically contain about 4 to 6 weight % water. Gelatin capsules are expected to transfer moisture from the capsule shell to the formulation loaded into the capsule, particularly if the formulation contains a hygroscopic ingredient (see, e.g., R. Chang et al., *J. Pharm. Sci.*, 87: 556-558 (1998)). The loss of water from the capsule shell can cause the gelatin capsules to become brittle and fracture easily (Chang et al., id.). More importantly, US 2004/0043064 teaches that the moisture transmitted from the gelatin capsule shell to the formulation "result[s] in any number of problems, including degradation" of the active ingredient and reduction of its shelf-life. Moreover, US 2004/0043064 teaches that capsules made of "a cellulose-based ether, such as hydroxypropyl methylcellulose, . . . still allow for the permeation of moisture," and thus "are less than optimal since moisture transmission is often not sufficiently reduced."

For hygroscopic, moisture-sensitive active ingredients such as BH4 dihydrochloride, a capsule dosage form normally is not recommended because the active ingredient would be expected to absorb water from the material (e.g., gelatin or HPMC) in the capsule shell and thereby become unstable (e.g., labile to oxidation in the case of BH4 dihydrochloride). Contrary to conventional wisdom, stable capsule dosage forms, in which BH4 dihydrochloride has unexpected stability and prolonged shelf-life despite storage of such capsules at elevated temperature and high humidity in the absence of a desiccant, have been developed and are disclosed herein. It is particularly unexpected that the active pharmaceutical ingredient, i.e., BH4 or a BH4-related compound, within the capsule remains stable when stored in the absence of desiccant.

Another aspect of the disclosure are stable sachet dosage forms. Dry powder blends of BH4 and BH4-related compounds have unexpected physical stabilities and blend uniformities. In another embodiment, the sachet is a single chamber sachet. In another embodiment, the sachet is a dual chamber sachet. In another embodiment, the dual chamber sachet is used to separate incompatible components. In a specific embodiment, the sachet is used to prevent moisture from contacting the dry, stable BH4 or BH4-related dry blend compound.

In certain embodiments, the BH4 or a BH4-related compound in the sachet is BH4 dihydrochloride. In another particular embodiment, the sweetener is acesulfam potassium, isomalt, Magna Sweet, maltitol, mannitol, sorbitol, sucralose, xylitol, alitmae, neohesperidin dihydrochalcone, trehalose, tagatose, neotame, saccharin and salts thereof, stevioside, erythritol, isomaltulose, polydextrose, luo han guo, monatin, cyclamate, osladine, sucrose, fructose, or glucose or combinations thereof; the flavor enhancer is anhydrous citric acid, citric acid monohydrate, malic acid, tartic acid, sodium citrate, potassium citrate dehydratemonohydrate, potassium citrate anhydrous, or sodium potassium tartate or combinations thereof; the flavoring agent is a cherry, grape, orange, pink lemonade, raspberry, grape, lemon, orange, strawberry, tutti-frutti, tangerine, apple, watermelon, pineapple, banana, peach, kiwi, mango, mixed berry, raspberry lemonade, wild blackberry, blue raspberry, citrus, blueberry, lime, lemon lime, grapefruit, pomegranate, pear, or plum flavors or combinations thereof; and the sieve is a 20 mesh sieve.

In another embodiment, one chamber of the dual chamber sachet may contain the active BH4 or a BH4-related stable powder dry blend compound and the second chamber may contain the flavor blend which, if packaged together could decrease the stability and/or appearance of the active BH4 or BH4-related compound. Accordingly, the dry powder blend of BH4 dihydrochloride in a dual chamber sachet dosage has unexpected stability and prolonged shelf-life have been developed and are disclosed herein.

In another embodiment, the sachets are sealed in Mylar foil pouches. In another specific embodiment, the sachets contain a desiccant. In certain embodiments, the desiccant is, for example, a montmorillonite clay, a silica gel, an indicating silica gel, a molecular sieve, calcium oxide, calcium sulfate, activated alumina, aerogel, benzophenone, bentonite clay, calcium chloride, calcium hydride, cobalt(II) chloride, copper(II) sulfate, lithium chloride, lithium hydride, lithium bromide, magnesium, magnesium sulfate, magnesium perchlorate, a sodium-potassium alloy, phosphorus pentachloride, phosphorus pentoxide, potassium, potassium carbonate, sodium, sodium chlorate, sodium chloride, sodium hydride, sodium hydroxide, sodium sulfate, sodium-benzophenone, sucrose, or sulfuric acid or any combinations thereof. In another embodiment, the Mylar foil pouches contain a desiccant.

DEFINITIONS

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

As used in the specification and the accompanying claims, the indefinite articles "a" and "an" and the definite article "the" include plural as well as singular referents, unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, the terms "BH4", "tetrahydrobiopterin," "sapropterin," and "SAP" are used interchangeably and encompass (6R)-L-erythro-5,6,7,8-tetrahydrobiopterin, and polymorphs, tautomers, pharmaceutically acceptable salts, and solvates thereof, unless expressly indicated otherwise. The term "BH4-related compound" encompasses analogs, derivatives, prodrugs, and precursors of BH4, as well as pharmaceutically acceptable salts of BH4, unless expressly indicated otherwise.

The term "subject" refers to an animal, including but not limited to, a mammal, such as a primate (e.g., human or monkey), cow, sheep, goat, pig, horse, dog, cat, rabbit, rat, or mouse. The terms "subject" and "patient" are used interchangeably herein in reference, e.g., to a mammalian subject, such as a human subject.

The terms "treat," "treating," and "treatment" encompass alleviating or abrogating a condition, disorder, or disease, or one or more of the symptoms associated with the condition, disorder, or disease, and encompass alleviating or eradicating the cause(s) of the condition, disorder, or disease itself. In one embodiment, the terms "treat," "treating," and "treatment" refer to administration of a compound, a pharmaceutical composition, or a pharmaceutical dosage form provided herein to a subject for purposes of alleviating, abrogating, or preventing a condition, disorder, or disease, or symptom(s) associated therewith, or cause(s) thereof.

The terms "prevent," "preventing," and "prevention" encompass delaying and/or precluding the onset of a condition, disorder, or disease, and/or its attendant symptom(s); barring a subject from acquiring a disease; and reducing a subject's risk of acquiring a condition, disorder, or disease.

The term "therapeutically effective amount" encompasses the amount of a compound that, when administered, is sufficient to prevent development of, or alleviate to some extent, one or more of the symptoms of the condition, disorder, or disease being treated. The term "therapeutically effective amount" also encompasses the amount of a compound that is sufficient to elicit the biological or medical response of a cell, tissue, system, animal, or human, which is being sought by a researcher, veterinarian, medical doctor, or clinician.

In an embodiment, each component of a pharmaceutical formulation is "pharmaceutically acceptable" in the sense of being compatible with the other ingredients of the formulation, and being suitable for use in contact with cells, tissues, or organs of animals or humans without excessive toxicity, irritation, allergic response, immunogenicity, or other adverse reactions, in the amount used in the dosage form according to the dosing schedule, and commensurate with a reasonable benefit/risk ratio.

The terms "pharmaceutically acceptable carrier" and "pharmaceutically acceptable excipient" encompass pharmaceutically acceptable materials, compositions, and vehicles, such as liquid fillers, solid fillers, diluents, excipients, solvents, and encapsulating materials. Excipients also include all pharmaceutically acceptable dispersion media, coatings, isotonic agents, absorption delaying agents, antimicrobial agents, antibacterial agents, antifungal agents, adjuvants, and so on. The use of such media and agents in pharmaceutical formulations is well known in the art. Except insofar as any conventional carrier or excipient is incompatible with the active ingredient, the present disclosure encompasses the use of conventional carriers and excipients in the formulations and dosage forms described herein. See, e.g., Remington: The Science and Practice of Pharmacy, 21st Ed., Lippincott Williams & Wilkins (Philadelphia, Pa., 2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Preformulation and Formulation, Gibson, Ed., CRC Press LLC (Boca Raton, Fla., 2004).

The term "dry blend powder" encompasses powders formed from granules without moisture. A "dry blend powder" is a powder that is a homogenous blend suitable for automated sachet filling, stable in a non-hermetically sealed container, and able to dissolve in an aqueous liquid to produce a clear and/or transparent solution. For clarity, a "dry blend powder" is distinct from a wet blending product (i.e., wet milling) because the active pharmaceutical ingredient ("API") retains its crystalline form throughout the dry blend manufacturing process whereas wet blending results in loss of crystalline form of the API, particularly water soluble APIs such as BH4 or a BH4-related compound, during the manufacturing process.

The term "stable" encompasses a pharmaceutical compound or composition that retains greater than or equal to 90% of its initial potency after 3 months of storage at 40° C. and 75% Relative Humidity ("RH").

The term "dry blend flavor" encompasses a powder blend prepared by mixing dry ingredients of sapropterin dihydrochloride, sweetener, flavoring agent and flavor enhancer to form a uniform blend. The dry flavor blend quickly dissolves in water without heat and improves the palatability of sapropterin dihydrochloride.

As used herein, the term "bioavailability" refers to the fraction of an administered dose of a drug entering systemic circulation. If the drug were administered intravenously, then its bioavailability theoretically would be 100%. However, if the drug were administered via other routes (such as orally), then its bioavailability would be less than 100% as a result of, for example, incomplete absorption in the GI tract, degradation or metabolism prior to absorption, and/or hepatic first pass effect.

The term "high fat meal" refers generally to a meal of at least about 700 kcal and at least about 45% fat (relative percentage of kcal which are fat), or alternatively at least about 900 kcal and at least about 50% fat. The term "high fat food" refers generally to a food comprising at least 20 g of fat, or at least 25, 30, 35, 40, 45, or 50 g of fat, and/or at least about 45% or 50% fat. In another embodiment, a "high-fat meal" contains fat as approximately 50% of total caloric content of the meal. In another embodiment, a "high-calorie meal" contains approximately 800 to 1000 calories. In certain embodiments, a high-fat and high-calorie meal is used as a test meal for food-effect bioavailability and fed bioequivalence studies. This test meal may derive approximately 150, 250, and 500-600 calories from protein, carbohydrate and fat, respectively. An example test meal consists of two eggs fried in butter, two strips of bacon, four ounces of hash brown potatoes and eight ounces of whole milk. Substitution is possible if a similar amount of calories from protein, carbohydrate, and fat has comparable meal volume and viscosity (Guidance for Industry, Food-Effect Bioavailability and Fed Bioequivalence Studies, U.S. Department of Health and Human Services, Food and Drug Administration, Center for Drug Evaluation and Research (CDER), December 2002).

Synthesis of BH4 and BH4-Related Compounds

A variety of methods is known in the art for synthesis of tetrahydrobiopterins and precursors, derivatives, and analogs thereof. The following publications describe methods of making dihydrobiopterins, BH4 and derivatives thereof which can be used for the present disclosure: U.S. Pat. Nos. 2,601,215; 3,505,329; 4,540,783; 4,550,109; 4,587,340; 4,595,752; 4,649,197; 4,665,182; 4,701,455; 4,713,454; 4,937,342; 5,037,981; 5,198,547; 5,350,851; 5,401,844; 5,698,408; Canadian Application Publication No. CA 2,420, 374; European Application Nos. EP 079574 and EP 191335; Suntory Japanese Patent Publications Nos. JP 4-082888, JP 59-021685, and JP 9-157270; Sugimoto and Matsuura, *Bull. Chem. Soc. Jp.,* 48(12): 3767-3768 (1975); Sugimoto and Matsuura, Bull. *Chem. Soc. Jp.,* 52(1): 181-183 (1979); Matsuura et al., *Chem. Lett. Jp.,* 735-738 (1984); Matsuura et al., *Heterocycles,* 23(12): 3115-3120 (1985); and Whiteley et al., *Anal. Biochem.,* 137(2): 394-396 (1984), each of which is incorporated herein by reference in its entirety. The following publications describe methods of synthesizing BH4 which can be used for the present disclosure: WO 2005/049614; U.S. Pat. No. 4,540,783; Japanese Patent No. 59-021685; Schircks et al., *Helv. Chim. Acta,* 60: 211 (1977); Sugimoto et al., *Bull. Chem. Soc. Jp.,* 52(1): 181 (1979); Sugimoto et al., *Bull. Chem. Soc. Jp.,* 48(12): 3767 (1975); Viscontini et al., *Helv. Chim. Acta,* 52: 1225 (1969); and Matsuura et al., *Chem. Lett.,* 735 (1984), each of which is incorporated herein by reference in its entirety.

Non-limiting examples of analogs of BH4 that can be used in the formulations, stable capsules, and methods described herein include pteridine, pterin, neopterin, biopterin, 7,8-dihydrobiopterin, 6-methyltetrahydropterin, other 6-substituted tetrahydropterins, sepiapterin, 6,7-dimethyltetrahydropterin, 6-methyl biopterin, other 6-substituted biopterins, and other analogs that are described in the art. Non-limiting examples of derivatives of BH4 that can be used in the formulations, stable capsules, and methods described herein include the derivatives described in U.S. Pat. Nos. 2,541,717; 2,603,643; 2,955,110; 4,371,514; 4,758,571; 4,774,244; 5,902,810 and 6,162,806, each of which is incorporated herein by reference in its entirety.

Any of the methods disclosed in the aforementioned publications or other suitable methods can be used to produce BH4, or precursors, derivatives, or analogs thereof, for use in the dosage forms and therapeutic methods described herein.

Crystalline Polymorphs of (6R)-Tetrahydrobiopterin Hydrochloride Salt

BH4, and in particular the dihydrochloride salt of BH4, exhibits crystalline polymorphism. The structure of (6R)-L-erythro-5,6,7,8-tetrahydrobiopterin is:

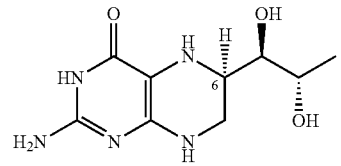 [SMILES: C[C@H](O)[C@H](O)[C@H]1CNc2nc(N)[nH]c(=O)c2N1]

The (6R) form of BH4 is the known biologically active form.

BH4 is unstable at ambient temperature and difficult to handle. The dihydrochloride salt of BH4 is known to be more stable and easier to handle than the free base (U.S. Application Publication No. 2006/0035900, which is incorporated herein by reference in its entirety). Results obtained during development of (6R)-L-erythro-tetrahydrobiopterin dihydrochloride indicated that the compound can exist in different crystalline forms, including polymorphic forms and solvates.

The crystalline polymorph of BH4 dihydrochloride that has been found to be the most stable is referred to herein as "form B", or "polymorph B". Polymorph B is a slightly hygroscopic anhydrate with the highest thermodynamic stability, above about 20° C. Furthermore, form B can be easily processed and handled due to its thermal stability and high melting point, near 260° C. ($\Delta H_f$>140 J/g). These properties render polymorph form B suitable for pharmaceutical formulations, which may be prepared at elevated temperatures. Polymorph B can be obtained as a fine powder with a particle size that may range from 0.2 μm to 500 μm.

Form B of BH4 dihydrochloride exhibits an X-ray powder diffraction pattern having peaks at, expressed in d-values (Å): 8.7 (vs), 6.9 (w), 5.90 (vw), 5.63 (m), 5.07 (m), 4.76 (m), 4.40 (m), 4.15 (w), 4.00 (s), 3.95 (m), 3.52 (m), 3.44 (w), 3.32 (m), 3.23 (s), 3.17 (w), 3.11 (vs), 3.06 (w), 2.99 (w), 2.96 (w), 2.94 (m), 2.87 (w), 2.84 (s), 2.82 (m), 2.69 (w), 2.59 (w), 2.44 (w). FIG. 1 is a graph of the characteristic X-ray powder diffraction pattern exhibited by form B of (6R)-L-erythro-tetrahydrobiopterin dihydrochloride. As used herein, the following abbreviations in brackets mean: (vs)=very strong intensity, (s)=strong intensity, (m)=medium intensity, (w)=weak intensity, and (vw)=very weak intensity.

All crystalline forms (including polymorphs, hydrates, and solvates), including form B, can be used for the preparation of polymorph B. For example, polymorph B can be obtained by phase equilibration of suspensions of amorphous or polymorphic forms of BH4, such as polymorph A, in suitable polar and non aqueous solvents. In one embodiment, the pharmaceutical preparations described herein comprise polymorph form B of (6R)-L-erythro-tetrahydrobiopterin dihydrochloride.

Other forms of BH4 can be converted to form B in other ways, e.g., by dispersing the other form of BH4 in a solvent at room temperature, stirring the suspension at ambient temperature for a time sufficient to produce polymorph form B, thereafter isolating crystalline form B, and removing the solvent from the isolated form B. Ambient temperature, as used herein, means temperature in a range from about 0° C. to about 60° C., e.g., from about 15° C. to about 40° C. The applied temperature can be changed during the preparation process by decreasing or increasing the temperature stepwise or continuously. Suitable solvents for the conversion of other forms to form B include, but are not limited to, methanol, ethanol, isopropanol, other $C_3$- and $C_4$-alcohols, acetic acid, acetonitrile, tetrahydrofuran, methyl-t-butyl ether, 1,4-dioxane, ethyl acetate, isopropyl acetate, other $C_3$-$C_6$-acetates, methyl ethyl ketone, and other methyl $C_3$-$C_5$ alkyl ketones. The time to complete phase equilibration may be up to 30 hours, e.g., up to 20 hours or less than 20 hours.

Polymorph B can also be obtained by crystallization from solvent mixtures containing up to about 5% water, e.g., from mixtures of ethanol, acetic acid, and water. Polymorph B of (6R)-L-erythro-tetrahydrobiopterin dihydrochloride can be prepared by dissolution, optionally at elevated temperatures, e.g., of a solid of lower energy form than form B or of form B of (6R)-L-erythro-tetrahydrobiopterin dihydrochloride in a solvent mixture comprising ethanol, acetic acid and water; addition of seeds to the solution; cooling the obtained suspension; and isolation of the formed crystals. Dissolution can be carried out at room temperature, up to about 70° C., or up to about 50° C. The composition of the solvent mixture may comprise a volume ratio of water:acetic acid:tetrahydrofuran of about 1:3:2 to about 1:9:4, e.g., about 1:5:4. The solution can optionally be stirred. Cooling means cooling to a temperature in the range from about −40° C. to about 30° C., e.g., from about 10° C. to about 30° C., or from about 0° C. to about 10° C. Suitable seeds are polymorph B from another batch or crystals having a similar or identical morphology. After isolation, the crystalline form B can be washed with a non-solvent, such as acetone or tetrahydrofuran, and dried in the usual manner.

Polymorph B can also be obtained by crystallization from aqueous solutions through the addition of non-solvents, such as methanol, ethanol, and acetic acid. The crystallization and isolation procedure can be advantageously carried out at room temperature without cooling the solution. This process is therefore particularly suitable to be carried out in industrial scale.

In one embodiment, a composition comprising polymorph B of (6R)-L-erythro-tetrahydrobiopterin dihydrochloride is prepared by dissolving form B, or a solid form other than form B, of (6R)-L-erythro-tetrahydrobiopterin dihydrochloride in water at ambient temperature, adding a non-solvent in an amount sufficient to form a suspension, optionally stirring the suspension for a certain time, and thereafter isolating the formed crystals. The composition is further modified into a pharmaceutical composition as described below.

The concentration of (6R)-L-erythro-tetrahydrobiopterin dihydrochloride in the aqueous solution may be from about 10% to about 80% by weight, e.g., from about 20% to about 60% by weight, by reference to the solution. Non-limiting examples of suitable non-solvents (solvents useful in preparing suspensions of BH4) include methanol, ethanol, and acetic acid. The non-solvent may be added to the aqueous solution. Alternatively, the aqueous solution may be added to the non-solvent. The stirring time after formation of the suspension may be up to 30 hours, e.g., up to 20 hours or less than 20 hours. Isolation by filtration and drying is carried out in known manner as described above.

Polymorph B of BH4 dihydrochloride is a very stable crystalline form that can be easily filtered off, dried, and ground to particle sizes desired for pharmaceutical formulations. These properties make polymorph B particularly suitable for pharmaceutical application.

In one embodiment, a composition comprising polymorph B of BH4 dihydrochloride is a very stable crystalline form that can be ground into a powder for pharmaceutical formulations. This powder form can then be blended to make polymorph B particularly suitable for dry blending with excipients for pharmaceutical application.

Stable Capsule Dosage Forms

The capsule dosage forms described herein contain BH4 dihydrochloride that exhibits unexpectedly stability. Commonly, unstable hygroscopic pharmaceuticals or pharmaceuticals unstable in the presence of water absorb water from the capsule walls and degrade in capsules. Without intending to be bound by any particular theory, one possible explanation for the degradation (and consequent loss of efficacy) of such pharmaceuticals is that hygroscopic pharmaceuticals placed in a capsule may cause the capsule to become brittle and fracture as the water present in the capsule shell is desorbed or leached from the capsule shell into the filled pharmaceutical material. Typical hard gelatin capsule shells have around 10 wt. % moisture content, and typical HPMC capsules have about 4 to 6 wt. % moisture content.

Capsule dosage forms, which comprise BH4 dihydrochloride and which are stable at room temperature or warmer for a long period of time without the capsule becoming brittle and prone to fracturing and without the BH4 dihydrochloride degrading, have been developed and are disclosed herein. In controlled studies, the BH4 dihydrochloride in the capsules provided herein unexpectedly displayed greater stability under accelerated stability testing conditions than BH4 dihydrochloride contained in previously disclosed tablet dosage forms. In certain embodiments, greater than about 95%, greater than about 96%, greater than about 97%, greater than about 98%, greater than about 99%, greater than about 99.1%, greater than about 99.2%, greater than about 99.3%, greater than about 99.4%, or greater than about 99.5% of the BH4 dihydrochloride remains after a capsule filled with a formulation comprising BH4 dihydrochloride is stored in a heat induction-sealed container at 40° C. and 75% relative humidity for six months. In further embodiments, greater than about 80%, greater than about 81%, greater than about 82%, greater than about 83%, greater than about 84%, greater than about 85%, greater than about 86%, greater than about 87%, greater than about 88%, greater than about 89%, greater than about 90%, greater than about 91%, greater than about 92%, greater than about 93%, greater than about 94%, or greater than about 95% of the BH4 dihydrochloride from such capsules dissolve within 30 minutes according to U.S.P. Method II at 50 r.p.m. in 0.1 N hydrochloric acid maintained at 37° C. Furthermore, the BH4 or BH4-related compound within the capsule remains stable when stored without desiccant.

In an embodiment, the shell of capsules comprising BH4 or a BH4-related compound can comprise one or more natural, modified, or synthetic saccharides or polysaccharides. In one embodiment, the capsule shell is made of or contains one or more derivatives of cellulose in which cellulose has been modified physically or chemically. In a specific embodiment, the cellulose derivative is hydroxypropyl methylcellulose (HPMC), also called "hypromellose". In another embodiment, the capsule shell is made of or contains one or more members of the carrageenan family of polysaccharides. In yet another embodiment, the capsule shell is made of or contains one or more starch derivatives in which starches have been modified physically or chemically.

In a further embodiment, the shell of capsules does not contain a saccharide or a polysaccharide. In a particular embodiment, the capsule shell is made of or contains gelatin. In one embodiment, the gelatin capsule is hard gelatin capsule. In another embodiment, the gelatin capsule is not soft gelatin capsule. In a further embodiment, the capsule shell is made of or contains gelatin and polyethylene glycol (PEG). In certain embodiments, the capsule shell is made of or contains gelatin and PEG 4000.

In another embodiment of non-polysaccharide capsules, the capsule shell is made of or contains one or more synthetic polymers. In one embodiment, the synthetic polymers are selected from homopolymers and copolymers formed from polyvinyl alcohol, acrylic acid, or methyl methacrylate, or combinations thereof.

The shell of capsules can also be made of or contain one or more natural materials. In certain embodiments, the natural material is acacia.

When pullulan capsules, hard gelatin capsules, and HPMC capsules comprising the same BH4-containing formulation were stored under the same conditions, the pullulan capsule shells softened and collapsed within one month, unlike the other two kinds of capsules. Accordingly, in one embodiment, the shell of capsules comprising BH4 or a BH4-related compound is essentially free of pullulan. As used herein, a "pullulan-free" capsule or a capsule "essentially free of pullulan" is a capsule having a shell that contains no pullulan or an amount of pullulan such that the stability of the capsule shell is not adversely affected by the pullulan content. In a specific embodiment, the shell of the capsule does not contain pullulan. In other embodiments where the capsule shell can contain pullulan, the capsule shell can contain no more than about 90%, no more than about 85%, no more than about 75%, no more than about 65%, no more than about 55%, no more than about 45%, no more than about 35%, no more than about 25%, no more than about 15%, no more than about 10%, no more than about 5%, no more than about 3%, no more than about 2%, no more than about 1%, no more than about 0.5%, or no more than about 0.1% pullulan by weight.

In an embodiment, the stable capsule dosage forms comprise a pharmaceutical formulation comprising a stable crystalline form of BH4 or a BH4-related compound, and one or more pharmaceutically acceptable excipients, diluents, or carriers. The capsule dosage forms optionally can further comprise one or more other therapeutic agents useful for the condition or disorder to be treated.

Because BH4 is more unstable in the presence of moisture, it is advantageous to reduce or prevent the exposure of BH4 to moisture. Accordingly, in one embodiment, the excipient(s) in the pharmaceutical formulation are anhydrous. In another embodiment, the excipient(s) are not hygroscopic. In still another embodiment, the formulation contains one or more excipients that absorb and sequester moisture.

Excipients are well known for the various kinds of pharmaceutical formulation known in the art and include, without limitation, binders (including natural and synthetic polymers), fillers, diluents, lubricants, glidants, surfactants, disintegration agents, sweetening agents, flavoring agents, coloring agents, coating materials, preservatives, dyes, thickeners, adjuvants, antimicrobial agents, antioxidants, and carriers for the various kinds of formulation. In an embodiment, the pharmaceutical formulation in the capsule dosage forms comprises BH4 or a BH4-related compound and one or more pharmaceutically acceptable excipients selected from binders, fillers, diluents, disintegration agents, glidants, antioxidants (including acidic antioxidants), lubricants, surfactants, adjuvants, sweetening agents, flavoring agents, coloring agents, and combinations thereof. In one embodiment, the formulation contains a binder, filler or diluent, and a disintegration agent. In another embodiment, the formulation further contains an acidic antioxidant. In yet another embodiment, the formulation further contains a lubricant.

Nonlimiting examples of binders useful in compositions described herein include natural and synthetic gums (e.g., acacia, gum tragacanth, guar gum); starches and derivatives thereof (e.g., corn starch, potato starch, pre-gelatinized starch); gelatin; alginic acid and alginates (e.g., sodium alginate); celluloses and derivatives thereof (e.g., microcrystalline cellulose, methyl cellulose, ethyl cellulose, hydroxypropyl methyl cellulose, cellulose acetate, carboxymethyl cellulose calcium, sodium carboxymethyl cellulose); biodegradable polymers, such as homo- and co-polyesters of dicarboxylic acids, alkylene glycols, polyalkylene glycols and/or aliphatic hydroxyl carboxylic acids; homo- and co-polyamides of dicarboxylic acids, alkylene diamines, and/or aliphatic amino carboxylic acids; corresponding polyester-polyamide-co-polymers, polyanhydrides, polyorthoesters, polyphosphazene, and polycarbonates. The biologically degradable polymers can be linear, branched, or crosslinked. Specific examples are poly-glycolic acid, poly-lactic acid, and poly-d,l-lactide/glycolide. Other non-limiting examples of polymers are water-soluble polymers, such as polyoxaalkylenes, polyoxaethylene, polyoxapropylene and mixed polymers thereof, poly-acrylamides and hydroxylalkylated polyacrylamides, poly-maleic acid and esters or amides thereof, poly-acrylic acid and esters or amides thereof, polyvinylalcohol and esters or ethers thereof, poly-vinylimidazole, polyvinylpyrrolidone, and natural polymers, such as chitosan.

Non-limiting examples of fillers and diluents include talc, calcium carbonate (e.g., granules or powder), calcium phosphate, celluloses and derivatives thereof (e.g., microcrystalline cellulose, powdered cellulose), dextrates, kaolin, mannitol, silicic acid, sorbitol, and starches and derivatives thereof (e.g., starch, pre-gelatinized starch).

Disintegration agents are believed to assist in rapid disintegration of solid pharmaceuticals by absorbing water and expanding. Non-limiting examples of disintegration agents include gums, agar, algins, alginic acid, clays, calcium carbonate, polacrilin potassium, polyvinylpyrrolidone (also called povidone), crospovidone (cross-linked povidone), celluloses and derivatives thereof (e.g., microcrystalline cellulose, croscarmellose sodium, cross-linked sodium carboxymethylcellulose (NaCMC, e.g., sold under the name AC-DI-SOL)), and starches and derivatives thereof (e.g., sodium starch glycolate, corn starch, potato starch, tapioca starch, pre-gelatinized starch). Pharmaceuticals formulated with crospovidone can exhibit more rapid disintegration than pharmaceuticals formulated with povidone.

Antioxidants can be included in the inventive compositions and can help stabilize tetrahydrobiopterin, especially after dissolution. Low pH aqueous solutions of BH4 are more stable than BH4 solutions of high pH. Exemplary acidic antioxidants include alpha-lipoic acid, ascorbic acid (including L-ascorbic acid, also called vitamin C), fatty acid esters of ascorbic acid such as ascorbyl palmitate and ascorbyl stearate, and salts of ascorbic acid such as sodium, calcium, and potassium ascorbate. Non-acidic antioxidants can also be used in the dosage forms. Nonlimiting examples of non-acidic antioxidants include vitamin A (including beta-carotene and retinol), vitamin E (including alpha-tocopherol), ebselen, 4-hydroxy-2,2,6,6-tetramethylpiperidinyloxy (TEMPOL), and superoxide dismutase. Acidic additives, e.g., citric acid and malic acid, can be added to enhance stability of the dosage forms.

The amount of ascorbic acid in the dosage forms described herein can vary depending on the condition to be treated. In one embodiment, the pharmaceutical formulation in the capsule dosage forms comprises ascorbic acid in a weight ratio of ascorbic acid to BH4 of about 1:2, 1:1.5, 1:1, 1.5:1 or 2:1. In another embodiment, the ascorbic acid to BH4 weight ratio in the formulation is no more than about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or 1:20. In a particular embodiment, the ascorbic acid to BH4 weight ratio is about 1:10 or less.

Nonlimiting examples of lubricants useful in compositions described herein include natural and synthetic oils, fats, waxes, fatty acids, and salts of fatty acids. Lubricants can improve processability and content uniformity of the pharmaceutical. Non-limiting examples of lubricants include mineral oil, light mineral oil, glycerin, sorbitol, mannitol, glycols (e.g., polyethylene glycol), hydrogenated vegetable oil (e.g., peanut oil, cottonseed oil, sunflower oil, sesame oil, olive oil, corn oil, soybean oil), talc, sodium lauryl sulfate, ethyl oleate, ethyl laureate, agar, various forms of silicon dioxide (e.g., syloid silica gel, coagulated aerosol of silica), stearyl fumaric acid and salt forms of stearyl fumarate (e.g., sodium stearyl fumarate), and stearic acid and salt forms of stearate (e.g., magnesium stearate, calcium stearate, zinc stearate).

Surfactants useful in compositions described herein can be anionic, cationic, amphoteric, or neutral. Nonlimiting examples of surfactants useful in compositions described herein include lecithin; phospholipids; alkyl sulfates, such as octyl sulfate, decyl sulfate, dodecyl sulfate, tetradecyl sulfate, hexadecyl sulfate, and octadecyl sulfate; 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid; taurocholic acid and taurodeoxycholic acid; bile acids and salts thereof, such as cholic acid, deoxycholic acid and sodium glycocholates; sodium caprate, sodium laurate, sodium oleate, sodium lauryl sulfate, sodium cetyl sulphate, sulfated castor oil, and sodium dioctylsulfosuccinate; cocamidopropylbetaine and laurylbetaine; fatty alcohols; cholesterols; glycerol mono- or -distearate, glycerol mono- or -dioleate, and glycerol mono- or -dipalmitate; and polyoxyethylene stearate.

Examples of sweetening agents include, without limitation, sucralose, sucrose, fructose, lactose, saccharin, sodium saccharide, and the like. Non-limiting examples of flavoring agents include peppermint, oil of wintergreen, orange flavoring, cherry flavoring, and the like. Examples of coloring agents include, but are not limited to, riboflavin, cochineal dye, carmine, blue No. 1 for food use, yellow No. 4 aluminum lake for food use, yellow No. 5 aluminum lake for food use, red No. 3 aluminum lake for food use, red No. 106 for food use, iron sesquioxide, yellow iron sesquioxide, and the like.

The pharmaceutical formulation in the stable capsule dosage forms described herein optionally can also comprise other excipients, such as mannitol, hydroxylpropyl cellulose, microcrystalline cellulose, and non-reducing sugars, such as xylitol, sorbitol, trehalose, melezitose, planteose, and raffinose. Without intending to be bound by any particular theory, reducing sugars may react with BH4 under certain conditions. Other excipients useful in compositions described herein include phosphates, such as dicalcium phosphate.

The pharmaceutical formulation in the stable capsule dosage forms can optionally include one or more other therapeutic agents suitable for the condition to be treated. In one embodiment, the other therapeutic agents are selected from folates, including, but not limited to, folate precursors, folic acids and folate derivatives, e.g., folinic acid (leucovorin); vitamins, such as vitamin C (ascorbic acid), vitamin B2 (riboflavin), and vitamin B12; neurotransmitter precursors, such as L-dopa, carbidopa, and serotonin; 5-hydroxytryptophan; arginine; and combinations thereof.

Exemplary folates, including folate precursors, folic acids, and folate derivatives, are disclosed in U.S. Pat. Nos. 6,011,040 and 6,544,994 (each of which is incorporated herein by reference in its entirety), and include folic acid (pteroylmonoglutamate), dihydrofolic acid, tetrahydrofolic acid, 5-methyltetrahydrofolic acid, 5,10-methylenetetrahydrofolic acid, 5,10-methenyltetrahydrofolic acid, 5,10-formiminotetrahydrofolic acid, 5-formyltetrahydrofolic acid (leucovorin), 10-formyltetrahydrofolic acid, 10-methyltetrahydrofolic acid, one or more of the folylpolyglutamates, compounds in which the pyrazine ring of the pterin moiety of folic acid or of the folylpolyglutamates is reduced to give dihydrofolates or tetrahydrofolates, derivatives of all the preceding compounds in which the N-5 or N-10 position carries one carbon unit at various levels of oxidation, pharmaceutically acceptable salts thereof, and combinations of two or more thereof. Exemplary tetrahydrofolates include 5-formyl-(6S)-tetrahydrofolic acid, 5-methyl-(6S)-tetrahydrofolic acid, 5,10-methylene-(6R)-tetrahydrofolic acid, 5,10-methynyl-(6R)-tetrahydrofolic acid, 10-formyl-(6R)-tetrahydrofolic acid, 5-formimino-(6S)-tetrahydrofolic acid, or (6S)-tetrahydrofolic acid, and pharmaceutically acceptable salts thereof. Exemplary salts include sodium, potassium, calcium, and ammonium salts. Exemplary relative weight ratios of BH4 to folates to arginine can be in a range from about 1:10:10 to about 10:1:1.

In a specific embodiment, the BH4 used in compositions described herein is formulated as a dihydrochloride salt. Other salt forms of BH4 possessing the desired physicochemical properties and biological activity can also be used. For example, BH4 salts with inorganic or organic acids are within the scope of the present disclosure. Nonlimiting examples of alternative BH4 salt forms include BH4 salts of acetic acid, citric acid, oxalic acid, tartaric acid, fumaric acid, and mandelic acid. Carbonates or hydrogen carbonates are also possible.

Pharmaceutically acceptable salts can be formed with metals or amines, such as alkali and alkaline earth metals or organic amines. Pharmaceutically acceptable salts of compounds can also be prepared with a pharmaceutically acceptable cation. Suitable pharmaceutically acceptable cations are well known to those skilled in the art and include alkaline, alkaline earth, ammonium, and quaternary ammonium cations. Non-limiting examples of metals used as cations are sodium, potassium, magnesium, ammonium, calcium, ferric, and the like. Non-limiting examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Pharmaceutically acceptable salts include inorganic and organic acid salts. Non-limiting examples of suitable salts include hydrochlorides, acetates, citrates, salicylates, nitrates, and phosphates. Other suitable pharmaceutically acceptable salts are well known to those skilled in the art and include those formed with, e.g., acetic, citric, oxalic, tartaric or mandelic acid, hydrochloric acid, hydrobromic acid, sulfuric acid, nitric acid or phosphoric acid; with organic carboxylic, sulfonic, sulfo- or phosphor-acids or N-substituted sulfamic acids, for example, acetic acid, phenylacetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, methanesulfonic acid, ethanesulfonic acid, 2-hydroxyethanesulfonic acid, ethane 1,2-disulfonic acid, benzenesulfonic acid, 4-methylbenzenesulfonic acid, 2-naphthalenesulfonic acid, naphthalene-1,5-disulfonic acid, 2- or 3-phosphoglycerate, glucose-6-phosphate, or N-cyclohexylsulfamic acid (with the formation of cyclamates); with other acid organic compounds, such as ascorbic acid; or with amino acids, such as the 20 alpha amino acids involved in the synthesis of proteins in nature, e.g., glutamic acid or aspartic acid.

In one embodiment, the pharmaceutical formulation in the stable capsule dosage forms comprises BH4 or a BH4-related compound, crospovidone, and stearyl fumaric acid or a salt form of stearyl fumarate. In an embodiment, the salt form of stearyl fumarate contains an alkali metal salt, such as lithium, sodium, potassium, and cesium. In a specific embodiment, the salt form of stearyl fumarate is sodium stearyl fumarate.

In an embodiment, the pharmaceutical formulation in the stable capsule dosage forms comprises an initial amount of BH4 or a BH4-related compound (e.g., (6R)-L-erythro-BH4 dihydrochloride) in a range from about 30% to about 70%, crospovidone from about 2% to about 10%, and stearyl fumaric acid or a salt form of stearyl fumarate (e.g., sodium stearyl fumarate) from about 0.5% to about 5%, by weight of the formulation. In narrower embodiments, the formulation comprises: (1) BH4 or a BH4-related compound from about 35% to about 65%, or from about 30% to about 60%, or from about 35% to about 60%, or from about 35% to about 55%, or from about 40% to about 60%, or from about 45% to about 55%; (2) crospovidone from about 2% to about 8%, or from about 3% to about 7%, or from about 3% to about 6%, or from about 4% to about 5%; and (3) stearyl fumaric acid or a salt form of stearyl fumarate from about 1% to about 4%, or from about 1% to about 3%, by weight of the formulation.

In another embodiment, the pharmaceutical formulation in the stable capsule dosage forms further comprises an initial amount of ascorbic acid in a range from about 0% to about 50%, silicon dioxide (e.g., colloidal silicon dioxide) from about 0% to about 5%, and mannitol from about 0% to about 50% by weight of the formulation. In narrower embodiments, the formulation further comprises: (1) ascorbic acid from about 0.5% to about 40%, or from about 1% to about 30%, or from about 1% to about 20%, or from about 1% to about 10%, or from about 0.5% to about 5%; (2) silicon dioxide from about 0.2% to about 4%, or from about 0.2% to about 3%, or from about 0.2% to about 2%; and (3) mannitol from about 5% to about 50%, or from about 20% to about 50%, or from about 30% to about 50%, or from about 25% to about 45%, or from about 10% to about 40%, or from about 20% to about 40%, or from about 15% to about 35%, by weight of the formulation.

In yet another embodiment, the pharmaceutical formulation in the stable capsule dosage forms additionally comprises an initial amount of 5-hydroxytryptophan (5-HTP) in a range from about 0% to about 50% by weight of the formulation. In narrower embodiments, the formulation additionally comprises 5-HTP from about 5% to about 45%, or from about 10% to about 40%, or from about 20% to about 40%, or from about 15% to about 35%, or from about 20% to about 30%, by weight of the formulation.

In certain embodiments, the stable capsule dosage forms described herein contain an initial amount of BH4 or a BH4-related compound (e.g., (6R)-L-erythro-BH4 dihydrochloride) in a range from about 100 mg to about 500 mg per capsule, or from about 300 mg to about 500 mg per capsule, or from about 200 mg to about 400 mg per capsule, or from about 100 mg to about 300 mg per capsule. In specific embodiments, the stable capsule dosage forms contain an initial amount of BH4 or a BH4-related compound of about 100 mg per capsule, or about 150 mg per capsule, or about 160 mg per capsule, or about 200 mg per capsule, or about 250 mg per capsule, or about 300 mg per capsule, or about 350 mg per capsule, or about 400 mg per capsule, or about 450 mg per capsule, or about 500 mg per capsule. It will be apparent to one skilled in the art that the desired dosage for the treatment, amelioration or prevention of a BH4-responsive disorder can affect the amount of BH4 or a BH4-related compound in the capsule dosage forms.

In one embodiment, provided herein are capsule dosage forms that contain relatively large amounts of BH4 (e.g., (6R)-L-erythro-BH4 dihydrochloride). A non-limiting example of such a dosage form includes 400 mg of BH4, optionally with a compaction agent, e.g., microcrystalline cellulose. Potential advantages of relatively large amounts of BH4 available in a dosage form include ease of providing the therapeutic, ease of oral administration, and patient compliance.

In an embodiment, the stable capsule dosage forms described herein are useful for treating BH4 deficiency or a condition or disorder associated with BH4 deficiency (e.g., hyperphenylalaninemia due to BH4 deficiency). In one embodiment, the stable capsule dosage forms useful for treating BH4 deficiency or a condition associated therewith comprise initial amounts of (1) BH4 or a BH4-related compound (e.g., (6R)-L-erythro-BH4 dihydrochloride) from about 30% to about 60%, or from about 40% to about 60%; (2) mannitol from about 20% to about 50%, or from about 30% to about 50%; (3) crospovidone from about 2% to about 8%, or from about 3% to about 6%; (4) stearyl fumaric acid or a salt form of stearyl fumarate (e.g., sodium stearyl fumarate) from about 1% to about 4%, or from about 1% to about 3%; (5) ascorbic acid from about 1% to about 20%, or from about 1% to about 10%; and (6) silicon dioxide (e.g., colloidal silicon dioxide) from about 0.2% to about 4%, or from about 0.2% to about 2%, by weight of the formulation. In a related embodiment, the stable capsules useful for treating BH4 deficiency or a condition associated therewith comprise an initial amount of BH4 or a BH4-related compound (e.g., (6R)-L-erythro-BH4 dihydrochloride) in a range from about 100 mg to about 500 mg per capsule, including but not limited to about 100 mg, about 150 mg, about 160 mg, about 200 mg, about 250 mg, about 300 mg, about 350 mg, about 400 mg, about 450 mg, or about 500 mg per capsule. In a particular embodiment, the shell of the stable capsules useful for treating BH4 deficiency or a condition associated therewith is made of or comprises hydroxypropyl methylcellulose (HPMC). In another embodiment, the shell of such stable capsules is made of or comprises gelatin.

In one particular embodiment, the stable capsule dosage form is useful for reducing blood phenylalanine (Phe) levels in patients with hyperphenylalaninemia (HPA) due to tetrahydrobiopterin (BH4) responsive Phenylketonuria (PKU). In another particular embodiment, the stable capsule dosage is used in conjunction with a Phe-restricted diet to reduce blood phenylalanine (Phe) levels in patients with hyperphenylalaninemia (HPA) due to tetrahydrobiopterin (BH4) responsive Phenylketonuria (PKU).

In a particular embodiment of a stable capsule dosage form useful for treating BH4 deficiency or a condition associated with BH4 deficiency (e.g., hyperphenylalaninemia due to BH4 deficiency), the pharmaceutical formulation of the dosage form comprises the following ingredients, in terms of weight % of the formulation and mg per capsule: (1) 50.0% (6R)-L-erythro-BH4 dihydrochloride (160.0 mg); (2) 38.5% mannitol (123.2 mg); (3) 5.0% ascorbic acid (16.0 mg); (4) 4.0% crospovidone (12.8 mg); (5) 1.75% sodium stearyl fumarate (5.6 mg); and (6) 0.75% colloidal silicon dioxide (2.4 mg). In one embodiment, the shell of the capsule is made of or comprises hydroxypropyl methylcellulose. In another embodiment, the capsule shell is made of or comprises gelatin. In a specific embodiment, the capsule is size 0 capsule (0.30 inch by 0.85 inch).

In another particular embodiment of a stable capsule dosage form useful for treating BH4 deficiency or a condition associated with BH4 deficiency (e.g., hyperphenylalanemia due to BH4 deficiency), the pharmaceutical formulation of the dosage form comprises the following ingredients, in terms of weight % of the formulation and mg per capsule: (1) 50.0% (6R)-L-erythro-BH4 dihydrochloride (200.0 mg); (2) 41.0% mannitol (164.0 mg); (3) 2.5% ascorbic acid (10.0 mg); (4) 4.0% crospovidone (16.0 mg); (5) 1.75% sodium stearyl fumarate (7.0 mg); and (6) 0.75% colloidal silicon dioxide (3.0 mg). In one embodiment, the shell of the capsule is made of or comprises hydroxypropyl methylcellulose. In another embodiment, the capsule shell is made of or comprises gelatin. In an embodiment, the capsule is size 0 (0.30 inch by 0.85 inch) or size 00 (0.33 inch by 0.92 inch) capsule.

In a further embodiment, the stable capsule dosage forms described herein are useful for treating sickle cell disease (SCD), peripheral arterial disease (PAD), chronic kidney disease (CKD), or hypertension. In one embodiment, the stable capsule dosage forms useful for treating SCD, PAD, CKD, or hypertension comprise initial amounts of (1) BH4 or a BH4-related compound (e.g., (6R)-L-erythro-BH4 dihydrochloride) from about 30% to about 60%, or from about 40% to about 60%, or from about 40% to about 50%; (2) ascorbic acid from about 30% to about 60%, or from about 40% to about 60%, or from about 40% to about 50%; (3) crospovidone from about 2% to about 8%, or from about 3% to about 6%; (4) stearyl fumaric acid or a salt form of stearyl fumarate (e.g., sodium stearyl fumarate) from about 1% to about 4%, or from about 1% to about 3%; (5) silicon dioxide (e.g., colloidal silicon dioxide) from about 0.2% to about 4%, or from about 0.2% to about 2%; and (6) 5-methyltetrahydrofolate (5-MTHF) or a salt form thereof from about 0% to about 2%, or from about 0.01% to about 1%, or from about 0.01% to about 0.5%, by weight of the formulation. The 5-MTHF can be a pharmaceutically acceptable salt of 5-MTHF, e.g., the calcium salt of 5-MTHF. In a related embodiment, the stable capsules useful for treating SCD, PAD, CKD, or hypertension comprise initial amounts of BH4 or a BH4-related compound (e.g., (6R)-L-erythro-BH4 dihydrochloride) and ascorbic acid in a weight ratio of about 10:1, about 9:1, about 8:1, about 7:1, about 6:1, about 5:1, about 4:1, about 3:1, about 2.5:1, about 2:1, about 1.5:1, about 1:1, about 1:1.5, or about 1:2. In another related embodiment, the stable capsules useful for treating SCD, PAD, CKD, or hypertension comprise an initial amount of BH4 or a BH4-related compound (e.g., (6R)-L-erythro-BH4 dihydrochloride) in a range from about 100 mg to about 500 mg per capsule, including but not limited to about 100 mg, about 150 mg, about 200 mg, about 250 mg, about 300 mg, about 350 mg, about 400 mg, about 450 mg, or about 500 mg per capsule. In a particular embodiment, the shell of the stable capsules useful for treating SCD, PAD, CKD, or hypertension is made of or comprises hydroxypropyl methylcellulose (HPMC). In another embodiment, the shell of such stable capsules is made of or comprises gelatin.

In a particular embodiment of a stable capsule dosage form useful for treating SCD, PAD, CKD, or hypertension, the pharmaceutical formulation of the dosage form comprises the following ingredients, in terms of weight % of the formulation and mg per capsule: (1) 46.75% (6R)-L-erythro-BH4 dihydrochloride (250.0 mg); (2) 46.75% ascorbic acid (250.0 mg); (3) 3.98% or 3.96% crospovidone (21.3 mg or 21.2 mg); (4) 1.75% sodium stearyl fumarate (9.4 mg); (5) 0.75% colloidal silicon dioxide (4.0 mg); and (6) 0.02% or 0.04% 5-methyltetrahydrofolate, calcium salt (0.1 mg or 0.2 mg). In an embodiment, the shell of the capsule is made of or comprises hydroxypropyl methylcellulose. In another embodiment, the capsule shell is made of or comprises gelatin. In yet another embodiment, the capsule is size 00 capsule (0.33 inch by 0.92 inch).

In another particular embodiment, the stable capsule dosage form can be used for treating and ameliorating autism. BH4 has been shown to be effective in treating autism in humans (see, e.g., Fernell et al., *Dev. Med. & Child Neurology*, 39: 313-318 (1997); Frye et al. *Neurotherapeutics*, 7: 241-249; Danfors et al., *J. Clinical Psychopharmacology*, 25(5): 485-489). Fernell shows that children treated with BH4 for 4, 8, and 12 weeks had significant increases in their total scores on the Parental Satisfaction Survey ("PSS"). Fernell, Table II, page 316. Frye reviews research using BH4 to treat autism and concludes that BH4 represents a novel therapy for autism spectrum disorder. Danfors shows that children treated with BH4 had significant improvement of their social interaction scores after 6 months of treatment and found a high positive correlation between response of the social interaction score and IQ.

In one embodiment, the BH4 or BH4-related compound can be used for treating or ameliorating autism in children. In one embodiment, the BH4 or BH4-related compound can be used for treating or ameliorating autism in adults. In a particular embodiment, the BH4 or BH4-related compound can be administered in conjunction with a second pharmaceutical composition to treat or ameliorate the symptoms of autism. In a particular embodiment, the second pharmaceutical compound for the combination treatment can be selected from groups consisting of stimulants, antidepressants, antianxiety medications, non-stimulant ADHD medications, antipsychotics, mood stabilizers, or Alzheimer's medications.

In a particular embodiment, the BH4 or BH4-related compound useful for treating and ameliorating autism is BH4 dihydrochloride. In a particular embodiment, BH4 dihydrochloride can be administered to children suffering from autism. In particular embodiment, the child is about 0-18 years old, 1-18 years old, about 2-18 years old, about 3-18 years old, about 3-17 years old, about 3-16 years old, about 3-15 years old, about 3-14 years old, about 3-13 years old, about 3-12 years old, about 3-11 years old, about 3-10 years old, about 3-9 years old, about 3-8 years old, about 3-7 years old, or about 3-6 years old. In a particular embodiment, the is administered to a subject during childhood and adulthood. In a particular embodiment, the formulation can be administered at a dosage of about 5-50 mg/kg/day. In a particular embodiment, the formulation can be administered at a dosage of about 5 mg/kg/day, or about 7.5 mg/kg/day, or about 10 mg/kg/day, or about 10.5 mg/kg/day, or about 11 mg/kg/day, or about 11.5 mg/kg/day, or about 12 mg/kg/day, or about 12.5 mg/kg/day, or about 13 mg/kg/day, or about 13.5 mg/kg/day, or about 14 mg/kg/day, or about 14.5 mg/kg/day, or about 15 mg/kg/day, or about 15.5 mg/kg/day, or about 16 mg/kg/day, or about 16.5 mg/kg/day, or about 17 mg/kg/day, or about 17.5 mg/kg/day, or about 18 mg/kg/day, or about 18.5 mg/kg/day, or about 19 mg/kg/day, or about 19.5 mg/kg/day, or about 20 mg/kg/day. In another embodiment, the pharmaceutical formulation comprising BH4 or a BH4-related compound can be used to treat or ameliorate autism at a dosage of 25 mg/kg/day or more.

In a particular embodiment, the stimulants administered in conjunction with the BH4 or BH4-related compound to treat and ameliorate autism may include but are not limited to amphetamines, methylphenidate, pemoline, dextroamphetamines, dexmethylphenidate, methylphenidate, and combinations thereof. The non-stimulant administered in conjunction with the BH4 or BH4-related compound to treat and ameliorate autism may include but is not limited to atomoxetine. The antidepressants and anti-anxiety medications administered in conjunction with the BH4 or BH4-related compound to treat and ameliorate autism may include, but are not limited to clomipramin, buspirone, buspirone, fluvoxamine, paroxetine, fluoxetine, nefazodone, doxepin, imipramine, bupropion, sertraline, and combinations thereof. The mood stabilizing medications administered in conjunction with the BH4 or BH4-related compound to treat and ameliorate autism may include but are not limited to lithium citrate, valproic acid, lithium carbonate, carbamazepine, and combinations thereof. The Alzheimer's medication administered in conjunction with the BH4 or BH4-related compound to treat and ameliorate autism may include but is not limited to memantine HCl.

Capsule dosage forms can be manufactured by admixing the pharmaceutical components, optionally finely dividing them, and filling capsules. An additional method for manufacturing capsule dosage forms can include compounding tetrahydrobiopterin with an excipient, e.g., a pharmaceutically acceptable carrier. Further, a capsule can then be filled with the compounded material and, optionally, the capsule can be stored in a sealed container, e.g., a heat induction-sealed polyethylene container. The compounded pharmaceutical components or powder blends can be uniformly filled into capsules using an automated capsule-filling equipment or can be manually filled into capsules, as is known in the art. It is understood that the "initial amount" of a pharmaceutical component (e.g., BH4, a BH4-related compound, 5-hydroxytryptophan, or an excipient) in a capsule is that amount of the component which is filled into the capsule in the process for producing the capsule dosage form.

In an embodiment, the stable capsule dosage forms, including the pharmaceutical formulations contained therein, are made by a process that does not include adding liquid water. The dry capsule manufacturing process comprises a dry process of mixing and blending an initial amount of the active ingredient, BH4 or a BH4-related compound (e.g., (6R)-L-erythro-BH4 dihydrochloride), with an initial amount of an excipient that optionally has been screened with an appropriate mesh screen, optionally mixing and blending the resulting ingredients with an initial amount of a second excipient that optionally has been screened, optionally doing the same with additional excipients, and filling the resulting dry blend of ingredients into capsules.

In another embodiment, the methods involve the step of informing the patient that absorption of tetrahydrobiopterin is increased when it is ingested with food compared to when ingested without food. In some embodiments, the patient is informed that ingestion shortly following a meal, for example, a high-fat, high-calorie meal, results in an increase in any one, two, three or all of the following parameters: mean plasma concentration, Cmax, AUC, AUC(0-t) and/or AUC (inf). In other embodiments, the patient is informed that administration of BH4 with a high-fat meal increases Cmax and AUC compared to administration of BH4 without food (in a fasting condition). In some embodiments, the relative increase can be at least 20% or 30% or more.

In another embodiment, such methods involve administering BH4, whether swallowed as a solid or semisolid dosage form, or dissolved in a liquid, with food, e.g., a high-fat food or a high-fat and/or high-calorie meal. In another embodiment, BH4, whether swallowed or dissolved, is administered at a specified time including but not limited to morning, day, night, same time of the day, with food, e.g., a high-fat food or a high-fat and/or high-calorie meal, one or more times a day. In another embodiment, BH4 is ingested once daily as a solid dosage form just after meals. In another embodiment the solid dosage form is a formulated tablet or capsule. In other embodiments, BH4 is ingested within approximately 0 to 30 minutes, or 5 to 20 minutes, of eating a meal.

The BH4 and the food may be ingested at approximately the same time, or the BH4 may be ingested before or after the food. The period of time between consuming the food and taking BH4, either swallowed or dissolved, may be at least 5 minutes. For example, BH4 may be administered 60 minutes, 30 minutes, 25 minutes, 20 minutes, 15 minutes, 10 minutes, or 5 minutes before or after a meal.

In another embodiment, to maximize oral bioavailability of BH4 at each administration, BH4 should be taken with food, e.g., a high fat food or a high fat and/or high calorie meal. Alternatively, to maximize consistency of oral bioavailability between administrations, BH4 should be taken on an empty stomach (e.g., 1 hour before or 2 hours after a meal).

The container or packaging containing BH4 capsule dosage forms is selected, inter alia, to minimize or prevent moisture penetration into and contamination of the formulation in the dosage form and thereby enhance the stability of the formulation. In an embodiment, BH4 capsule dosage forms are disposed in a sealed container or packaging. Examples of sealed containers include polyethylene bottles, e.g., high density polyethylene bottles closed with a heat-induction seal.

Additional non-limiting examples of sealed containers or packaging include glass bottles, tubes, hermetically sealed foil packaging, thermally sealed polyethylene bags, laminated foil pouches, and blister packs. In one embodiment, a desiccant is disposed in the container or packaging containing the BH4 capsule dosage forms, or is incorporated in the closure, stopper, or cap of the container or packaging. In another embodiment, no desiccant is disposed in the container or packaging containing the BH4 capsule dosage forms, or is incorporated in the closure, stopper, or cap of the container or packaging.

In another embodiment, at least about 90% of the initial amount of the BH4 or BH4-related compound remains, after the stable capsule dosage form is stored at about 40° C. and about 75% RH for a period of about three months. In another embodiment, at least about 91%, or at least about 92%, or at least about 93%, or at least about 94%, or at least about 95%, or at least about 96%, or at least about 97%, or at least about 98%, or at least about 99% of the initial amount of BH4 or BH4-related compound remains after the stable capsule dosage form is stored at about 40° C. and about 75% RH for a period of about three months.

In another embodiment, at least about 85% of the initial amount of the BH4 or BH4-related compound dissolves within about 15 minutes, after the stable capsule dosage form is stored at about 40° C. and about 75% RH for a period of about three months. In another embodiment, at least about 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% of the initial amount of the BH4 or BH4-related compound dissolves within about 15 minutes, after the stable capsule dosage form is stored at about 40° C. and about 75% RH for a period of about three months.

In another embodiment, at least about 90%, or at least about 91%, or at least about 92%, or at least about 93%, or at least about 94%, or at least about 95%, or at least about 96%, or at least about 97%, or at least about 98%, or at least about 99% of the initial amount of the BH4 or BH4-related compound remains and at least about 85%, or at least about 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% of the initial amount of the BH4 or BH4-related compound dissolves within about 15 minutes, after the stable capsule dosage form is stored at about 40° C. and about 75% RH for a period of about three months.

Stable Sachet Dosage Forms

The sachet dosage forms described herein contain BH4 dihydrochloride that exhibits unexpected physical stability. Commonly, granular forms of BH4 dihydrochloride are made by a wet granulation process (Sugita et al., Patent Publication No. US2008/0207624 A1). The wet granulation process consists of mixing the active ingredients with the excipients, adding a liquid binder to the powder blend and mixing thoroughly, and then screening the damp mass through a mesh to form granules. Wet granulation is often preferable because a uniform and better-flowing mixture can be easily achieved.

In contrast to wet blending, the dry blend process disclosed herein does not require the addition of a liquid binder. Instead, the different components of the mixture are added to a blender generating a powder through the blending process. Thereafter the mixture can be screened through a sieve and blended again to achieve homogeneity. However, not all mixtures are compatible with the dry blending process because in order for the dry blend to form a homogonous mixture the components must exhibit compatible abilities to flow (i.e., flowability).

Flowability refers to how a given material will flow in a given piece of equipment. It is dependent on the multidimensional characteristics of the material (e.g., powder) that are not inherent. It results from a combination of the powder's physical properties (i.e., density, cohesive strength, and wall friction) and the equipment used for handling, storing, or processing the powder. For example, powders with identical physical properties may flow differently through a hopper. Furthermore, flowability is a factor influenced by blending in which the quality of the resulting blend depends on the type of blender used and on the complex flow behavior of the powder during the blending cycle. This is because blending is accomplished by shear, convection, and diffusion and each factor is dependent on the physical properties of the material. Accordingly, the flow properties of a blend of materials cannot be determined based on the flow properties of the individual components of the blend (e.g., the flowability of small particle mannitol is different from large particle mannitol and the flow of a BH4 dihydrochloride-mannitol blend is different and not predictable based on the flow of the mannitol or BH4 alone).

Furthermore, the amount of compound used for dry blending also affects the flowability of the compound and mixtures thereof. Accordingly, in addition to selecting compounds that have compatible flow characteristics when combined in a mixture, it is also necessary to determine the correct concentration of BH4 dihydrochloride to include in the dry blend powder to achieve acceptable flowability and maintain a homogenous mixture. Thus, in order to use a dry blending process for BH4 dihydrochloride, the final mixture must remain homogenous and that can only be achieved by (1) determining the proper components of the mixture, (2) the order of addition of components of mixture, and (3) by determining how the components of the mixture behave in conjunction with one another. Accordingly, the wet granulation process is commonly used because flow properties of dry compounds are unpredictable and the wet granulation process results in the agglomeration of dry powders into larger and denser granules which flow better and granules remain homogenous because of the presence of a binder or binders to prevent segregation of the granules back into its constituent excipients and active drug substance.

However, despite the commonality of wet granulation methods, it is not ideal for all blends. Specifically, BH4 dihydrochloride is moisture sensitive and will rapidly degrade in the presence of water. Furthermore, BH4 dihydrochloride is pH sensitive and commonly degrades in the presence of reducing sugars, flavoring agents, flavor enhancers, and aqueous solutions and thus wet blending of BH4 dihydrochloride with excipients can lead to degradation of the active ingredient. Additionally, BH4 dihydrochloride which is highly soluble in water (>100 mg/mL) is solubilized during the wet granulation process leading to the loss of the stable crystalline polymorph B. BH4 dihydrochloride precipitates as a less stable amorphous form following wet granulation. Accordingly, the dry blend method of producing a stable BH4 dihydrochloride powder sachet dosage is ideal.

In one embodiment, the stable sachet dosage forms comprise a pharmaceutical formulation comprising a stable crystalline (i.e., powder) form of BH4 or a BH4-related compound, and one or more pharmaceutically acceptable excipients. The sachet dosage forms optionally can further comprise one or more other therapeutic agents useful for the condition or disorder to be treated. The sachet dosage forms can further be in the form of a single chamber sachet or a dual chamber sachet. The sachet dosage forms can further contain a stable dry blend BH4 dihydrochloride powder or a stable BH4 dihydrochloride solution that has been flushed with an inert gas and hermetically sealed.

Because BH4 is more unstable in the presence of moisture due to oxidation, it is advantageous to reduce or prevent the exposure of BH4 to moisture when the excipient and BH4 dihydrochloride are combined in the single chamber sachet. Accordingly, in one embodiment, the excipient(s) in the pharmaceutical formulation are anhydrous. In another embodiment, the excipient(s) are not hygroscopic. In another embodiment, the formulation contains one or more excipients that absorb and sequester moisture. In still another embodiment, the BH4 dihydrochloride compound is separated from the excipient(s) that are incompatible with BH4 using a dual chamber sachet.

Excipients are well known for the various kinds of pharmaceutical formulation known in the art and include, without limitation, binders (including natural and synthetic polymers), fillers, diluents, glidants, surfactants, sweetening agents, flavoring agents, coloring agents, coating materials, preservatives, dyes, thickeners, adjuvants, antimicrobial agents, antioxidants, and carriers for the various kinds of formulation. In an embodiment, the pharmaceutical formulation in the sachet dosage forms comprises BH4 or a BH4-related compound and one or more pharmaceutically acceptable excipients selected from sweetening agents, flavoring agents, flavor enhancers, and combinations thereof.

Non-limiting examples of fillers and diluents include maltose, mannitol, xylitol, sorbitol, isomalt, trehalose, and starches and derivatives thereof (e.g., starch, pre-gelatinized starch).

Antioxidants can be included in the inventive compositions and can help stabilize tetrahydrobiopterin, especially after dissolution. Low pH aqueous solutions of BH4 are more stable than BH4 solutions of high pH. Exemplary acidic antioxidants include alpha-lipoic acid, ascorbic acid (including L-ascorbic acid, also called vitamin C), fatty acid esters of ascorbic acid such as ascorbyl palmitate and ascorbyl stearate, and salts of ascorbic acid such as sodium, calcium, and potassium ascorbate. Non-acidic antioxidants can also be used in the dosage forms. Nonlimiting examples of non-acidic antioxidants include vitamin A (including beta-carotene and retinol), vitamin E (including alpha-tocopherol), ebselen, 4-hydroxy-2,2,6,6-tetramethylpiperidinyloxy (TEMPOL), and superoxide dismutase. Acidic additives, e.g., citric acid and malic acid, can be added to enhance stability of the dosage forms.

The amount of ascorbic acid in the dosage forms described herein can vary depending on the condition to be treated. In one embodiment, the pharmaceutical formulation in the sachet dosage forms comprises ascorbic acid in a weight ratio of ascorbic acid to BH4 of about 1:2, 1:1.5, 1:1, 1.5:1 or 2:1. In another embodiment, the ascorbic acid to BH4 weight ratio in the formulation is no more than about 1:2, 1:3, 1:4, 1:5, 1:6, 1:7, 1:8, 1:9, 1:10, 1:11, 1:12, 1:13, 1:14, 1:15, 1:16, 1:17, 1:18, 1:19 or 1:20. In a particular embodiment, the ascorbic acid to BH4 weight ratio is about 1:10 or less.

Nonlimiting examples of lubricants useful in compositions described herein include natural and synthetic oils, fats, waxes, fatty acids, and salts of fatty acids. Lubricants can improve processability and content uniformity of the pharmaceutical. Non-limiting examples of lubricants include mineral oil, light mineral oil, glycerin, sorbitol, mannitol, glycols (e.g., polyethylene glycol), hydrogenated vegetable oil (e.g., peanut oil, cottonseed oil, sunflower oil, sesame oil, olive oil, corn oil, soybean oil), talc, sodium lauryl sulfate, ethyl oleate, ethyl laureate, agar, various forms of silicon dioxide (e.g., syloid silica gel, coagulated aerosol of silica), stearyl fumaric acid and salt forms of stearyl fumarate (e.g., sodium stearyl fumarate), and stearic acid and salt forms of stearate (e.g., magnesium stearate, calcium stearate, zinc stearate).

Surfactants useful in compositions described herein can be anionic, cationic, amphoteric, or neutral. Nonlimiting examples of surfactants useful in compositions described herein include lecithin; phospholipids; alkyl sulfates, such as octyl sulfate, decyl sulfate, dodecyl sulfate, tetradecyl sulfate, hexadecyl sulfate, and octadecyl sulfate; 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid; taurocholic acid and taurodeoxycholic acid; bile acids and salts thereof, such as cholic acid, deoxycholic acid and sodium glycocholates; sodium caprate, sodium laurate, sodium oleate, sodium lauryl sulphate, sodium cetyl sulphate, sulfated castor oil, and sodium dioctylsulfosuccinate; cocamidopropylbetaine and laurylbetaine; fatty alcohols; cholesterols; glycerol mono- or -distearate, glycerol mono- or -dioleate, and glycerol mono- or -dipalmitate; and polyoxyethylene stearate.

Examples of sweetening agents include, without limitation, acesulfam potassium, isomalt, Magna Sweet, maltitol, mannitol, sorbitol, sucralose, xylitol, alitmae, neohesperidin dihydrochalcone, trehalose, tagatose, neotame, saccharin and salts thereof, stevioside, erythritol, isomaltulose, polydextrose, luo han guo, monatin, cyclamate, glycyrrhizin, osladine, sucrose, fructose, or glucose or combinations thereof.

Non-limiting examples of flavoring agents include cherry, grape, orange, pink lemonade, raspberry, grape, lemon, orange, strawberry, tutti-frutti, tangerine, apple, watermelon, pineapple, banana, peach, kiwi, mango, mixed berry, raspberry lemonade, wild blackberry, blue raspberry, citrus, blueberry, lime, lemon lime, grapefruit, pomegranate, pear, or plum flavors, bubble gum, or combinations thereof.

Non-limiting examples of flavor enhancer agents include anhydrous citric acid, citric acid monohydrate, malic acid, tartaric acid, sodium citrate, potassium citratemonohydrate, potassium citrate anhydrous, or sodium potassium tartate or combinations thereof.

Non-limiting examples of coloring agents include, but are not limited to, riboflavin, cochineal dye, carmine, blue No. 1 for food use, yellow No. 4 aluminum lake for food use, yellow No. 5 aluminum lake for food use, red No. 3 aluminum lake for food use, red No. 106 for food use, iron sesquioxide, yellow iron sesquioxide, pharmaceutical dyes such as FD&C Blue No. 2, FD&C Blue No. 1, FD&C Green No. 3, FD&C Red No. 3, FD&C Red No. 4, FD&C Red No. 40, FD&C Yellow No. 6, FD&C Yellow No. 5, and the like.

The pharmaceutical formulation in the stable sachet dosage forms described herein optionally can also comprise other excipients, such as non-reducing sugars, such as melezitose, planteose, and raffinose. Without intending to be bound by any particular theory, reducing sugars may react with BH4 under certain conditions. Other excipients useful in compositions described herein include phosphates, such as dicalcium phosphate.

The pharmaceutical formulation in the stable sachet dosage forms can optionally include one or more other therapeutic agents suitable for the condition to be treated. In one embodiment the therapeutic agent can be blended with the stable BH4 dihydrochloride powder. In another embodiment the therapeutic agent is contained in one chamber of a dual chamber sachet and the stable BH4 dihydrochloride dry blend powder is in the second chamber. In one embodiment, the other therapeutic agents are selected from folates, including, but not limited to, folate precursors, folic acids and folate derivatives, e.g., folinic acid (leucovorin); vitamins, such as vitamin C (ascorbic acid), vitamin B2 (riboflavin), and vitamin B12; neurotransmitter precursors, such as L-dopa, carbidopa, and serotonin; 5-hydroxytryptophan; arginine; and combinations thereof.

Exemplary folates, including folate precursors, folic acids, and folate derivatives, are disclosed in U.S. Pat. Nos. 6,011,040 and 6,544,994 (each of which is incorporated herein by reference in its entirety), and include folic acid (pteroylmonoglutamate), dihydrofolic acid, tetrahydrofolic acid, 5-methyltetrahydrofolic acid, 5,10-methylenetetrahydrofolic acid, 5,10-methenyltetrahydrofolic acid, 5,10-formiminotetrahydrofolic acid, 5-formyltetrahydrofolic acid (leucovorin), 10-formyltetrahydrofolic acid, 10-methyltetrahydrofolic acid, one or more of the folylpolyglutamates, compounds in which the pyrazine ring of the pterin moiety of folic acid or of the folylpolyglutamates is reduced to give dihydrofolates or tetrahydrofolates, derivatives of all the preceding compounds in which the N-5 or N-10 position carries one carbon unit at various levels of oxidation, pharmaceutically acceptable salts thereof, and combinations of two or more thereof. Exemplary tetrahydrofolates include 5-formyl-(6S)-tetrahydrofolic acid, 5-methyl-(6S)-tetrahydrofolic acid, 5,10-methylene-(6R)-tetrahydrofolic acid, 5,10-methynyl-(6R)-tetrahydrofolic acid, 10-formyl-(6R)-tetrahydrofolic acid, 5-formimino-(6S)-tetrahydrofolic acid, or (6S)-tetrahydrofolic acid, and pharmaceutically acceptable salts thereof. Exemplary salts include sodium, potassium, calcium, and ammonium salts. Exemplary relative weight ratios of BH4 to folates to arginine can be in a range from about 1:10:10 to about 10:1:1.

In a specific embodiment, the BH4 used in compositions described herein is formulated as a dihydrochloride salt. Other salt forms of BH4 possessing the desired physicochemical properties and biological activity can also be used. For example, BH4 salts with inorganic or organic acids are within the scope of the present disclosure. Nonlimiting examples of alternative BH4 salt forms include BH4 salts of acetic acid, citric acid, oxalic acid, tartaric acid, fumaric acid, and mandelic acid. Carbonates or hydrogen carbonates are also possible.

Pharmaceutically acceptable salts can be formed with metals or amines, such as alkali and alkaline earth metals or organic amines. Pharmaceutically acceptable salts of compounds can also be prepared with a pharmaceutically acceptable cation. Suitable pharmaceutically acceptable cations are well known to those skilled in the art and include alkaline, alkaline earth, ammonium, and quaternary ammonium cations. Non-limiting examples of metals used as cations are sodium, potassium, magnesium, ammonium, calcium, ferric, and the like. Non-limiting examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Furthermore, the pharmaceutically acceptable salts include inorganic and organic acid salts. Non-limiting examples of suitable salts include hydrochlorides, acetates, citrates, salicylates, nitrates, and phosphates. Other suitable pharmaceutically acceptable salts are well known to those skilled in the art and include those formed with, e.g., acetic, citric, oxalic, tartaric or mandelic acid, hydrochloric acid, hydrobromic acid, sulfuric acid, nitric acid or phosphoric acid; with organic carboxylic, sulfonic, sulfo- or phosphor- acids or N-substituted sulfamic acids, for example, acetic acid, phenylacetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, methanesulfonic acid, ethanesulfonic acid, 2-hydroxyethanesulfonic acid, ethane 1,2-disulfonic acid, benzenesulfonic acid, 4-methylbenzenesulfonic acid, 2-naphthalenesulfonic acid, naphthalene-1,5-disulfonic acid, 2- or 3-phosphoglycerate, glucose-6-phosphate, or N-cyclohexylsulfamic acid (with the formation of cyclamates); with other acid organic compounds, such as ascorbic acid; or with amino acids, such as the 20 alpha amino acids involved in the synthesis of proteins in nature, e.g., glutamic acid or aspartic acid.

In an embodiment, the pharmaceutical formulation in the stable sachet dosage forms contains about 5%, about 7.5%, about 10%, about 12.5%, about 15%, about 17.5%, about 20%, about 22.5%, about 25%, about 27.5%, about 30%, about 32.5%, about 35%, about 37.5%, about 40%, about 42.5%, about 45%, about 47.5%, about 50%, about 52.5%, or about 55% BH4 dihydrochloride. In certain embodiments, the stable sachet dosage forms contain between about 10-50%, about 10-40%, about 10-30%, about 10-20%, about 20-50%, about 30-50%, about 40-50%, or about 50-55% BH4 dihydrochloride.

In an embodiment, the pharmaceutical formulation in the stable sachet dosage forms comprise an amount of BH4 dihydrochloride of about 15% and between 75-80% mannitol, about 0-1% sucralose, about 1.5% flavoring agent, between 4.5-7% potassium citrate or potassium sodium tartrate, and about 1% ascorbic acid fine powder. In a specific embodiment, the flavoring agent is strawberry, orange on a sucrose substrate, orange on a mannitol substrate, or grape. In another specific embodiment, the blend also consists of about 5% potassium citrate.

In an embodiment, the pharmaceutical formulation in the stable sachet dosage forms comprise an amount of BH4 dihydrochloride of about 15.1% BH4 dihydrochloride, 75.3% mannitol, 1.5% orange flavor on a sucrose base, 0.8% sucralose, 4.8% potassium citrate, and 0.8% ascorbic acid fine powder.

In an embodiment, the pharmaceutical formulation in the stable sachet dosage forms comprise an amount of BH4 dihydrochloride of about 15.3% BH4 dihydrochloride, 76.7% mannitol, 1.5% orange flavor on a mannitol base, 0.8% sucralose, 4.8% potassium citrate, and 0.8% ascorbic acid fine powder.

In yet another embodiment, the pharmaceutical formulation in the stable sachet dosage forms additionally comprises an amount of 5-hydroxytryptophan (5-HTP) in a range from about 0% to about 50% by weight of the formulation. In one embodiment, the 5-HTP is dry blended with the BH4 dihydrochloride. In another embodiment, the 5-HT is contained in one chamber of a dual chamber sachet and the BH4 dihydrochloride is contained in the second chamber. In narrower embodiments, the formulation additionally comprises 5-HTP from about 5% to about 45%, or from about 10% to about 40%, or from about 20% to about 40%, or from about 15% to about 35%, or from about 20% to about 30%, by weight of the formulation.

In yet another embodiment, the pharmaceutical formulations in the stable sachet dosage forms are blends that contain of approximately 32% drug, 55% mannitol, and 1.6% to 2% sucralose. For example:

| Ingredient | Formulation A g/sachet | % | Formulation B g/sachet | % | Formulation C g/sachet | % |
|---|---|---|---|---|---|---|
| Sapropterin HCl | 0.2 | 32 | 0.2 | 32 | 0.2 | 32 |
| Mannitol | 0.34 | 54.4 | 0.3388 | 54.2 | 0.3375 | 54.0 |
| Sucralose | 0.01 | 1.6 | 0.0113 | 1.8 | 0.0125 | 2.0 |
| Potassium Citrate | 0.065 | 10.4 | 0.065 | 10.4 | 0.065 | 10.4 |
| Ascorbic Acid | 0.01 | 1.6 | 0.01 | 1.6 | 0.01 | 1.6 |
| Total | 0.625 | 100 | 0.625 | 100 | 0.625 | 100 |

In yet another embodiment, the pharmaceutical formulation in the stable sachet dosage contains approximately 32% drug, 54.1% mannitol, 1.9% sucralose micronized, 10.4% potassium citrate monohydrate, and 1.6% ascorbic acid fine powder.

In certain embodiments, the stable sachet dosage forms described herein contain an amount of BH4 or a BH4-related compound (e.g., (6R)-L-erythro-BH4 dihydrochloride) in a range from about 50 mg to about 1300 mg (i.e., 1.3 g) per sachet, or from about 100 mg to about 1300 mg per sachet, or from about 200 mg to about 1300 mg per sachet, or from about 300 mg to about 1300 mg per sachet, or from about 400 mg to about 1300 mg per sachet, or from about 500 mg to about 1300 mg per sachet, or from about 600 mg to about 1300 mg per sachet, or from about 700 mg to about 1300 mg per sachet, or from about 800 mg to about 1300 mg per sachet, or from about 900 mg to about 1300 mg per sachet, or from about 1000 mg to about 1300 mg per sachet, or from about 50 mg to about 500 mg per sachet, or from about 100 mg to about 500 mg per sachet, or from about 200 mg to about 500 mg per sachet, or from about 300 mg to about 500 mg per sachet, or from about 100 mg to about 700 mg per sachet, or from about 200 mg to about 700 mg per sachet, or from about 300 mg to about 700 mg per sachet, or from about 400 mg to about 700 mg per sachet. In specific embodiments, the stable sachet dosage forms contain an initial amount of BH4 or a BH4-related compound of about 50 mg per sachet, 100 mg per sachet, or about 150 mg per sachet, or about 160 mg per sachet, or about 200 mg per sachet, or about 250 mg per sachet, or about 300 mg per sachet, or about 350 mg per sachet, or about 400 mg per sachet, or about 450 mg per sachet, or about 500 mg per sachet, or about 550 mg per sachet, or about 600 mg per sachet, or about 650 mg per sachet, or about 700 mg per sachet, or about 750 mg per sachet, or about 800 mg per sachet, or about 850 mg per sachet, or about 900 mg per sachet, or about 950 mg per sachet, or about 1000 mg per sachet, or about 1050 mg per sachet, or about 1100 mg per sachet, or about 1150 mg per sachet, or about 1200 mg per sachet, or about 1250 mg per sachet, or about 1300 mg per sachet, or about 1350 mg per sachet. It will be apparent to one skilled in the art that the desired dosage for the treatment, amelioration or prevention of a BH4-responsive disorder can affect the amount of BH4 or a BH4-related compound in the sachet dosage forms.

In one embodiment, provided herein are sachet dosage forms that contain relatively large amounts of BH4 (e.g., (6R)-L-erythro-BH4 dihydrochloride). A non-limiting example of such a dosage form includes 500 mg of BH4, or 600 mg of BH4, or 700 mg of BH4, or 800 mg of BH4, or 900 mg of BH4, or 1000 mg of BH4, or 1100 mg of BH4, or 1200 mg of BH4, or 1300 mg of BH4. Potential advantages of relatively large amounts of BH4 available in a dosage form include ease of providing the therapeutic, ease of oral administration, and patient compliance.

It is particularly unexpected that weights of about 600 mg or more, for example, of a dry blend powder have flow properties that are amenable to automated sachet filling. Accordingly, it is unexpected that stable sachet dosage forms described herein contain, for example, 600 mg or more of a BH4 or BH4-related compound dry blend powder.

In an embodiment, the stable sachet dosage forms described herein are useful for treating BH4 deficiency or a condition or disorder associated with BH4 deficiency (e.g., hyperphenylalaninemia due to BH4 deficiency). In a specific embodiment, the stable sachet dosage is used reduce blood phenylalanine levels in patients with hyperphenylalaninemia due to tetrahydrobiopterin-responsive phenylketonuria. In another specific embodiment, the stable sachet dosage is used reduce blood phenylalanine levels in patients with hyperphenylalaninemia due to tetrahydrobiopterin-responsive phenylketonuria in conjunction with a phenylalanine restricted diet.

In one embodiment, the stable sachet dosage forms useful for treating BH4 deficiency or a condition associated therewith comprise amounts of (1) BH4 or a BH4-related compound (e.g., (6R)-L-erythro-BH4 dihydrochloride) from about 30% to about 60%, or from about 40% to about 60%; (2) mannitol from about 20% to about 50%, or from about 30% to about 50%; (3) crospovidone from about 2% to about 8%, or from about 3% to about 6%; (4) stearyl fumaric acid or a salt form of stearyl fumarate (e.g., sodium stearyl fumarate) from about 1% to about 4%, or from about 1% to about 3%; (5) ascorbic acid from about 1% to about 20%, or from about 1% to about 10%; and (6) silicon dioxide (e.g., colloidal silicon dioxide) from about 0.2% to about 4%, or from about 0.2% to about 2%, by weight of the formulation. In a related embodiment, the stable sachet useful for treating BH4 deficiency or a condition associated therewith comprise an initial amount of BH4 or a BH4-related compound (e.g., (6R)-L-erythro-BH4 dihydrochloride) in a range from about 50 mg to about 1300 mg per sachet, including but not limited to about 50 mg per sachet, 100 mg per sachet, or about 150 mg per sachet, or about 160 mg per sachet, or about 200 mg per sachet, or about 250 mg per sachet, or about 300 mg per sachet, or about 350 mg per sachet, or about 400 mg per sachet, or about 450 mg per sachet, or about 500 mg per sachet, or about 550 mg per sachet, or about 600 mg per sachet, or about 650 mg per sachet, or about 700 mg per sachet, or about 750 mg per sachet, or about 800 mg per sachet, or about 850 mg per sachet, or about 900 mg per sachet, or about 950 mg per sachet, or about 1000 mg per sachet, or about 1050 mg per sachet, or about 1100 mg per sachet, or about 1150 mg per sachet, or about 1200 mg per sachet, or about 1250 mg per sachet, or about 1300 mg per sachet, or about 1350 mg per sachet.

In a further embodiment, the stable sachet dosage forms described herein are useful for treating sickle cell disease (SCD), peripheral arterial disease (PAD), chronic kidney disease (CKD), or hypertension. In one embodiment, the stable sachet dosage forms useful for treating SCD, PAD, CKD, or hypertension comprise initial amounts of (1) BH4 or a BH4-related compound (e.g., (6R)-L-erythro-BH4 dihydrochloride) from about 30% to about 60%, or from about 40% to about 60%, or from about 40% to about 50%; (2) ascorbic acid from about 30% to about 60%, or from about 40% to about 60%, or from about 40% to about 50%; (3) crospovidone from about 2% to about 8%, or from about 3% to about 6%; (4) stearyl fumaric acid or a salt form of stearyl fumarate (e.g., sodium stearyl fumarate) from about 1% to about 4%, or from about 1% to about 3%; (5) silicon dioxide (e.g., colloidal silicon dioxide) from about 0.2% to about 4%, or from about 0.2% to about 2%; and (6) 5-methyltetrahydrofolate (5-MTHF) or a salt form thereof from about 0% to about 2%, or from about 0.01% to about 1%, or from about 0.01% to about 0.5%, by weight of the formulation. The 5-MTHF can be a pharmaceutically acceptable salt of 5-MTHF, e.g., the calcium salt of 5-MTHF. In a related embodiment, the stable sachets useful for treating SCD, PAD, CKD, or hypertension comprise initial amounts of BH4 or a BH4-related compound (e.g., (6R)-L-erythro-BH4 dihydrochloride) and ascorbic acid in a weight ratio of about 10:1, about 9:1, about 8:1, about 7:1, about 6:1, about 5:1, about 4:1, about 3:1, about 2.5:1, about 2:1, about 1.5:1, about 1:1, about 1:1.5, or about 1:2. In another related embodiment, the stable sachets useful for treating SCD, PAD, CKD, or hypertension comprise an initial amount of BH4 or a BH4-related compound (e.g., (6R)-L-erythro-BH4 dihydrochloride) in a range from about 50 mg to about 1300 mg per sachet, including but not limited about 50 mg per sachet, 100 mg per sachet, or about 150 mg per sachet, or about 160 mg per sachet, or about 200 mg per sachet, or about 250 mg per sachet, or about 300 mg per sachet, or about 350 mg per sachet, or about 400 mg per sachet, or about 450 mg per sachet, or about 500 mg per sachet, or about 550 mg per sachet, or about 600 mg per sachet, or about 650 mg per sachet, or about 700 mg per sachet, or about 750 mg per sachet, or about 800 mg per sachet, or about 850 mg per sachet, or about 900 mg per sachet, or about 950 mg per sachet, or about 1000 mg per sachet, or about 1050 mg per sachet, or about 1100 mg per sachet, or about 1150 mg per sachet, or about 1200 mg per sachet, or about 1250 mg per sachet, or about 1300 mg per sachet, or about 1350 mg per sachet.

In a particular embodiment of a stable sachet dosage form useful for treating SCD, PAD, CKD, or hypertension, the pharmaceutical formulation of the dosage form comprises the following ingredients, in terms of weight % of the formulation and mg per capsule: (1) 46.75% (6R)-L-erythro-BH4 dihydrochloride (250.0 mg); (2) 46.75% ascorbic acid (250.0 mg); (3) 3.98% or 3.96% crospovidone (21.3 mg or 21.2 mg); (4) 1.75% sodium stearyl fumarate (9.4 mg); (5) 0.75% colloidal silicon dioxide (4.0 mg); and (6) 0.02% or 0.04% 5-methyltetrahydrofolate, calcium salt (0.1 mg or 0.2 mg).

In another particular embodiment, the stable sachet dosage form can be used for treating or ameliorating autism. BH4 has been shown to be effective in treating autism in humans (see, e.g., Fernell et al., *Dev. Med. & Child Neurology,* 39: 313-318 (1997); Frye et al. *Neurotherapeutics,* 7: 241-249; Danfors et al., *J. Clinical Psychopharmacology,* 25(5): 485-489). Fernell shows that children treated with BH4 for 4, 8, and 12 weeks had significant increases in their total scores on the Parental Satisfaction Survey ("PSS"). Fernell, Table II, page 316. Frye reviews research using BH4 to treat autism and concludes that BH4 represents a novel therapy for autism spectrum disorder. Danfors shows that children treated with BH4 had significant improvement of their social interaction scores after 6 months of treatment and found a high positive correlation between response of the social interaction score and IQ.

In one embodiment, the BH4 or BH4-related compound can be used for treating or ameliorating autism in children. In one embodiment, the BH4 or BH4-related compound can be used for treating or ameliorating autism in adults. In a particular embodiment, the BH4 or BH4-related compound can be administered in conjunction with a second pharmaceutical composition to treat or ameliorate the symptoms of autism. In a particular embodiment, the second pharmaceutical compound for the combination treatment can be selected from groups consisting of stimulants, antidepressants, antianxiety medications, non-stimulant ADHD medications, antipsychotics, mood stabilizers, or Alzheimer's medications.

Sachet dosage forms can be manufactured by dry blending the components of the sachet and sealing them in a single or dual chamber sachet. The sachet can be flushed with an inert gas and hermetically sealed. The sachet can also contain a desiccant. The sachet can be made out of Mylar foil. Further, the sachet can then be filled with the compounded material and, optionally, the capsule can be stored in a sealed container, e.g., a Mylar foil package. The Mylar foil package may contain a desiccant and may be flushed with inert gas and may be hermetically sealed. The compounded pharmaceutical components or powder blends can be uniformly filled into sachets using an automated sachet-filling equipment or can be manually filled into sachets, as is known in the art.

In an embodiment, the stable sachet dosage forms, including the pharmaceutical formulations contained therein, are made by a process that does not include adding an aqueous liquid. The dry blend manufacturing process comprises a dry process of mixing and blending an initial amount of the active ingredient, BH4 or a BH4-related compound (e.g., (6R)-L-erythro-BH4 dihydrochloride), with an initial amount of an excipient that optionally has been screened with an appropriate mesh screen, optionally mixing and blending the resulting ingredients with an initial amount of a second excipient that optionally has been screened, optionally doing the same with additional excipients, and filling the resulting dry blend of ingredients into capsules.

In another embodiment, the methods involve the step of informing the patient that absorption of tetrahydrobiopterin is increased when it is ingested with food compared to when ingested without food. In some embodiments, the patient is informed that ingestion shortly following a meal, for example, a high-fat, high-calorie meal, results in an increase in any one, two, three or all of the following parameters: mean plasma concentration, Cmax, AUC, AUC(O-t) and/or AUC (inf). In other embodiments, the patient is informed that administration of BH4 with a high-fat meal increases Cmax and AUC compared to administration of BH4 without food (in a fasting condition). In some embodiments, the relative increase can be at least 20% or 30% or more.

In another embodiment, such methods involve administering BH4, whether swallowed as a solid or semisolid dosage form, or dissolved in a liquid, with food, e.g., a high-fat food or a high-fat and/or high-calorie meal. In another embodiment, BH4, whether swallowed or dissolved, is administered at a specified time including but not limited to morning, day, night, same time of the day, with food, e.g., a high-fat food or a high-fat and/or high-calorie meal, one or more times a day. In another embodiment, BH4 is ingested once daily as a solid dosage form just after meals. In another embodiment the solid dosage form is a formulated tablet or capsule. In other embodiments, BH4 is ingested within approximately 0 to 30 minutes, or 5 to 20 minutes, of eating a meal.

The BH4 and the food may be ingested at approximately the same time, or the BH4 may be ingested before or after the food. The period of time between consuming the food and taking BH4, either swallowed or dissolved, may be at least 5 minutes. For example, BH4 may be administered 60 minutes, 30 minutes, 25 minutes, 20 minutes, 15 minutes, 10 minutes, or 5 minutes before or after a meal.

In another embodiment, to maximize oral bioavailability of BH4 at each administration, BH4 should be taken with food, e.g., a high fat food or a high fat and/or high calorie meal. Alternatively, to maximize consistency of oral bioavailability between administrations, BH4 should be taken on an empty stomach (e.g., 1 hour before or 2 hours after a meal).

The container or packaging containing BH4 sachet dosage forms is selected, inter alia, to minimize or prevent moisture penetration into and contamination of the formulation in the dosage form and thereby enhance the stability of the formulation. In an embodiment, BH4 sachet dosage forms are disposed in a sealed container or packaging. Examples of sealed containers include Mylar foil pouches. Additional non-limiting examples of sealed containers or packaging include polyethylene bottles, e.g., high density polyethylene bottles closed with a heat-induction seal, glass bottles, tubes, hermetically sealed foil packaging, thermally sealed polyethylene bags, laminated foil pouches, and blister packs. In one embodiment, a desiccant is disposed in the container or packaging containing the BH4 sachet dosage forms, or is incorporated in the closure, stopper or cap of the container or packaging. In one embodiment the container is flushed with inert gas prior to being hermetically sealed.

In another embodiment, at least about 90% of the initial amount of the BH4 or BH4-related compound remains, after the sachet dosage form is stored at about 40° C. and about 75% RH for a period of about three months. In another embodiment, at least about 91%, or at least about 92%, or at least about 93%, or at least about 94%, or at least about 95%, or at least about 96%, or at least about 97%, or at least about 98%, or at least about 99% of the initial amount of BH4 or BH4-related compound remains after the sachet dosage form is stored at about 40° C. and about 75% RH for a period of about three months.

In another embodiment, at least about 85% of the initial amount of the BH4 or BH4-related compound dissolves within about 15 minutes, after the sachet dosage form is stored at about 40° C. and about 75% RH for a period of about three months. In another embodiment, at least about 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% of the initial amount of the BH4 or BH4-related compound dissolves within about 15 minutes, after the sachet dosage form is stored at about 40° C. and about 75% RH for a period of about three months.

In another embodiment, at least about 90%, or at least about 91%, or at least about 92%, or at least about 93%, or at least about 94%, or at least about 95%, or at least about 96%, or at least about 97%, or at least about 98%, or at least about 99% of the initial amount of the BH4 or BH4-related compound remains and at least about 85%, or at least about 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% of the initial amount of the BH4 or BH4-related compound dissolves within about 15 minutes, after the sachet dosage form is stored at about 40° C. and about 75% RH for a period of about three months.

In another embodiment, at least about 85%, or at least about 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% of the initial amount of the BH4 or BH4-related compound dissolves within about 1 minute, or within about 2 minutes, or within about 3 minutes, or within about 4 minutes, or within about 5 minutes, or within about 6 minutes, or within about 7 minutes, or within about 8 minutes, or within about 9 minutes, or within about 10 minutes with gentle agitation, after the sachet dosage form is stored at about 40° C. and about 75% RH for a period of about three months. In certain embodiments the gentle agitation is stirring or shaking.

In another embodiment, at least about 90%, or at least about 91%, or at least about 92%, or at least about 93%, or at least about 94%, or at least about 95%, or at least about 96%, or at least about 97%, or at least about 98%, or at least about 99% of the initial amount of the BH4 or BH4-related compound remains and at least about 85%, or at least about 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% of the initial amount of the BH4 or BH4-related compound dissolves within about 1 minute, or within about 2 minutes, or within about 3 minutes, or within about 4 minutes, or within about 5 minutes, or within about 6 minutes, or within about 7 minutes, or within about 8 minutes, or within about 9 minutes, or within about 10 minutes with gentle agitation, after the sachet dosage form is stored at about 40° C. and about 75% RH for a period of about three months. In certain embodiments the gentle agitation is stirring or shaking.

Therapeutic Methods Using Stable Dosage Forms

It will be appreciated that therapeutic methods applicable to the stable dosage forms described herein include the fields of human medicine and veterinary medicine. Thus, the subject to be treated can be a mammal, e.g., human or other animal.

The stable dosage forms described herein can be used for treating, ameliorating or preventing, e.g., conditions associated with elevated phenylalanine levels or decreased tyrosine or tryptophan levels. Such conditions may be caused, for example, by reduced phenylalanine hydroxylase activity or reduced tyrosine hydroxylase or tryptophan hydroxylase activity. Conditions associated with elevated phenylalanine levels include, e.g., phenylketonuria, both mild and classic, and hyperphenylalanemia (also written as hyperphenylalaninemia), and exemplary patient populations include the patient subgroups described herein as well as any other patients exhibiting phenylalanine levels above normal. Conditions associated with reduced tyrosine or tryptophan levels include, e.g., neurotransmitter deficiency, neurological and psychiatric disorders such as Parkinson's, dystonia, spinocerebellar degeneration, pain, fatigue, depression, other affective disorders, and schizophrenia. Non-limiting examples of other BH4-responsive conditions that can be treated, ameliorated or prevented by use of the BH4 stable capsule dosage forms described herein include BH4 deficiency, sickle cell anemia, hypertension and autism.

Genetic disorders resulting in hyperphenylalaninemia (HPA) involve deficiency in the enzyme phenylalanine hydroxylase (PAH), which causes phenylketonuria (PKU), and deficiency in the essential PAH cofactor, tetrahydrobiopterin (BH4), which causes disorders known as BH4 deficiency. BH4 is an essential cofactor for several enzymes, including PAH, tyrosine hydroxylase, tryptophan hydroxylase, all three nitric oxide synthetase (NOS) isoforms, and glyceryl-ether monooxygenase. BH4 deficiency can result from defects in the genes encoding the enzymes involved in BH4 synthesis (GTP cyclohydrolase 1 (GTP-CH 1), 6-pyruvoyl-tetrahydropterin synthase (PTPS) and sepiapterin reductase (SR)) or BH4 regeneration (dihydropteridine reductase (DHPR) and pterin-4-carbinolamine dehydratase (PCD, also called 4a-carbinolamine dehydratase)). In addition to elevated blood phenylalanine levels (HPA), patients with defects in BH4 metabolism can suffer progressive neurologic deterioration due to decreased production of the neurotransmitters dopamine, epinephrine, norepinephrine and serotonin.

The BH4 stable dosage forms described herein can be used to treat, ameliorate or prevent BH4 deficiency associated with deficiency in or reduced activity of any one or any combination of the enzymes involved in BH4 synthesis or recycling—GTP-CH 1, PTPS, SR, DHPR and PCD. For example, the BH4 stable dosage forms can be used to treat, ameliorate or prevent hyperphenylalanemia due to BH4 deficiency and associated with deficiency in or reduced activity of any one or any combination of the aforementioned enzymes. The BH4 stable dosage forms can also be used to treat, ameliorate or prevent hyperphenylalanemia due to phenylketonuria. In an embodiment, the BH4 stable dosage forms can be administered in conjunction with a low phenylalanine diet; with the neurotransmitter precursors L-dopa, carbidopa and/or serotonin; with folinic acid (leucovorin) or a salt form of folinate (e.g., calcium folinate), e.g., in the case of DHPR deficiency; or with any combinations thereof.

Suitable subjects for treatment with the stable dosage forms described herein include subjects with an elevated plasma Phe concentration in the absence of the therapeutic, e.g., greater than about 180 uM, greater than about 200 uM, greater than about 300 uM, greater than about 400 uM, greater than about 500 uM, greater than about 600 uM, greater than about 800 uM, greater than about 1,000 uM, greater than about 1,200 uM, greater than about 1,400 uM, greater than about 1,600 uM, or greater than about 1,800 uM. Mild PKU is generally classified as plasma Phe concentrations of up to about 600 uM, moderate PKU as plasma Phe concentrations of between about 600 uM and about 1,200 uM, and classic or severe PKU as plasma Phe concentrations that are greater than about 1,200 uM. Treatment with the dosage form alone or with a protein-restricted diet can decrease the plasma phenylalanine concentration of a subject to less than about 600 uM, less than about 500 uM, less than about 400 uM, less than about 350 uM, less than about 300 uM, less than about 250 uM, less than about 200 uM, less than about 150 uM, or less than about 100 uM.

Other suitable subjects include subjects diagnosed as having a reduced phenylalanine hydroxylase (PAH) activity. Reduced PAH activity may result from a mutation in the PAH enzyme, for example, a mutation in the catalytic domain of PAH or one or more mutations selected from the group consisting of F39L, L48S, 165T, R68S, A104D, S110C, D129G, E178G, V190A, P211T, R241C, R261Q, A300S, L308F, A313T, K320N, A373T, V388M E390G, A395P, P407S, and Y414C.

Further, other suitable subjects can include pregnant females, females of child-bearing age who are contemplating pregnancy, infants between 0 and 3 years of age (e.g., 0-2, 0-1.5 or 0-1 year old), and subjects diagnosed as being unresponsive within 24 hours to a single-dose BH4 loading test or a multiple dose loading test, such as a 4-dose or 7-day loading test. Exemplary patient populations and exemplary BH4 loading tests are described in WO 2005/049000, which is incorporated herein by reference in its entirety.

U.S. Pat. Nos. 4,752,573; 4,758,571; 4,774,244; 4,920,122; 5,753,656; 5,922,713; 5,874,433; 5,945,452; 6,274,581; 6,410,535; 6,441,038; and 6,544,994; and U.S. Application Publication Nos. US 2002/0187958; US 2002/0106645; US 2002/0076782; and US 2003/0032616 (each incorporated herein by reference in its entirety), each describe methods of administering BH4 compositions for non-PKU treatments. Each of these patent documents is incorporated herein by reference as teaching methods of administering BH4 compositions known to those of skill in the art, which can be adapted for the therapeutic method described herein, as well as teaching related conditions that can also be treated by applying the present disclosure.

While individual needs may vary, determination of the optimal range of the effective amount of the active ingredient and the optimal administration regimen is within the skill of an ordinary artisan. Exemplary dosages of BH4 or a BH4-related compound can range from about 1 to about 30 mg/kg body weight per day, which may amount to about 5 (1 mg/kg×5 kg body weight) to 3,000 mg/day (30 mg/kg×100 kg body weight). Dosages of BH4 or a BH4-related compound can also range from about 2 to about 20 mg/kg/day. One embodiment is directed to daily administration of a BH4 capsule dosage form for a continuous period of time. For hyperphenylalanemia, however, it may be desirable to cease the BH4 therapy when the symptoms of Phe levels are reduced to below a certain threshold level. Of course, the BH4 therapy can be reinitiated in the event that Phe levels rise again. Appropriate dosages can be ascertained through use of established assays for determining blood levels of Phe in conjunction with relevant dose response data.

In an embodiment, the method of the present disclosure provides to a patient a daily dose of between about 10 mg/kg and about 20 mg/kg of BH4 or a BH4-related compound. Of course, one skilled in the art can adjust (i.e., increase or decrease) the dose depending on the efficacy achieved by the administration. The daily dose can be administered in a single dose or alternatively can be administered in multiple doses at conveniently spaced intervals. In exemplary embodiments, the mg/kg daily dose of BH4 or a BH4-related compound can be 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 55, 60, 65, 70 or more mg/kg body weight per day.

The BH4 stable dosage forms described herein can also be used to treat subjects suffering from conditions or disorders that would benefit from enhancement of nitric oxide synthase (NOS) activity and subjects suffering from vascular diseases, ischemic or inflammatory diseases, or insulin resistance. Unless expressly indicated otherwise, the term "nitric oxide synthase" or "NOS" refers to all the isoforms of NOS, i.e., endothelial nitric oxide synthase (eNOS), neuronal nitric oxide synthase (nNOS), and inducible nitric oxide synthase (iNOS). The BH4 treatment can, e.g., alleviate a deficiency in NOS activity or can, e.g., provide an increase in NOS activity over normal levels.

Nitric oxide is constitutively produced by vascular endothelial cells, where it plays a key physiological role in the regulation of blood pressure and vascular tone. A deficiency in nitric oxide bioactivity may be involved in the pathogenesis of vascular dysfunctions, including coronary artery disease, atherosclerosis of any arteries, including coronary, carotid, cerebral and peripheral vascular arteries, ischemia-reperfusion injury, hypertension, diabetes, diabetic vasculopathy, cardiovascular disease, peripheral vascular disease, and neurodegenerative conditions stemming from ischemia and/or inflammation, such as stroke. Such pathogenesis includes damaged endothelium, insufficient oxygen flow to organs and tissues, elevated systemic vascular resistance (high blood pressure), vascular smooth muscle proliferation, progression of vascular stenosis (narrowing) and inflammation. In an embodiment, the BH4 capsule dosage forms described herein can be used to treat any of the aforementioned conditions.

Enhancement of nitric oxide synthase activity may also result in reduction of superoxide levels, increased insulin sensitivity, and reduction in vascular dysfunction associated with insulin resistance, as described in U.S. Pat. No. 6,410,535, which is incorporated herein by reference in its entirety.

Thus, the BH4 dosage forms described herein can also be used to treat diabetes (type I and type II), hyperinsulinemia, and insulin resistance. Diseases having vascular dysfunction associated with insulin resistance include those caused by insulin resistance or aggravated by insulin resistance, or those for which cure is retarded by insulin resistance, such as hypertension, hyperlipidemia, arteriosclerosis, coronary vasoconstrictive angina, effort angina, cerebrovascular constrictive lesion, cerebrovascular insufficiency, cerebral vasospasm, peripheral circulation disorder, coronary arteriorestenosis following percutaneous transluminal coronary angioplasty (PTCA) or coronary artery bypass grafting (CABG), obesity, insulin-independent diabetes, hyperinsulinemia, lipid metabolism abnormality, coronary arteriosclerotic heart diseases, and like conditions that are associated with insulin resistance.

Moreover, the BH4 dosage forms described herein can be used to treat drug-induced renal injury. The BH4 treatment can recover the functions of endothelial cells and normalize the functions of NOS to provide renal protective effects. Clinical states of drug-induced renal injury are typically classified into acute renal failure and chronic renal failure, as described in U.S. Pat. No. 6,288,067, which is incorporated herein by reference in its entirety.

When administered to patients susceptible to or suffering from any of the aforementioned disorders, BH4 or a BH4-related compound can treat or prevent these disorders by activating the functions of NOS, increasing NO production, and suppressing the production of active oxygen species (e.g., superoxide), to improve disorders of vascular endothelial cells.

A subject suffering from a deficiency in nitric oxide synthase (NOS) activity may benefit from co-treatment with BH4 or a BH4-related compounds, and folic acids, folates, folate precursors, or folate derivatives. Accordingly, in one embodiment, provided herein is use of stable capsule dosage forms comprising BH4 or a BH4-related compounds and a folic acid, folate, folate precursor, or folate derivative for treating, ameliorating or preventing cardiovascular or neurological disorders by modulation of the activity of a nitric oxide synthase (NOS). Modulation of the activity of an NOS can, e.g., reduce superoxide ($O_2$.) production, enhance nitric oxide (NO) synthesis, and influence NO levels. U.S. Pat. Nos. 6,995,158, 6,544,994; and 6,011,040, each of which is incorporated herein by reference in its entirety, describe the use of BH4 and a folic acid or folate compound to modulate NOS activity.

Non-limiting examples of folic acids, folates, folate precursors, and folate derivatives that can be used in the present disclosure include folic acid (pteroylmonoglutamate), dihydrofolic acid, dihydrofolates, tetrahydrofolic acid, 5-methyltetrahydrofolic acid, 5,10-methylenetetrahydrofolic acid, 5,10-methenyltetrahydrofolic acid, 5,10-formiminotetrahydrofolic acid, 5-formyltetrahydrofolic acid (leucovorin), 10-formyltetrahydrofolic acid, 10-methyltetrahydrofolic acid, tetrahydrofolates, folylpolyglutamates, compounds in which the pyrazine ring of the pterin moiety of folic acid or of the folylpolyglutamates is reduced to give dihydrofolates or tetrahydrofolates, derivatives of all the preceding compounds in which the N-5 or N-10 position carries one carbon unit at various levels of oxidation, pharmaceutically acceptable salts of all the preceding compounds, and combinations thereof. In an embodiment, the BH4-containing formulation comprises an initial amount of a folic acid, a folate, a folate precursor or a folate derivative (e.g., folic acid or 5-methyltetrahydrofolate) in a range from about 0.0005% to about 5%, or to about 3%, or to about 1%, or to about 0.5%, or to about 0.1%, or to about 0.05% by weight of the formulation.

Exemplary tetrahydrofolic acids and tetrahydrofolates include 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid, (6S)-tetrahydrofolic acid, and pharmaceutically acceptable salts thereof. Exemplary salts of all the folic acid and folate compounds described herein include sodium, potassium, calcium, and ammonium salts thereof.

The pharmaceutical formulation comprising BH4 or a BH4-related compound and a folic acid, folate, folate precursor, or folate derivative, can further comprise one or more other active or adjuvant substances. In one embodiment, the one or more other active or adjuvant substances include arginine (e.g., L-arginine). L-arginine is a precursor of endogenous nitric oxide (NO), a potent vasodilator acting via the intracellular second messenger cGMP. L-arginine induces peripheral vasodilation and inhibits platelet aggregation due to increased NO production. A lack of NO production has been linked to pathological conditions, including cardiovascular disorders (e.g., atherosclerosis), septic shock, inflammation and infection, and brain damage in stroke and neurological disorders. In an embodiment, the formulation comprises BH4 or a BH4-related compound, a folic acid or a folate (which can also be a folate precursor or a folate derivative), and arginine each in a unit dosage from about 0.1 mg to about 250 mg. In another embodiment, the weight ratio of BH4 or a BH4-related compound to a folic acid or a folate to arginine ranges from about 1:10:10 to about 10:1:1.

In another embodiment, the pharmaceutical formulation comprising BH4 or a BH4-related compound can be used to treat or ameliorate autism. In a particular embodiment, the BH4 or BH4-related compound is BH4 dihydrochloride. In a particular embodiment, BH4 dihydrochloride can be administered to children suffering from autism. In particular embodiment, the child is about 0-18 years old, 1-18 years old, about 2-18 years old, about 3-18 years old, about 3-17 years old, about 3-16 years old, about 3-15 years old, about 3-14 years old, about 3-13 years old, about 3-12 years old, about 3-11 years old, about 3-10 years old, about 3-9 years old, about 3-8 years old, about 3-7 years old, or about 3-6 years old. In a particular embodiment, the is administered to a subject during childhood and adulthood. In a particular embodiment, the formulation can be administered at a dosage of about 5-50 mg/kg/day. In a particular embodiment, the formulation can be administered at a dosage of about 5 mg/kg/day, or about 7.5 mg/kg/day, or about 10 mg/kg/day, or about 10.5 mg/kg/day, or about 11 mg/kg/day, or about 11.5 mg/kg/day, or about 12 mg/kg/day, or about 12.5 mg/kg/day, or about 13 mg/kg/day, or about 13.5 mg/kg/day, or about 14 mg/kg/day, or about 14.5 mg/kg/day, or about 15 mg/kg/day, or about 15.5 mg/kg/day, or about 16 mg/kg/day, or about 16.5 mg/kg/day, or about 17 mg/kg/day, or about 17.5 mg/kg/day, or about 18 mg/kg/day, or about 18.5 mg/kg/day, or about 19 mg/kg/day, or about 19.5 mg/kg/day, or about 20 mg/kg/day. In another embodiment, the pharmaceutical formulation comprising BH4 or a BH4-related compound can be used to treat or ameliorate autism at a dosage of 25 mg/kg/day or more.

It is understood that the suitable dose will depend upon various factors, such as the age, health, weight, and diet of the recipient, the kind of concurrent treatment, if any, the frequency of treatment, and the nature of the effect desired (e.g., the amount of decrease in plasma Phe concentration desired). The frequency of dosing also depends on the pharmacodynamic effects of a BH4 dosage form. For example, if the pharmacological effects of a single dose of a BH4 capsule dosage form last for about 24 hours, the BH4 capsule dosage form can be administered once daily. Alternatively, a BH4 dosage form can be administered two or more times a day at appropriate time intervals in cases where multiple daily administrations to a particular subject are deemed to be more effective for treating, ameliorating or preventing a particular BH4-responsive condition. One or more BH4 doses can be administered in a particular time of administration. For example, 1 BH4 dosage can be taken orally per day. As another example, 2 BH4 doses can be taken orally per day—e.g., 2 capsules or sachets once daily or 1 capsule or sachet twice daily. As yet another example, 3 BH4 doses can be taken orally per day—e.g., 3 capsules or sachets once daily, 2 capsules or sachets and 1 capsule or sachet at two different times, or 1 capsule or sachet thrice daily. As a further example, 4 BH4 doses can be taken orally per day—e.g., 4 capsules or sachets once daily, 2 capsules or sachets twice daily, 2 capsules or sachets and 2×1 capsule or sachets at three different times, or 1 capsule or sachet four times daily. As still another example, 6 BH4 doses can be taken orally per day—e.g., 6 capsules or sachets once daily, 3 capsules or sachets twice daily, 4 capsules or sachets and 2 capsules or sachets at two different times, or 2 capsules or sachets thrice daily. The desired dosage of the active ingredient, BH4 or a BH4-related compound, in a stable dosage form and the frequency of administration of the dosage form can be tailored to the individual subject and the particular BH4-responsive condition(s) being treated, as is understood and determinable by one of skill in the art, without undue experimentation. For example, a standard dose can be adjusted according to the facts and circumstances of a particular patient, e.g., reduction of the dose if the patient has a low body weight.

In addition, the frequency of BH4 dosing will depend on the pharmacokinetic parameters of the active ingredient and the route/mode of administration. The optimal features of a BH4 capsule or sachet dosage form can be determined by one of skill in the art depending on various factors, such as the route of administration and the desired dosage. See, e.g., Remington's Pharmaceutical Sciences, 18th Ed., pp. 1435-1712, Mack Publishing Co. (Easton, Pa., 1990), which is incorporated herein by reference. Depending on the route/mode of administration, a suitable dose can be calculated according to body weight, body surface areas or organ size. Further refinement of the calculations for determining the appropriate treatment dose is routinely made by those of ordinary skill in the art without undue experimentation, including in light of the dosage information and assays disclosed herein as well as the pharmacokinetic data observed in animals or human clinical trials.

The final dosage regimen will be determined by the attending physician, considering factors that may affect the action of the drug, e.g., the drug's specific activity, the severity of the damage, the responsiveness of the patient, the age, condition, body weight, sex and diet of the patient, the severity of any infection, the time and frequency of administration, and other clinical factors. As studies are conducted, further information will emerge regarding appropriate dosage levels and duration of treatment for specific diseases and conditions.

Combination Therapy

In one embodiment, the BH4 dosage forms described herein can be used in combination with one or more other therapeutic agents. In such combination therapy, administration of the BH4 dosage forms can be concurrent with or can precede or follow the administration of a second therapeutic agent, e.g., by intervals ranging from minutes to hours. BH4 or a BH4-related compound and the other therapeutic agent(s) can exert their pharmacological effects at overlapping or non-overlapping time periods. The disclosure encompasses the use of one or more additional therapeutic agents in the preparation of a pharmaceutical composition for use with BH4 or a BH4-related compound. The composition containing the additional therapeutic agent(s) can also contain BH4 or a BH4-related compound or can be distinct from the capsule formulation containing BH4 or a BH4-related compound.

Tetrahydrobiopterin therapy can be combined with dietary protein restriction to effect a therapeutic outcome in patients with various forms of hyperphenylalaninemia (HPA). For example, a subject can be administered a BH4 dosage form and a low phenylalanine medical protein composition in a combined amount effective to produce the desired therapeutic outcome, i.e., a lowering of plasma Phe concentration and/or the ability to tolerate greater amounts of Phe/protein intake without producing a concomitant increase in plasma Phe concentrations. The process can involve administering the BH4 dosage form and the dietary protein therapeutic composition at about the same time. This can be achieved by administering a single dosage form, or the dietary protein (supplement or normal protein meal) can be taken at about the same time as the BH4 dosage form.

Alternatively, the BH4 treatment can precede or follow the dietary protein therapy by intervals ranging from minutes to hours. The protein composition and the BH4 dosage form can be administered separately such that the BH4 will still be able to exert an advantageous effect on the patient. For example, the BH4 dosage form can be administered within about 1-6 hours (before or after) of the dietary protein intake. In a more specific example, the delay time between BH4 and dietary protein administrations can be about one hour. In one embodiment, the BH4 therapy is a continuous therapy wherein a daily dose of BH4 is administered to the patient continuously. In another embodiment, e.g., in pregnant women having only the milder forms of PKU or HPA, the BH4 therapy is only continued for as long as the woman is pregnant and/or breast feeding.

In another embodiment, the therapeutic method provided herein is a combination therapy that administers BH4 or a BH4-related compound and a composition that specifically targets one or more of the symptoms of HPA. For example, the deficit in tyrosine associated with HPA results in a deficiency in the neurotransmitters dopamine and serotonin. Thus, a BH4 stable dosage form can be administered in combination with the neurotransmitter precursors L-dopa, carbidopa and/or 5-hydroxytryptophan, with or without dietary protein therapy, to correct defects that result from decreased amounts of tyrosine in the body.

In another embodiment, the therapeutic method provided herein is a combination therapy that administers BH4 or a BH4-related compound and a composition that specifically targets one or more of the symptoms of autism. For example, medications for depression, anxiety, ADD/ADHD, mood stabilization, and Alzheimer's disease can be used in combination therapy with BH4 or a BH4-related compounds to treat or ameliorate the symptoms of autism. More specifically, for example stimulants (i.e., ADD/ADHD treatment) administered in conjunction with the BH4 or BH4-related compound to treat and ameliorate autism may include but are not limited to amphetamines, methylphenidate, pemoline, dextroamphetamines, dexmethylphenidate, methylphenidate, and combinations thereof; non-stimulants (i.e., ADD/ADHD treatment) administered in conjunction with the BH4 or BH4-related compound to treat and ameliorate autism may include but is not limited to atomoxetine; antidepressants and antianxiety medications administered in conjunction with the BH4 or BH4-related compound to treat and ameliorate autism may include but are not limited to clomipramine, buspirone, buspirone, fluvoxamine, paroxetine, fluoxetine, nefazodone, doxepin, imipramine, bupropion, sertraline, and combinations thereof; mood stabilizing medications administered in conjunction with the BH4 or BH4-related compound to treat and ameliorate autism may include but are not limited to lithium citrate, valproic acid, lithium carbonate, carbamazepine, and combinations thereof; and an Alzheimer's medication administered in conjunction with the BH4 or BH4-related compound to treat and ameliorate autism may include but is not limited to memantine HCl.

In addition, gene therapy with phenylalanine hydroxylase (PAH) (Christensen et al., *Mol. Genetics. Metabol.*, 76: 313-318 (2002); Christensen et al., *Gene Therapy*, 7: 1971-1978 (2000)) or phenylalanine ammonia lyase (PAL) (Liu et al., *Arts. Cells. Blood. Subs. and Immob. Biotech.*, 30: 243-257 (2002)) can be employed. Such gene therapy techniques can be used in combination with BH4 therapy and/or dietary protein restriction. In other combination therapies, phenylase can be provided as an injectable enzyme to further lower Phe concentrations in the patient. Because administration of phenylase would not generate tyrosine (unlike administration of PAH), phenylase treatment would still result in tyrosine being an essential amino acid for such patients. Therefore, dietary supplementation with tyrosine may be desired for patients receiving phenylase in combination with BH4 therapy.

Representative Embodiments

The following representative embodiments of the disclosure are given merely to illustrate the disclosure and are not intended to limit the scope of the disclosure.

In one embodiment, provided herein is a stable capsule dosage form comprising a pharmaceutical formulation comprising an initial amount of (6R)-L-erythro-tetrahydrobiopterin dihydrochloride in the crystalline form designated polymorph B, and one or more pharmaceutically acceptable excipients, wherein the capsule has a shell that is essentially free of pullulan, and at least about 95%, at least about 96%, at least about 97%, at least about 98%, at least about 99%, or at least about 99.5% of the initial amount of the tetrahydrobiopterin dihydrochloride remains after the capsule dosage form is stored in a container at about 25° C. and about 60% relative humidity, or at about 40° C. and about 75% relative humidity, for a period of about 3 months, about 4 months, about 5 months, about 6 months, about 9 months, about 12 months (one year), about 18 months, about 24 months (two years), about 30 months, or about 36 months (three years).

In an embodiment, at least about 70%, at least about 75%, at least about 80%, at least about 85%, at least about 90%, at least about 95%, at least about 97%, or at least about 99% of the initial amount of the tetrahydrobiopterin dihydrochloride in the stable capsule dosage form dissolves within about 10 minutes, about 15 minutes, about 20 minutes, about 25 minutes, or about 30 minutes after the capsule dosage form has been stored in the container at about 25° C. and about 60% relative humidity, or at about 40° C. and about 75% relative humidity, for a period of about 3 months, about 4 months, about 5 months, about 6 months, about 9 months, about 12 months, about 18 months, about 24 months, about 30 months, or about 36 months, wherein the dissolution is determined according to U.S.P. Method II at 50 r.p.m. in 0.1 N hydrochloric acid maintained at 37° C.

In a particular embodiment, the container is a heat induction-sealed, screw cap high-density polyethylene (HDPE) bottle. In another embodiment, the HDPE bottle is sealed in a foil pouch. In another particular embodiment, the container is a foil blister pack. In an embodiment, the container contains a desiccant. In another embodiment, the container contains no desiccant.

In an embodiment, the initial amount of the tetrahydrobiopterin dihydrochloride in the capsule dosage form is in a range from about 100 mg to about 500 mg. In specific embodiments, the initial amount of the tetrahydrobiopterin dihydrochloride is about 100 mg, about 150 mg, about 160 mg, about 200 mg, about 250 mg, about 300 mg, about 350 mg, about 400 mg, about 450 mg, or about 500 mg per capsule.

In one embodiment, the shell of the capsule is made of or comprises one or more substances selected from the group consisting of cellulose derivatives; hydroxypropyl methylcellulose (HPMC); starch derivatives; carrageenans; acacia; gelatin; polyethylene glycol; homopolymers and copolymers formed from polyvinyl alcohol, acrylic acid, and methyl methacrylate; and combinations thereof. In a specific embodiment, the shell of the capsule is made of or comprises gelatin. In another specific embodiment, the shell of the capsule is made of or comprises hydroxypropyl methylcellulose.

In one embodiment, provided herein is a stable powder dosage comprising a pharmaceutical formulation comprising an initial amount of a BH4 or BH4-related compound in pre-blended, powder (i.e., crystalline) form, wherein the powder is pre-mixed and blended to be dissolved in solution. In a specific embodiment, the BH4 or BH4-related compound is (6R)-L-erythro-tetrahydrobiopterin dihydrochloride, designated polymorph B. In a specific embodiment, the pharmaceutical formulation comprises an additional one or more pharmaceutically acceptable excipients. In a specific embodiment, the pharmaceutical formulation comprises (6R)-L-erythro-tetrahydrobiopterin dihydrochloride, a sweetener, a flavoring agent, and a flavor enhancer.

In another specific embodiment, the pre-blended powder formulation comprises the BH4 or BH4-related compound, a sweetener, a flavoring agent, one or more fillers, and a flavor enhancer is a dry blend. In a specific embodiment, the BH4 or BH4-related compound is (6R)-L-erythro-tetrahydrobiopterin dihydrochloride. In certain embodiments, the formation is prepared by blending the fillers with the BH4 or BH4 compound and flavor enhancer in a blender to achieve a adequate mixture, further blending a portion of the blended mixture with acesulfame potassium or sucralose, a flavoring agent, and ascorbic acid and thereafter passing that mixture through a suitable sieve (e.g., 20 mesh sieve), and lastly blending the second mixture with the remainder of the first mixture until the blend is homogenous.

In a specific embodiment, the sweetener is acesulfam potassium, isomalt, Magna Sweet, maltitol, mannitol, sorbitol, sucralose, xylitol, alitmae, neohesperidin dihydrochalcone, trehalose, tagatose, neotame, saccharin and salts thereof, stevioside, erythritol, isomaltulose, polydextrose, luo han guo, monatin, cyclamate, osladine, sucrose, fructose, or glucose or combinations thereof. In a specific embodiment, the flavor enhancer is anhydrous citric acid, citric acid monohydrate, malic acid, tartic acid, sodium citrate, potassium citrate dehydrate, or sodium potassium tartate or combinations thereof. In a specific embodiment, the flavoring agent is a cherry, grape, orange, pink lemonade, raspberry, grape, lemon, orange, strawberry, tutti-frutti, tangerine, apple, watermelon, pineapple, banana, peach, kiwi, mango, mixed berry, raspberry lemonade, wild blackberry, blue raspberry, citrus, blueberry, lime, lemon lime, grapefruit, pomegranate, pear, or plum flavors or combinations thereof; and the sieve is a 20 mesh sieve.

In another specific embodiment, the pre-blended powder formulation comprises 6R)-L-erythro-tetrahydrobiopterin dihydrochloride (i.e., BH4 dihydrochloride), the flavor enhancer is citrate, the sweeteners is mannitol, the flavoring agent is orange, and an additional taste masking agent is sucralose.

In another embodiment, the powder dosage is packaged in a single chamber sachet or a dual chamber sachet. In a specific embodiment, the dual chamber sachet separates incompatible components. In a specific embodiment, the dual chamber sachet comprises one chamber that contains the active BH4 powder blend and a second chamber that contains the flavor blend. In a specific embodiment, the sachets comprise of an additional active agent for combination therapy.

In another embodiment, the sachets are sealed in Mylar foil pouches. In a specific embodiment, a desiccant is included in the sachets or in the foil pouches.

In another embodiment, the amount of the BH4 or BH4 compound in the sachet dosage form is in a range from about 100 mg to about 1300 mg (i.e., 1.3 g). In specific embodiments, the initial amount of the tetrahydrobiopterin dihydrochloride is about 100 mg, about 150 mg, about 160 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, or about 1300 mg per sachet.

In another embodiment, the sachets are filled with 600 mg or more, for example, of the BH4 or BH4-related compound powder blend wherein the unexpected flowability of the dry blend powder formulation allows for automated sachet filling.

In another embodiment, the final dosage strength after the active BH4 or BH4 compound from the sachet dosage is dissolved in an aqueous solution with the flavor blend is about 10 mg/mL. In specific embodiments, the final dosage strength is about 1 mg/mL, about 2 mg/mL, 3 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 12 mg/mL, about 13 mg/mL, about 14 mg/mL, about 15 mg/mL, or about 20 mg/mL.

In a further embodiment, the pharmaceutical formulations in the stable capsule and sachet dosage forms comprise one or more pharmaceutically acceptable excipients selected from the group consisting of ascorbic acid, silicon dioxide, mannitol, microcrystalline cellulose, crospovidone, povidone, stearyl fumaric acid, salt forms of stearyl fumarate, dicalcium phosphate, 5-methyltetrahydrofolate (5-MTHF), salt forms of 5-MTHF, and combinations thereof. In an embodiment, the one or more excipients include crospovidone and stearyl fumaric acid or a salt form of stearyl fumarate. In another embodiment, the one or more excipients further include ascorbic acid, silicon dioxide and mannitol.

In a particular embodiment, the pharmaceutical formulation in the stable capsule comprises an initial amount of (6R)-L-erythro-tetrahydrobiopterin dihydrochloride in a range from about 30% to about 60%, crospovidone from about 3% to about 6%, sodium stearyl fumarate from about 1% to about 3%, ascorbic acid from about 1% to about 10%, silicon dioxide from about 0.2% to about 2%, and mannitol from about 20% to about 50% by weight of the formulation.

In another particular embodiment, the pharmaceutical formulation comprises an initial amount of (6R)-L-erythro-BH4 dihydrochloride from about 40% to about 50%, ascorbic acid from about 40% to about 50%, crospovidone from about 3% to about 6%, sodium stearyl fumarate from about 1% to about 3%, silicon dioxide from about 0.2% to about 2%, and calcium salt of 5-methyltetrahydrofolate from about 0.01% to about 0.5% by weight of the formulation.

In another embodiment, the capsule and sachet formulations comprising (6R)-L-erythro-tetrahydrobiopterin dihydrochloride and one or more pharmaceutically acceptable excipients further comprise 5-hydroxytryptophan. In a particular embodiment, the formulation comprises an initial amount of 5-hydroxytryptophan in a range from about 20% to about 40% by weight of the formulation.

In yet another embodiment, the stable capsule and sachet dosage forms, including the pharmaceutical formulation therein, are made by a process that does not include adding liquid water. In an embodiment, the pharmaceutical formulation is made by mixing (6R)-L-erythro-tetrahydrobiopterin dihydrochloride and the one or more pharmaceutically acceptable excipients, without addition of liquid water. In an embodiment, the pharmaceutical formulation made without addition of liquid water is ground to a powder and packaged in dual chamber sachets. In certain embodiments each sachet is a single dose or multiple doses. In an embodiment, the pharmaceutical formulation made without addition of liquid water is the active ingredient of the stable BH4 capsules.

In a further embodiment, provided herein is a method of treating, ameliorating or preventing hyperphenylalanemia due to BH4 deficiency, comprising administering to a subject in need thereof a therapeutically effective amount of the BH4-containing stable capsule dosage and sachet forms described herein. In one embodiment, the capsule and sachet dosage forms are administered orally once daily. In another embodiment, the capsule and sachet dosage forms are administered orally twice daily.

In an embodiment, the stable capsule and sachet dosage forms are used to treat, ameliorate or prevent hyperphenylalanemia due to BH4 deficiency which is associated with deficiency in or reduced activity of any one or any combination of the enzymes GTP cyclohydrolase 1 (GTP-CH 1), 6-pyruvoyl-tetrahydropterin synthase (PTPS), sepiapterin reductase (SR), dihydropteridine reductase (DHPR), and pterin-4-carbinolamine dehydratase (PCD).

In a particular embodiment, the stable capsule and sachet dosage forms used to treat, ameliorate or prevent hyperphenylalanemia due to BH4 deficiency comprises a formulation comprising an initial amount of (6R)-L-erythro-tetrahydrobiopterin dihydrochloride in a range from about 30% to about 60%, crospovidone from about 3% to about 6%, sodium stearyl fumarate from about 1% to about 3%, ascorbic acid from about 1% to about 10%, silicon dioxide from about 0.2% to about 2%, and mannitol from about 20% to about 50% by weight of the formulation. In another embodiment, the formulation further comprises an initial amount of 5-hydroxytryptophan in a range from about 20% to about 40% by weight of the formulation.

In an embodiment, the stable capsule and sachet dosage forms are used to treat or ameliorate autism. In a particular embodiment, the stable capsule and sachet dosage is used to treat or ameliorate autism in children. In a particular embodiment, the stable capsule and sachet dosage is used to treat or ameliorate autism in adults. In a particular embodiment, the stable capsule and sachet dosage is used in a combination therapy with an additional medication(s) to treat or ameliorate autism.

EXAMPLES

The following examples are provided merely for illustration and are not intended to limit the scope of the disclosure.

Example 1

Dry Process for Making Capsule Dosage Forms

The active ingredient, (6R)-L-erythro-tetrahydrobiopterin dihydrochloride or a BH4-related compound, and all the excipients were separately pre-screened through an appropriate size mesh (e.g., #20 mesh screen). A powder blend for filling capsules was prepared by mixing the active ingredient with a glidant (e.g., colloidal silicon dioxide) using a high shear mixer until a homogenous mix was obtained. The mix was added to a suitable blender (e.g., V-blender) and blended with the remaining excipients (e.g., mannitol, ascorbic acid and crospovidone) except for the lubricant. A portion of the powder blend was removed from the blender and added to the lubricant (e.g., sodium stearyl fumarate) to obtain a pre-mix. The pre-mix was mixed in a suitable vessel and then passed through a screen with appropriate mesh opening (e.g., #20 mesh screen). The resulting material was returned to the blender for a final mixing. The desired amount of the final powder blend was filled into capsules (e.g., size 0 or size 00 gelatin or hydroxypropyl methylcellulose capsules) and the capsules were then closed with their cap.

Example 2

Stability of Various Capsule Dosage Forms

Certain embodiments of the capsule dosage forms of the present disclosure are illustrated in Table 1, with a comparison tablet dosage form. The (6R)-L-erythro-tetrahydrobiopterin dihydrochloride (BH4.2HCl) in all six capsule examples and the comparison tablet in Table 1 was in the form of polymorph B. Table 2 summarizes stability data for the Table 1 dosage forms in gelatin and HPMC capsules stored in heat induction-sealed, screw cap high density polyethylene (HDPE) bottles at 40° C. and about 75% relative humidity (accelerated stability conditions), and comparison data for tablets of Table 1 stored in heat induction-sealed, HDPE bottles at 40° C. and about 75% relative humidity or stored in foil blister cards under the same conditions. None of the gelatin capsule and HPMC capsule packagings in Table 2 contained a desiccant and the tablet foil blister cards also did not contain a desiccant, while the tablet HDPE bottles contained a desiccant. Table 2 demonstrates the ability of various capsule dosage forms to provide stable BH4 dihydrochloride over at least six months under the accelerated stability conditions.

Figure 2:
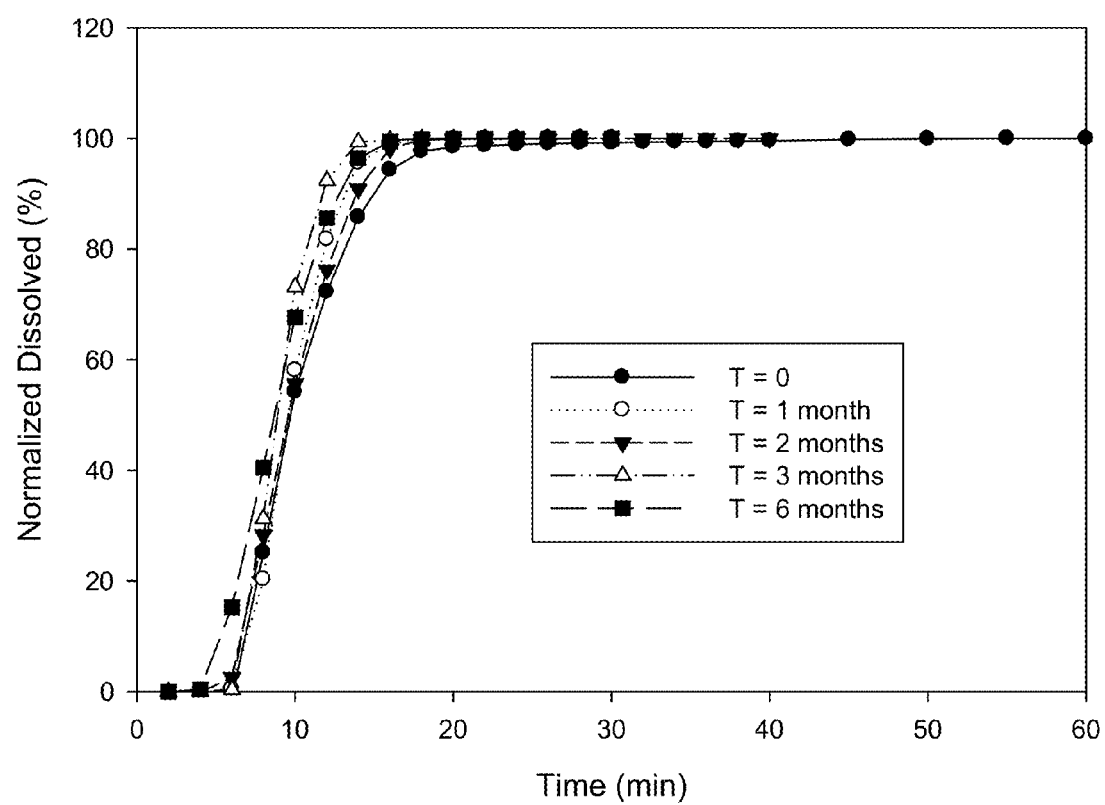
FIGS. 2 and 3 show dissolution profiles (the rate of dissolution of BH4 dihydrochloride from the solid dosage forms according to U.S.P. Method II at 50 r.p.m. in 0.1 N hydrochloric acid at 37° C.) after the HPMC and gelatin capsules have been stored for various periods of time at 40° C. and about 75% relative humidity. Polymorph B of BH4 dihydrochloride was used in both studies.
Figure 3:
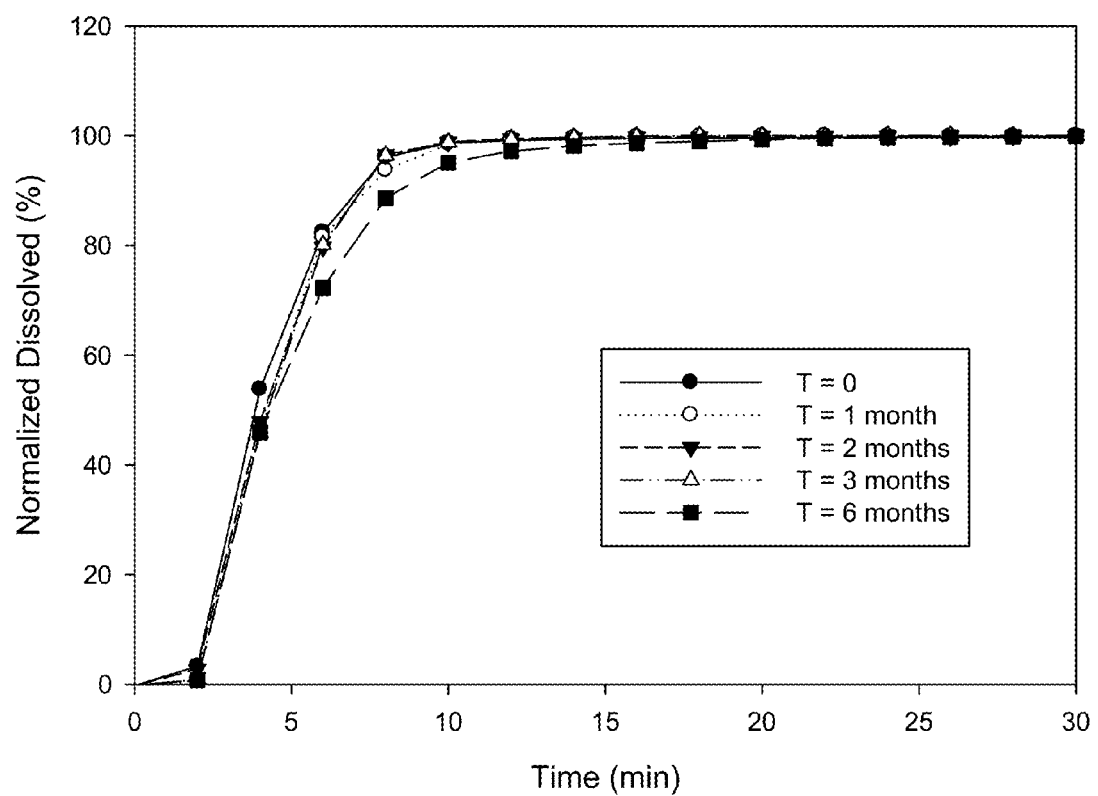

FIGS. 2 and 3 show the dissolution profiles (the rate of dissolution of BH4 dihydrochloride from the dosage form according to U.S.P. Method II at 50 r.p.m. in 0.1 N hydrochloric acid at 37° C.) after the capsule dosage forms have been stored at 40° C. and about 75% relative humidity. FIG. 2 shows the dissolution profile of BH4 dihydrochloride in the HPMC capsule dosage form of Example 3 in Table 1. FIG. 3 shows the dissolution profile of BH4 dihydrochloride in the gelatin capsule dosage form of Example 1 in Table 1. As evident from FIGS. 2 and 3, the dissolution rates of the BH4 dihydrochloride contained in the HPMC and gelatin capsules were maintained over the duration of the stability studies (six months), which is a factor in maintaining the pharmacokinetic properties (e.g., bioavailability) of BH4 over time.

Figure 4:
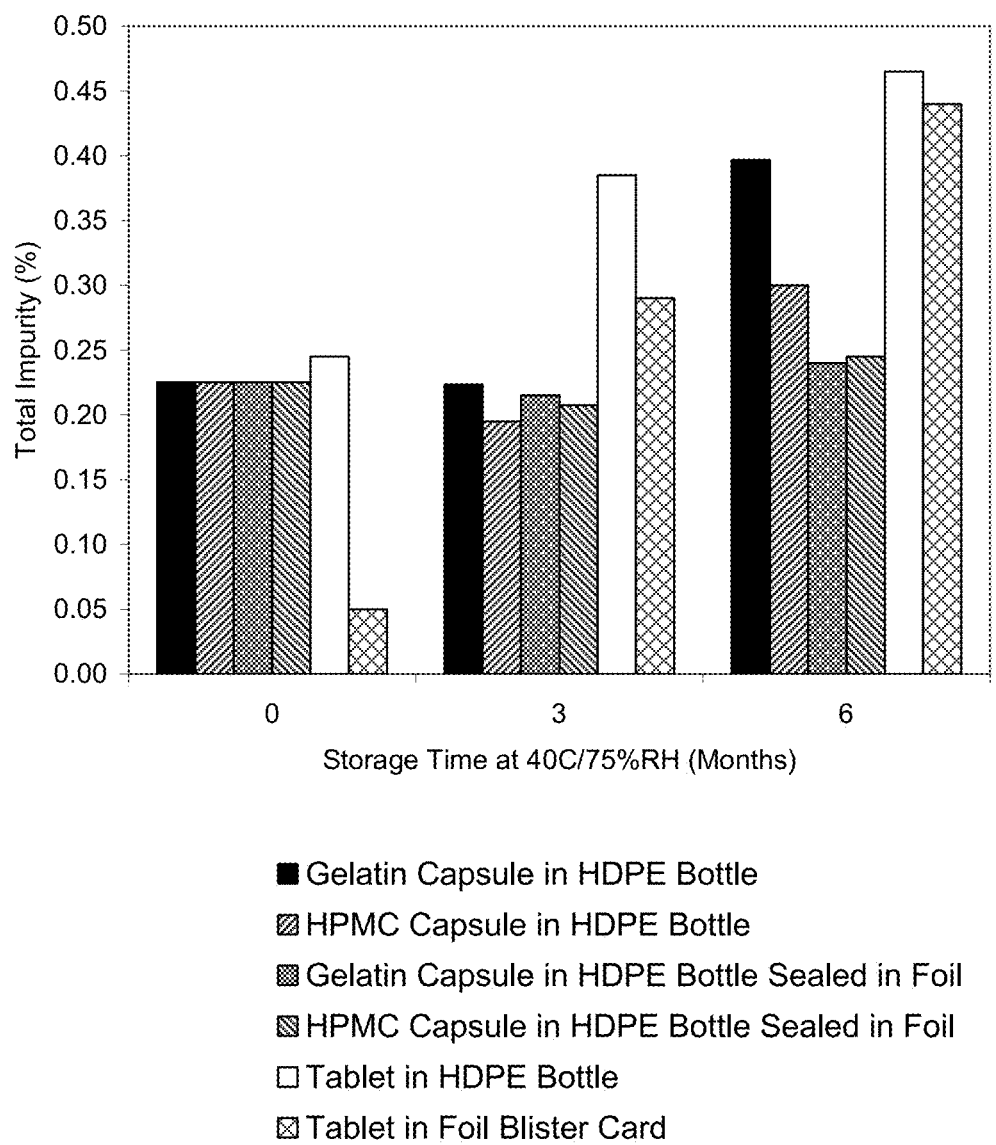
FIG. 4 compares the stability of BH4 capsules stored in high-density polyethylene (HDPE) bottles or HDPE bottles sealed in foil pouches at 40° C. and 75% relative humidity to the stability of BH4 tablets stored in HDPE bottles or foil blister cards under the same conditions. Polymorph B of BH4 dihydrochloride was used in all of these studies.

FIG. 4 compares the stability of BH4 capsule dosage forms that have been stored in heat induction-sealed HDPE bottles or heat induction-sealed HDPE bottles sealed in foil pouches at 40° C. and about 75% relative humidity, to the stability of BH4 tablets stored in heat induction-sealed HDPE bottles or foil blister cards under the same conditions (the stability data are given in Table 2). Storage in HDPE bottles sealed in foil pouches mimics storage in foil blister cards. None of the BH4 capsule packagings contained a desiccant and the tablet-containing foil blister cards also did not contain a desiccant, while the tablet-containing HDPE bottles contained a desiccant. The BH4 dihydrochloride in all of these stability studies of the capsules and tablets was in the form of polymorph B.

As demonstrated in Table 2 and FIG. 4, all of the BH4-containing HPMC and gelatin capsule dosage forms exhibited a very small percentage (0.4% or less) of total impurities after being stored without a desiccant for 6 months at 40° C. and about 75% relative humidity. As explained above, a capsule dosage form normally is not recommended for a hygroscopic, moisture-sensitive active ingredient such as BH4 dihydrochloride because BH4 dihydrochloride would be expected to absorb water from the material (e.g., gelatin or HPMC) in the capsule shell and consequently become labile to oxidation. For example, U.S. Pat. No. 4,917,885 teaches that when a hard gelatin capsule is stored under "a highly humid condition," the active ingredient therein can be "denatured due to the increased moisture inside the capsule," and thus "the quality of a gelatin-made hard capsule is unavoidably degraded in the lapse of time." Contrary to conventional wisdom, the capsule dosage forms provided herein comprise BH4 dihydrochloride that possesses unexpected stability over a prolonged period of time at elevated temperature and high humidity.

TABLE 1

BH4-Containing Formulations of Capsules and Tablets

| Ingredients wt % | Stable Capsule Lots | | | | | | Tablet |
| --- | --- | --- | --- | --- | --- | --- | --- |
| | Ex. 1 | Ex. 2 | Ex. 3 | Ex. 4 | Ex. 5 | Ex. 6 | |
| BH4•2HCl | 46.75 | 47.13 | 46.75 | 46.75 | 46.75 | 47.13 | 33.33 |
| Ascorbic Acid granular | 46.75 | 47.13 | 23.38 | 23.38 | 0.00 | 0.00 | 1.67 |
| Silicon Dioxide | 0.75 | 0.00 | 0.75 | 0.00 | 0.75 | 0.00 | 0.00 |
| Mannitol | 0.00 | 0.00 | 23.38 | 24.13 | 46.75 | 47.13 | 57.56 |
| Dicalcium phosphate | 0.00 | 0.00 | 0.00 | 0.00 | 0.00 | 0.00 | 2.18 |
| Crospovidone | 4.00 | 4.00 | 4.00 | 4.00 | 4.00 | 4.00 | 4.50 |
| Sodium | 1.75 | 1.75 | 1.75 | 1.75 | 1.75 | 1.75 | 0.75 |

TABLE 1-continued

BH4-Containing Formulations of Capsules and Tablets

| | Stable Capsule Lots | | | | | | |
|---|---|---|---|---|---|---|---|
| Ingredients wt % | Ex. 1 | Ex. 2 | Ex. 3 | Ex. 4 | Ex. 5 | Ex. 6 | Tablet |
| Stearyl Fumarate | | | | | | | |
| Riboflavin | 0.00 | 0.00 | 0.00 | 0.00 | 0.00 | 0.00 | 0.01 |
| Total | 100.0 | 100.0 | 100.0 | 100.0 | 100.0 | 100.0 | 100.0 |

TABLE 2

Stability of BH4 Capsules and Tablets Stored at 40° C. and about 75% Humidity

| | | | Total Impurity (%) | | |
|---|---|---|---|---|---|
| Lot No. | Capsule Type | Packaging | Initial | 3 months | 6 months |
| Ex. 1a | Gelatin capsule | HDPE bottle | 0.23 | 0.3 | 0.41 |
| Ex. 2a | Gelatin capsule | | 0.22 | 0.20 | 0.40 |
| Ex. 3a | HPMC capsule | | 0.18 | 0.22 | 0.29 |
| Ex. 3b | Gelatin capsule | | 0.19 | 0.20 | 0.39 |
| Ex. 4a | HPMC capsule | | 0.20 | 0.17 | 0.29 |
| Ex. 4b | Gelatin capsule | | 0.21 | 0.18 | 0.37 |
| Ex. 5a | HPMC capsule | | 0.26 | 0.20 | 0.32 |
| Ex. 5b | Gelatin capsule | | 0.24 | 0.25 | 0.42 |
| Ex. 6a | HPMC capsule | | 0.26 | 0.19 | 0.30 |
| Ex. 6b | Gelatin capsule | | 0.26 | 0.21 | 0.39 |
| Ex. 1b | Gelatin capsule | HDPE bottle | 0.23 | 0.30 | 0.26 |
| Ex. 2b | Gelatin capsule | sealed | 0.22 | 0.20 | 0.23 |
| Ex. 3c | HPMC capsule | in a foil pouch | 0.18 | 0.24 | 0.25 |
| Ex. 3d | Gelatin capsule | | 0.19 | 0.18 | 0.25 |
| Ex. 4c | HPMC capsule | | 0.20 | 0.17 | 0.23 |
| Ex. 4d | Gelatin capsule | | 0.21 | 0.18 | 0.23 |
| Ex. 5c | HPMC capsule | | 0.26 | 0.21 | 0.24 |
| Ex. 5d | Gelatin capsule | | 0.24 | 0.22 | 0.24 |
| Ex. 6c | HPMC capsule | | 0.26 | 0.21 | 0.26 |
| Ex. 6d | Gelatin capsule | | 0.26 | 0.21 | 0.23 |
| | Tablet | HDPE bottle | 0.25 | 0.39 | 0.47 |
| | Tablet | Foil blister card | 0.05 | 0.29 | 0.44 |

Example 3

HPMC Capsules Containing 160 mg BH4 Dihydrochloride

Table 3 describes the formulation of a stable capsule dosage form comprising 160 mg (6R)-L-erythro-tetrahydrobiopterin dihydrochloride in polymorphic form B, wherein the shell of the capsule comprises hydroxypropyl methylcellulose (HPMC).

TABLE 3

Formulation of HPMC Capsules Containing 160 mg BH4•2HCl

| Ingredients | Function | Weight % | mg/capsule |
|---|---|---|---|
| BH4 Dihydrochloride | Active | 50.00 | 160.0 |
| Mannitol | Diluent | 38.50 | 123.2 |
| Ascorbic Acid Granular | Antioxidant | 5.00 | 16.0 |
| Colloidal Silicon Dioxide | Glidant | 0.75 | 2.4 |
| Crospovidone | Disintegrant | 4.00 | 12.8 |
| Sodium Stearyl Fumarate | Lubricant | 1.75 | 5.6 |
| Total | | 100.00 | 320.0 |

The 160 mg BH4 capsule dosage form of Table 3 was prepared in the following manner. The active ingredient, (6R)-L-erythro-tetrahydrobiopterin dihydrochloride in polymorphic form B, and all the excipients were individually pre-screened through a #20 mesh screen. Pre-screened BH4 dihydrochloride and colloidal silicon dioxide were dry mixed in a plastic bag for 2 min by shaking. The mixture was screened through a #20 mesh screen, and then mixed at 600 rpm for 10 min using a high shear mixer. The resulting mixture was placed into a V-blender, and pre-screened ascorbic acid, crospovidone and mannitol were added. The mixture was mixed for 10 min. Pre-screened sodium stearyl fumarate was added, and the mixture was mixed for 5 min. The powder blend was passed through a #20 mesh screen. The resulting formulation, having the amounts of ingredients per capsule as shown in Table 3, was filled into size 0 HPMC capsules using a prefill filling system.

Figure 5:
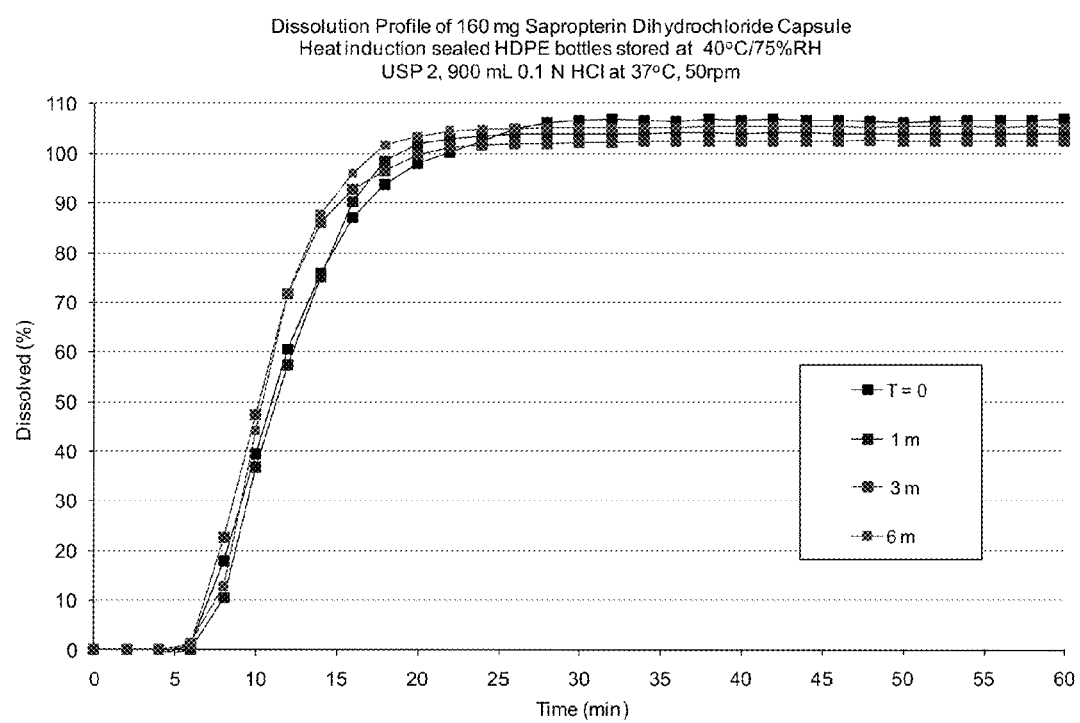
FIG. 5 depicts the dissolution profile of 160 mg BH4 dihydrochloride (polymorph B) contained in HPMC capsules after the capsules have been stored for 1 month at 25° C. and about 60% relative humidity, and alternatively at 40° C. and about 75% relative humidity.

HPMC capsules comprising the formulation of Table 3 were stored in heat induction-sealed, high-density polyethylene (HDPE) bottles containing no desiccant at 25° C. and about 60% relative humidity (RH) (normal stability conditions), and alternatively at 40° C. and about 75% relative humidity (accelerated stability conditions). Tables 4 and 5 show that the 160 mg BH4 HPMC capsules, after storage in HDPE bottles under normal and accelerated stability conditions for 3 months, exhibited no significant changes in capsule quality, potency and purity. For example, the capsules contained only 0.26% total impurities after 6 months of storage under accelerated stability conditions, i.e., only a 0.15% increase in level of total impurities. In addition, FIG. 5 demonstrates that the dissolution rate of the 160 mg BH4 dihydrochloride contained in the HPMC capsules, according to U.S.P. Method II, essentially did not change after the capsules were stored for 1, 3, and 6 months under accelerated stability conditions.

TABLE 4

Stability of 160 mg BH4 HPMC Capsules Stored at 25° C. and about 60% RH
HPMC Capsules Containing 160 mg BH4•2HCl
Heat induction-sealed HDPE bottles without desiccant
Storage Conditions: 25° C./60% relative humidity

| | Time Points (months) | | |
|---|---|---|---|
| Test | 0 | 1 | 3 |
| QUALITY | | | |
| Appearance of capsule | White to off-white capsule | White to off-white capsule | White to off-white capsule |
| Appearance of capsule content | Light yellow powder | Light yellow powder | Light yellow powder |
| POTENCY | | | |
| Assay by HPLC | 95.2% | 96.5% | 101.7% |
| PURITY | | | |
| Related Substances (HPLC) | | | |

TABLE 4-continued

Stability of 160 mg BH4 HPMC Capsules Stored at 25° C. and about 60% RH
HPMC Capsules Containing 160 mg BH4•2HCl
Heat induction-sealed HDPE bottles without desiccant
Storage Conditions: 25° C./60% relative humidity

| Test | Time Points (months) | | |
|---|---|---|---|
| | 0 | 1 | 3 |
| Biopterin | ND | ND | 0.02% |
| Dihydrobiopterin | ND | ND | 0.03% |
| R-Tetrahydrobiolumazine | 0.03% | 0.04% | 0.05% |
| S-Tetrahydrobiopterin | 0.03% | 0.02% | 0.04% |
| Tetrahydropterin | 0.05% | 0.04% | 0.06% |
| Individual Unidentified | ND | ND | ND |
| Total Unidentified | ND | ND | ND |
| Total | 0.11% | 0.10% | 0.20% |

ND = Not Detected
RRT = Relative Retention Time

TABLE 5

Stability of 160 mg BH4 HPMC Capsules Stored at 40° C. and about 75% RH
HPMC Capsules Containing 160 mg BH4•2HCl
Heat induction-sealed HDPE bottles without desiccant
Storage Conditions: 40° C./75% relative humidity

| Test | Time Points (months) | | |
|---|---|---|---|
| | 0 | 1 | 3 |
| QUALITY | | | |
| Appearance of capsule | White to off-white capsule | White to off-white capsule | White to off-white capsule |
| Appearance of capsule content | Light yellow powder | Light yellow powder | Light yellow powder |
| POTENCY | | | |
| Assay by HPLC | 95.2% | 99.0% | 98.7% |
| PURITY Related Substances (HPLC) | | | |
| Biopterin | ND | 0.02% | 0.05% |
| Dihydrobiopterin | ND | 0.02% | 0.06% |
| R-Tetrahydrobiolumazine | 0.03% | 0.04% | 0.06% |
| S-Tetrahydrobiopterin | 0.03% | 0.02% | 0.03% |
| Tetrahydropterin | 0.05% | ND | 0.06% |
| Individual Unidentified | ND | ND | ND |
| Total Unidentified | ND | ND | ND |
| Total | 0.11% | 0.10% | 0.26% |

ND = Not Detected
RRT = Relative Retention Time

Example 4

HPMC Capsules Containing 200 mg BH4 Dihydrochloride

Table 6 describes the formulation of a stable capsule dosage form comprising 200 mg (6R)-L-erythro-tetrahydrobiopterin dihydrochloride in polymorphic form B, wherein the shell of the capsule comprises hydroxypropyl methylcellulose (HPMC). This capsule dosage form was prepared in a manner similar to the preparative procedure described in Example 3.

TABLE 6

Formulation of HPMC Capsules Containing 200 mg BH4•2HCl

| Ingredients | Function | Weight % | mg/capsule |
|---|---|---|---|
| BH4 Dihydrochloride | Active | 50.00 | 200.0 |
| Mannitol | Diluent | 41.00 | 164.0 |
| Ascorbic Acid Fine Powder | Antioxidant | 2.50 | 10.0 |
| Colloidal Silicon Dioxide | Glidant | 0.75 | 3.0 |
| Crospovidone | Disintegrant | 4.00 | 16.0 |
| Sodium Stearyl Fumarate | Lubricant | 1.75 | 7.0 |
| Total | | 100.00 | 400.0 |

Figure 6:
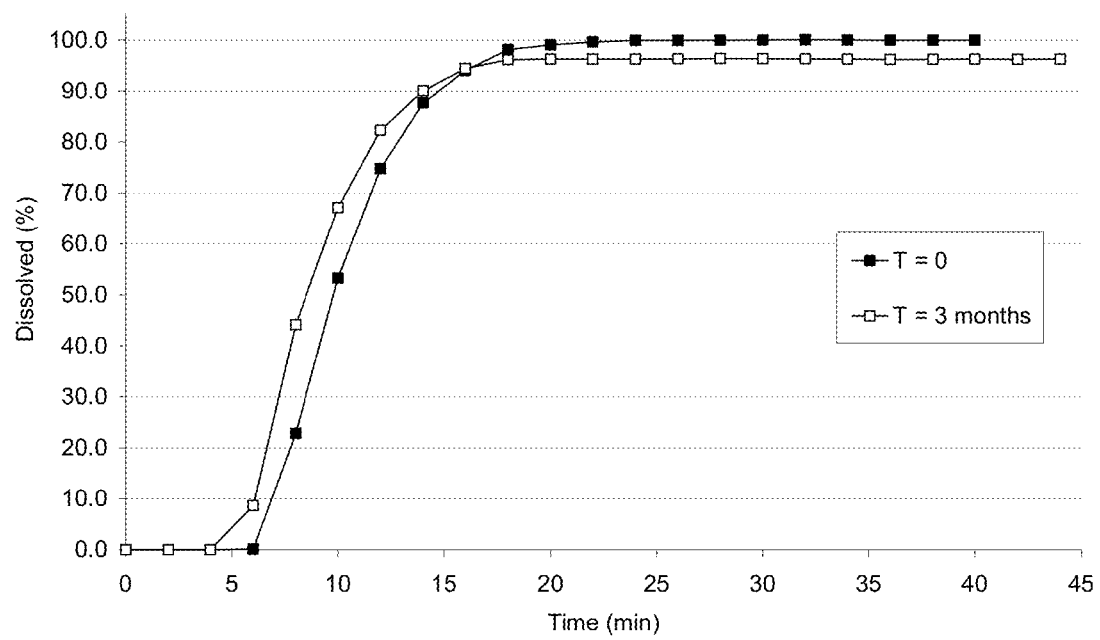
FIG. 6 illustrates the dissolution profile of 200 mg BH4 dihydrochloride (polymorph B) contained in HPMC capsules after the capsules have been stored for 3 months at 40° C. and about 75% relative humidity.

HPMC capsules comprising the formulation of Table 6 were stored in heat induction-sealed, HDPE bottles containing no desiccant at 40° C. and about 75% relative humidity. As evident from Table 7, the 200 mg BH4 HPMC capsules showed no significant changes in capsule quality, potency and purity after being stored in HDPE bottles under accelerated stability conditions for 6 months. For example, the capsules contained only 0.29% total impurities after 6 months of storage under accelerated stability conditions, which was only a 0.1% increase in level of total impurities. Further, FIG. 6 shows that the dissolution profile of the 200 mg BH4 dihydrochloride contained in the HPMC capsules, according to U.S.P. Method II, did not significantly change after the capsules were stored for 3 months under accelerated stability conditions.

TABLE 7

Stability of 200 mg BH4 HPMC Capsules Stored at 40° C. and about 75% RH
HPMC Capsules Containing 200 mg BH4•2HCl
Heat induction-sealed HDPE bottles without desiccant
Storage Conditions: 40° C./75% relative humidity

| Test | Time Points (months) | | |
|---|---|---|---|
| | 0 | 3 | 6 |
| QUALITY | | | |
| Appearance of capsule | White to off-white capsule | White to off-white capsule | White to off-white capsule |
| Appearance of capsule content | Light yellow powder | Light yellow powder | Light yellow |
| POTENCY | | | |
| Assay by HPLC | 92.7% | 93.1% | 91.2% |
| PURITY Related Substances (HPLC) | | | |
| Biopterin | ND | 0.03% | 0.06% |
| Dihydrobiopterin | 0.03% | 0.05% | 0.06% |
| R-Tetrahydrobiolumazine | 0.05% | 0.05% | 0.06% |
| S-Tetrahydrobiopterin | 0.04% | 0.03% | 0.03% |
| Tetrahydropterin | 0.06% | 0.03% | 0.07% |
| Individual Unidentified | 0.04% (RRT = 1.3) | 0.03% (RRT = 1.3) | 0.005% |
| Total Unidentified | ND | ND | 0.005% |
| Total | 0.18% | 0.19% | 0.29% |

ND = Not Detected
RRT = Relative Retention Time

The effect of storage with a desiccant on the stability of BH4 dihydrochloride was also evaluated. HPMC capsules comprising the formulation of Table 6 were stored in heat induction-sealed HDPE bottles containing varying amounts of silica gel desiccant for 6 months at 40° C. and about 75% relative humidity. As evident from Table 8, storage of the HPMC capsules in HDPE bottles containing increasing amounts of silica gel desiccant under accelerated stability conditions had no effect on the stability of BH4 dihydrochloride. With or without a desiccant, the 200 mg BH4 HPMC capsules contained a slightly higher amount of total impurities (0.29%) after 6 months of storage under accelerated stability conditions as they did prior to storage (0.18%).

conditions is detrimental to the physical stability of BH4 dihydrochloride; black specks were observed in the powder content of the capsules stored with 1 g and 2 g of desiccant after 6 months. Stability of the capsule stored without desiccant remains acceptable after 6 months of storage at 40° C./&5% RH. As evident from Table 10, the 200 mg BH4 HPMC capsules without desiccant showed insignificant

TABLE 8

Effect of Desiccant on Stability of BH4 HPMC Capsules Stored at 40° C./75% RH
HPMC Capsules Containing 200 mg BH4•2HCl
Heat induction-sealed HDPE bottles with varying amounts of silica gel desiccant
Storage Conditions: 40° C./75% relative humidity

| | | Time (month) and Amount (g) of Desiccant | | | | | |
|---|---|---|---|---|---|---|---|
| Test | 0 mo | 3 mo 0 g | 3 mo 1 g | 3 mo 2 g | 6 mo 0 g | 6 mo 1 g | 6 mo 2 g |
| | | | Quality | | | | |
| Appearance of capsule | White to off-white | White to off-white | White to off-white | White to off-white | White to off-white | White to off-white | White to off-white |
| Appearance of capsule content | Light yellow | Light yellow | Light yellow | Light yellow | Light yellow | Light yellow | Yellow |
| | | | Purity Related Substances (HPLC) | | | | |
| Biopterin | ND | 0.03% | 0.02% | 0.03% | 0.06% | 0.04% | 0.05% |
| Dihydrobiopterin | 0.03% | 0.05% | 0.06% | 0.07% | 0.06% | 0.07% | 0.07% |
| R-Tetrahydrobiolumazine | 0.05% | 0.05% | 0.06% | 0.04% | 0.06% | 0.05% | 0.05% |
| S-Tetrahydrobiopterin | 0.04% | 0.03% | 0.03% | 0.02% | 0.03% | 0.03% | 0.04% |
| Tetrahydropterin | 0.06% | 0.03% | 0.02% | 0.02% | 0.07% | 0.08% | 0.07% |
| Individual Unidentified | ND | ND | ND | ND | 0.005% | 0.005% (RRT = 0.5) 0.005% (RRT = 0.6) | 0.009% (RRT = 0.5) 0.006% (RRT = 0.6) |
| Total Unidentified | ND | ND | ND | ND | 0.005% | 0.01% | 0.015% |
| Total | 0.18% | 0.19% | 0.19% | 0.18% | 0.29% | 0.28% | 0.29% |

ND = Not Detected
RRT = Relative Retention Time

Figure 7:
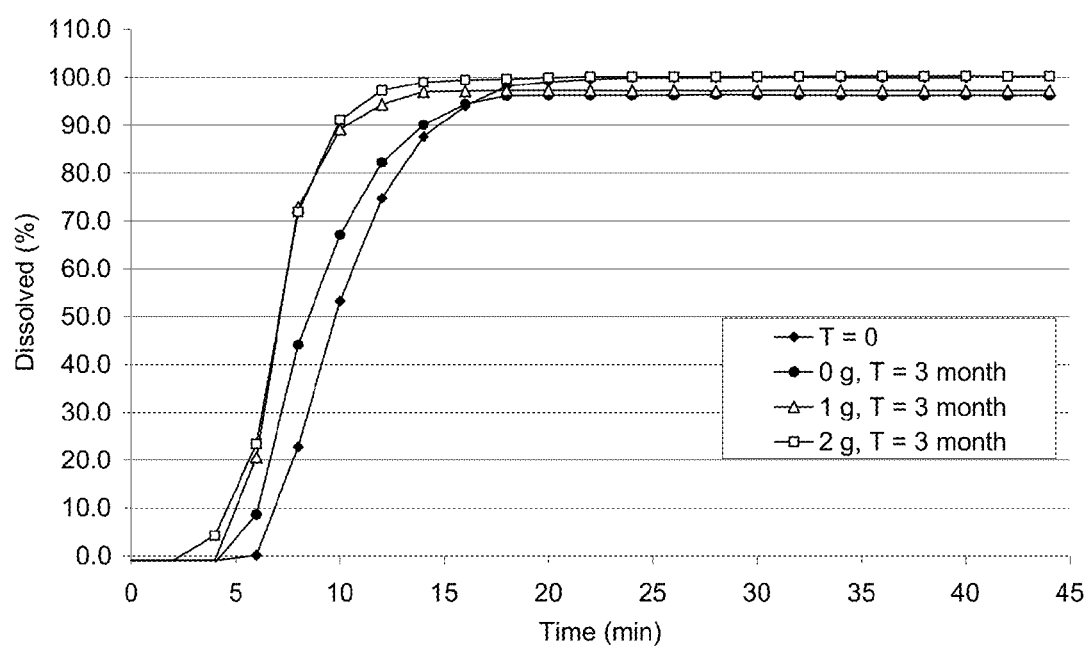
FIG. 7 displays the dissolution profile of 200 mg BH4 dihydrochloride (polymorph B) contained in HPMC capsules after the capsules have been stored in HDPE bottles containing varying amounts of silica gel desiccant for 3 months at 40° C. and about 75% relative humidity.
Figure 8:
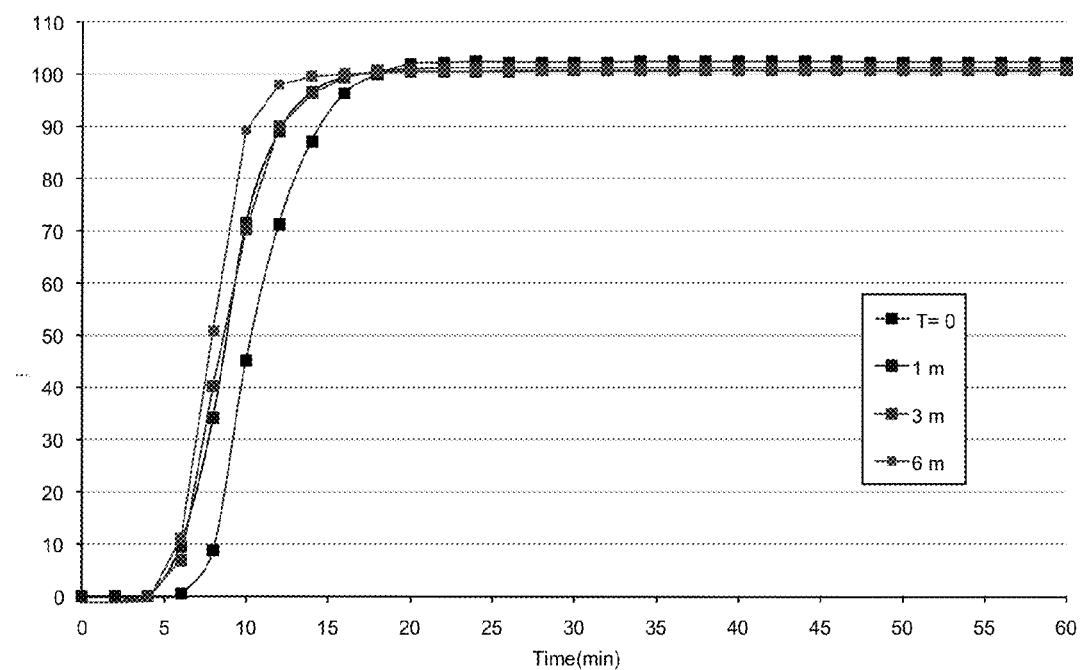
FIG. 8 shows the dissolution profile of 250 mg BH4 dihydrochloride (polymorph B) contained in HPMC capsules after the capsules have been stored for 1 month at 25° C. and about 60% relative humidity, and alternatively at 40° C. and about 75% relative humidity.

The dissolution profile of the 200 mg BH4 dihydrochloride contained in the HPMC capsules, according to U.S.P. Method II, slightly differed depending on whether the capsules were stored in HDPE bottles with or without a desiccant for 3 months under accelerated stability conditions. FIG. 7 shows that storage with silica gel desiccant slightly decreased the dissolution lag time of the BH4 dihydrochloride and slightly sped up its dissolution.

TABLE 9

HPMC Capsules Containing 200 mg BH4 Dihydrochloride with Sucralose

| Ingredients | Function | Weight % | mg/capsule |
|---|---|---|---|
| BH4 Dihydrochloride | Active | 50.00 | 200.0 |
| Mannitol | Diluent | 37.00 | 148.0 |
| Ascorbic Acid Fine Powder | Antioxidant | 2.50 | 10.0 |
| Colloidal Silicon Dioxide | Glidant | 0.75 | 3.0 |
| Sucralose | Sweetener | 4.00 | 16.0 |
| Crospovidone | Disintegrant | 4.00 | 16.0 |
| Sodium Stearyl Fumarate | Lubricant | 1.75 | 7.0 |
| Total | | 100.00 | 400.0 |

Figure 9:
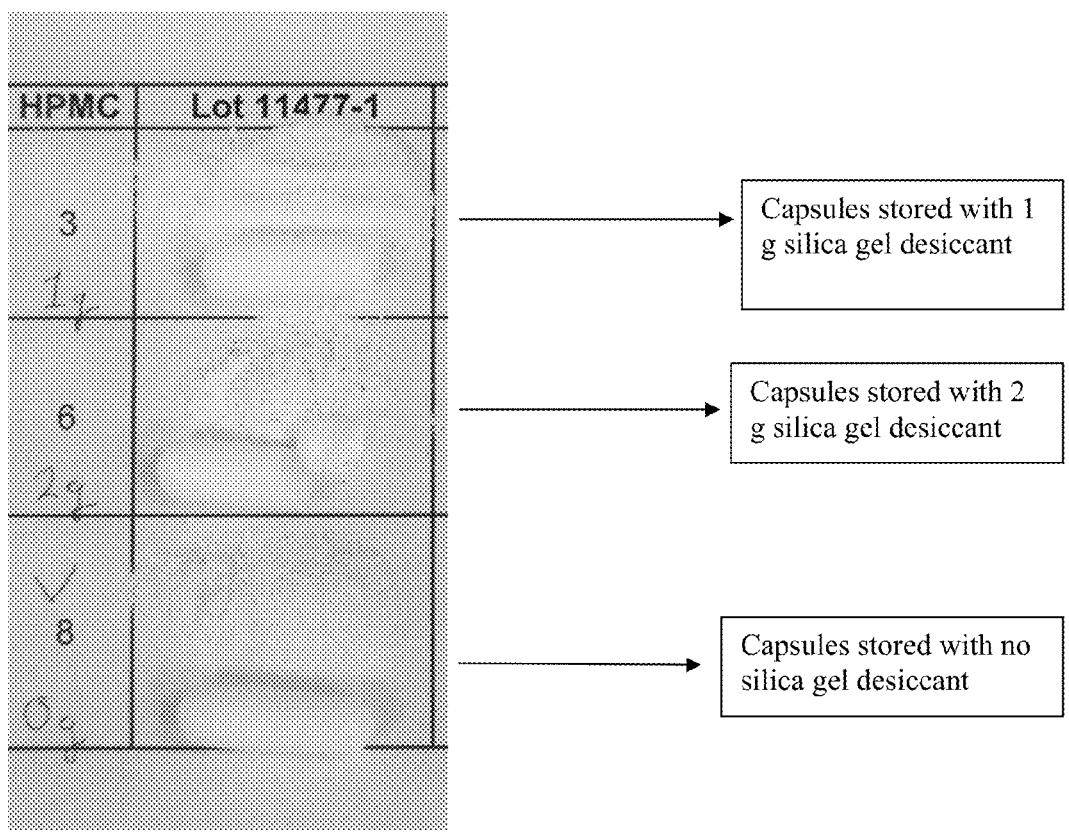
FIG. 9 shows the appearance of hydroxypropyl methylcellulose ("HPMC") capsule contents after 6 months of storage at 40° C. and 5% relative humidity ("RH").

HPMC capsules comprising the formulation of Table 9 were stored in heat induction-sealed, HDPE bottles with varying amounts of silica gel desiccant at 40° C. and about 75% relative humidity. As evident from FIG. 9, storage of the HPMC capsules in HDPE bottles containing increasing amounts of silica gel desiccant under accelerated stability change in capsule quality, potency and purity after being stored in HDPE bottles under accelerated stability conditions for 6 months. For example, the capsules contained only 0.29% total impurities after 6 months of storage under accelerated stability conditions, which was only about 0.1% increase in level of total impurities.

TABLE 10

Stability of BH4 HPMC Capsules (with sucralose) Stored at
40° C./75% RH
HPMC Capsules Containing 200 mg BH4•2HCl
Heat induction-sealed HDPE bottles without silica gel desiccant
Storage Conditions: 40° C./75% relative humidity

| | Time (month) | | |
|---|---|---|---|
| Test | 0 mo | 3 mo | 6 mo |
| | Quality | | |
| Appearance of capsule | White to off-white | White to off-white | White to off-white |
| Appearance of capsule content | Light yellow | Light yellow | Yellow |
| | Potency | | |
| BH4 | 95.1% | 92.2% | 94.1% |
| | Purity Related Substances (HPLC) | | |

TABLE 10-continued

Stability of BH4 HPMC Capsules (with sucralose) Stored at 40° C./75% RH
HPMC Capsules Containing 200 mg BH4•2HCl
Heat induction-sealed HDPE bottles without silica gel desiccant
Storage Conditions: 40° C./75% relative humidity

| Test | Time (month) | | |
|---|---|---|---|
| | 0 mo | 3 mo | 6 mo |
| Biopterin | ND | 0.03% | 0.06% |
| Dihydrobiopterin | 0.03% | 0.06% | 0.06% |
| R-Tetrahydrobiolumazine | 0.05% | 0.05% | 0.06% |
| S-Tetrahydrobiopterin | 0.04% | 0.02% | 0.03% |
| Tetrahydropterin | 0.06% | 0.03% | 0.07% |
| Individual Unidentified | ND | ND | 0.003% (RRT = 0.51) 0.005% (RRT = 0.63) |
| Total Unidentified | ND | ND | 0.008% |
| Total | 0.18% | 0.19% | 0.29% |

Example 5

HPMC Capsules Containing 250 mg BH4 Dihydrochloride

Table 11 describes the formulation of a stable capsule dosage form comprising 250 mg (6R)-L-erythro-tetrahydrobiopterin dihydrochloride in polymorphic form B, wherein the shell of the capsule comprises hydroxypropyl methylcellulose (HPMC). This capsule dosage form was prepared in a manner similar to the preparative procedure described in Example 3, wherein the order of addition of ingredients was BH4 dihydrochloride and silicon dioxide, followed by ascorbic acid and crospovidone, then followed by 5-methyltetrahydrofolate, and finally followed by sodium stearyl fumarate.

TABLE 11

Formulation of HPMC Capsules Containing 250 mg BH4•2HCl

| Ingredients | Function | Weight % | mg/capsule |
|---|---|---|---|
| BH4 Dihydrochloride | Active | 46.75 | 250.0 |
| Ascorbic Acid Granular | Antioxidant | 46.75 | 250.0 |
| Colloidal Silicon Dioxide | Glidant | 0.75 | 4.0 |
| Crospovidone | Disintegrant | 3.96 | 21.2 |
| Sodium Stearyl Fumarate | Lubricant | 1.75 | 9.4 |
| 5-Methyltetrahydrofolate, Calcium Salt | Dietary Supplement | 0.04 | 0.2 |
| Total | | 100.00 | 534.8 |

HPMC capsules comprising the formulation of Table 11 were stored in heat induction-sealed, high-density polyethylene (HDPE) bottles containing no desiccant at 25° C. and about 60% relative humidity (normal stability conditions), and alternatively at 40° C. and about 75% relative humidity (accelerated stability conditions). Tables 12 and 13 show that the 250 mg BH4 HPMC capsules, after storage in HDPE bottles under normal and accelerated stability conditions for 3 month, displayed no significant changes in capsule quality, potency and purity. For example, the capsules contained only 0.25% total impurities after 3 month of storage under normal stability conditions, which was only a 0.15% increase in level of total impurities, and the capsules contained only 0.0.3% total impurities after 3 month of storage under accelerated stability conditions, which was only an increase of 0.2% total impurities.

TABLE 12

Stability of 250 mg BH4 HPMC Capsules Stored at 25° C. and about 60% RH
HPMC Capsules Containing 250 mg BH4•2HCl Heat induction-sealed HDPE bottles without desiccant
Storage Conditions: 25° C./60% relative humidity

| Test | Time Points (months) | | |
|---|---|---|---|
| | 0 | 1 | 3 |
| QUALITY | | | |
| Appearance of capsule | White to off-white capsule | White to off-white capsule | White to off white capsule |
| Appearance of capsule content | Light yellow powder | Light yellow powder | Light yellow powder |
| POTENCY | | | |
| Assay by HPLC | 99.7% | 101.3% | 102.3% |
| PURITY Related Substances (HPLC) | | | |
| Biopterin | ND | 0.01% | 0.02% |
| Dihydrobiopterin | ND | 0.02% | 0.04% |
| R-Tetrahydrobiolumazine | 0.04% | 0.03% | 0.05% |
| S-Tetrahydrobiopterin | 0.03% | 0.02% | 0.04% |
| Tetrahydropterin | 0.03% | ND | 0.10% |
| Individual Unidentified | ND | 0.03% (RRT = 0.72) | ND |
| Total Unidentified | ND | 0.03% | ND |
| Total | 0.10% | 0.11% | 0.25% |

ND = Not Detected
RRT = Relative Retention Time

TABLE 13

Stability of 250 mg BH4 HPMC Capsules Stored at 40° C. and about 75% RH
HPMC Capsules Containing 250 mg BH4•2HCl
Heat induction-sealed HDPE bottles without desiccant
Storage Conditions: 40° C./75% relative humidity

| Test | Time Points (months) | | |
|---|---|---|---|
| | 0 | 1 | 3 |
| QUALITY | | | |
| Appearance of capsule | White to off-white capsule | White to off-white capsule | White to off-white capsule |
| Appearance of capsule content | Light yellow powder | Light yellow powder | Light yellow power |
| POTENCY | | | |
| Assay by HPLC | 99.7% | 96.8% | 101.9% |
| PURITY Related Substances (HPLC) | | | |
| Biopterin | ND | 0.02% | 0.04% |
| Dihydrobiopterin | ND | 0.03% | 0.07% |
| R-Tetrahydrobiolumazine | 0.04% | 0.03% | 0.06% |
| S-Tetrahydrobiopterin | 0.03% | 0.02% | 0.04% |
| Tetrahydropterin | 0.03% | ND | 0.09% |
| Individual Unidentified | ND | 0.04% (RRT = 0.72) | ND |
| Total Unidentified | ND | 0.04% | ND |
| Total | 0.10% | 0.14% | 0.30% |

ND = Not Detected
RRT = Relative Retention Time

Example 6

Clinical Evaluation of BH4 Capsules

In designing a clinical evaluation of (6R)-L-erythro-tetrahydrobiopterin dihydrochloride, an important consideration is that BH4 is an essential co-factor for two enzymes primarily located in the central nervous system (CNS), tyrosine and tryptophan hydroxylases, and the dose of BH4 needed for normal neurotransmitter metabolism in the CNS is significantly higher than the dose needed to improve PAH activity in the liver.

The clinical evaluation comprises two clinical studies. In both studies, BH4 dihydrochloride is administered once daily to achieve higher peak concentrations and consequently improved CNS penetration.

A first study evaluates the relative bioavailability of BH4 dihydrochloride administered as a capsule in fasted conditions and after a meal in healthy subjects. Ascending doses of BH4 dihydrochloride up to 40 mg/kg/day are evaluated and drug levels in cerebrospinal fluid (CSF) are measured. Administration of higher doses up to 40 mg/kg/day as a single dose is expected to achieve higher peak levels of BH4 in CSF, provide availability of BH4 in CSF, and improve penetration of BH4 into the CNS. Measurement of BH4 levels in CSF is expected to be indicative of BH4 availability in brain tissues.

A second study evaluates the safety and efficacy of BH4 dihydrochloride in subjects with hyperphenylalaninemia due to BH4 deficiency. The subjects continue to receive the maximum dose of BH4 dihydrochloride tolerated in the first study for a total of 3 months. The primary endpoint for the second study is a measure of blood phenylalanine control. Moreover, other CSF parameters and neurological outcomes are evaluated. For example, serotonin and folate metabolism can be monitored by assessing 5-HIAA and 5-MTHF levels in the CSF. Further, because dopamine inhibits the secretion of prolactin and hyperprolactinemia has been documented in patients with BH4 deficiency, change in prolactin concentrations can function as a useful indicator of dopamine synthesis and content in the brain.

Example 7

Dry Process for Making Sachet Dosage Forms

The active ingredient, (6R)-L-erythro-tetrahydrobiopterin dihydrochloride or a BH4-related compound, and all the excipients were separately pre-screened through an appropriate size mesh (e.g., #20 mesh screen). A powder blend for sachets was prepared by adding one-half of the preweighed sweetener to a suitable blender (e.g., V-blender), adding the preweighed BH4 or a BH4-related compound to the blender, adding the preweighed flavor enhancer to the blender, and adding the remaining sweetener to the blender. The dry mixture was blended until the it was adequately mixed. A portion of the first mixture was then mixed with a preweighed amount of acesulfame potassium or sucralose, a flavoring agent, and ascorbic acid in a separate blender. The second mixture was passed through a suitable sieve (e.g., #20 mesh sieve) and then added to the remainder of the first mixture in the first blender and mixed until the blend was homogonous. The desired amount of the final powder blend was filled into sachets (e.g., single or double chamber sachets).

The sachets can be flushed with inert gas. The sachets can be hermetically sealed. The sachets can include a desiccant. The sachets may be further packaged in a Mylar pouch. The Mylar pouch may contain a desiccant.

Example 8

Sachet Dosage Forms

Certain embodiments of the sachet dosage forms of the present disclosure are illustrated in Tables 14, 16, and 17. The sapropterin dihydrochloride in all seven sachet examples in comparison Table 12 was in the form of polymorph B. Table 12 gives examples of formulations that comprise an amount of BH4 dihydrochloride of about 15% and between 75-80% mannitol, about 0-1% sucralose, about 1.5% flavoring agent, between 4.5-7% potassium citrate or potassium sodium tartrate, and about 1% ascorbic acid fine powder. In a specific embodiment, the flavoring agent is strawberry, orange on a sucrose substrate, orange on a mannitol substrate, or grape. In another specific embodiment, the blend also consists of about 5% potassium citrate.

Certain embodiments of the stability of the dosage forms from Table 12 are provided in Table 15. Table 15 presents stability data on compositions F, C1, and C2 from Table 12. Stability under different storage conditions were assessed and the potency of the active BH4 dihydrochloride is presented.

In an additional embodiment, the pharmaceutical formulation in the stable sachet dosage forms comprise an amount of BH4 dihydrochloride of about 15.1% BH4 dihydrochloride, 75.3% mannitol, 1.5% orange flavor on a sucrose base, 0.8% sucralose, 4.8% potassium citrate, and 0.8% ascorbic acid fine powder (Table 16).

TABLE 14

Examples of BH4 Dihydrochloride Dry blend Powder Formulations

| Ingredient | Percent (weight/weight) | | | | | | |
|---|---|---|---|---|---|---|---|
| | A | B | C1 | C2 | D | E | F |
| Sapropterin dihydrochloride | 15.6 | 15.1 | 15.3 | 15.3 | 15.1 | 15.1 | 15.1 |
| Mannitol | 77.9 | 35.0 | 76.7 | 76.7 | 75.2 | — | 75.2 |
| Sorbitol | — | — | — | — | — | 75.2 | — |
| Xylitol | — | 40.8 | — | — | — | — | — |
| Acesulfame potassium | — | 0.2 | — | — | — | — | — |
| Sucralose | 0.8 | — | 0.8 | 0.8 | 0.8 | 0.8 | 0.8 |
| Strawberry flavor | — | 1.5 | — | — | — | — | 1.5 |
| Orange flavor on sucrose substrate | — | — | 1.5 | — | — | — | — |
| Orange flavor on mannitol substrate | — | — | — | 1.5 | — | — | — |
| Grape flavor | — | — | — | — | 1.5 | 1.5 | — |
| Potassium Citrate | 4.9 | — | 4.9 | 4.9 | — | — | — |
| Potassium sodium tartrate | — | 6.6 | — | — | 6.6 | 6.6 | 6.6 |
| Ascorbic Acid Fine powder | 0.8 | 0.8 | 0.8 | 0.8 | 0.8 | 0.8 | 0.8 |
| | — | — | — | — | — | — | — |
| Total (g) | 100.0 | 100.0 | 100.0 | 100.0 | 100.0 | 100.0 | 100.0 |

In an additional embodiment, the pharmaceutical formulation in the stable sachet dosage forms comprise an amount of BH4 dihydrochloride of about 15.3% BH4 dihydrochloride, 76.7% mannitol, 1.5% orange flavor on a mannitol base, 0.8% sucralose, 4.8% potassium citrate, and 0.8% ascorbic acid fine powder (Table 16).

In another embodiment, the pharmaceutical formulation in the stable sachet dosage forms comprise a total amount of 0.835 g dry powder blend with the amount of BH4 dihydrochloride about 23.9% of the weight or 0.2 g (Table 17).

TABLE 15

Stability of BH4 Dihydrochloride Formulations

| Formulation | Potency (%) | Biopterin | BH2[a] | R-Tetrahydro-biolumazine | S-Tetrahydro-biolumazine | S-BH4[b] | BH4[b] | Individual unidentified | Total unidentified | Total Impurities (%) |
|---|---|---|---|---|---|---|---|---|---|---|
| Storage Condition: Initial time point | | | | | | | | | | |
| 100 μg/mL reference API | 100.6 | ND | 0.04 | 0.05 | ND[c] | 0.03 | 0.05 | ND | ND | 0.17 |
| F | 104.7 | 0.10 | 0.05 | 0.05 | ND | 0.04 | 0.05 | ND | ND | 0.29 |
| C1 | 101.9 | 0.01 | 0.03 | 0.05 | ND | 0.04 | 0.05 | ND | ND | 0.18 |
| C2 | 105.8 | 0.02 | 0.04 | 0.05 | ND | 0.04 | 0.06 | ND | ND | 0.21 |
| Storage Condition: 1 month at 25° C./60% RH | | | | | | | | | | |
| C1 | 94.8 | 0.02 | 0.04 | 0.04 | ND | 0.03 | 0.05 | ND | ND | 0.18 |
| C2 | 98.0 | 0.02 | 0.04 | 0.05 | ND | 0.04 | 0.05 | ND | ND | 0.20 |
| Storage Condition: 1 month at 40° C./75% RH | | | | | | | | | | |
| F | 97.2 | 0.20 | 0.06 | 0.37 | 0.01 | 0.03 | 0.04 | 0.01 0.05 | 0.01 | 0.77 |
| C1 | 91.8 | 0.029 | 0.132 | 0.038 | ND | ND | ND | 0.062 | 0.062 | 0.26 |
| C2 | 97.7 | 0.026 | 0.123 | 0.082 | ND | ND | ND | ND | ND | 0.23 |
| Storage Condition: 3 months at 40° C./75% RH | | | | | | | | | | |
| C1 | 48.48 | 0.106 | 0.162 | 0.093 | ND | 0.009 | 0.057 | 0.012 0.030 0.018 0.079 0.064 | 0.203 | 0.63 |
| C2 | 96.37 | 0.138 | 0.304 | 0.154 | 0.057 | 0.01 | 0.105 | 0.036 0.068 0.013 0.018 | 0.135 | 0.90 |

[a]BH2 = Dihydrobiopterin;
[b]BH4 = Tetrahydrobiopterin; and
[c]ND = Not Detected;

TABLE 16

Examples of BH4 Dihydrochloride Dry blend Powder Formulations

| Ingredient | Function | Example 1 % w/w | Example 2 % w/w |
|---|---|---|---|
| BH4 | Active | 15.1 | 15.3 |
| Mannitol | Sweetener | 75.3 | 76.7 |
| Orange Flavor (Sucrose base) | Flavor | 1.5 | — |
| Orange Flavor (Mannitol base) | Flavor | — | 1.5 |
| Sucralose | Sweetener | 0.8 | 0.8 |
| Potassium Citrate | Flavor Enhancer | 4.8 | 4.8 |
| Ascorbic Acid Fine | Flavor Enhancer | 0.8 | 0.8 |
| Total | | 100% | 100% |

TABLE 17

Examples of Sachet Dosage Formulations of BH4 Dihydrochloride

| | Formulation C | | Formulation D | | Formulation E | |
|---|---|---|---|---|---|---|
| Ingredient | g/sachet | % | g/sachet | % | g/sachet | % |
| Sapropterin HCl | 0.2000 | 23.95 | 0.2000 | 23.95 | 0.2000 | 23.95 |
| Mannitol | 0.3400 | 40.72 | 0.3381 | 40.49 | 0.3369 | 40.34 |
| Sucralose | 0.0100 | 1.20 | 0.0119 | 1.42 | 0.0131 | 1.57 |
| Potassium Citrate | 0.0650 | 7.78 | 0.0650 | 7.78 | 0.0650 | 7.78 |
| Ascorbic Acid | 0.0100 | 1.20 | 0.0100 | 1.20 | 0.0100 | 1.20 |
| Citric acid | 0.1500 | 17.96 | 0.1500 | 17.96 | 0.1500 | 17.96 |
| anhydrous Sodium citrate dihydrate | 0.0600 | 7.19 | 0.0600 | 7.19 | 0.0600 | 7.19 |
| Total | 0.8350 | 100.00 | 0.8350 | 100.00 | 0.8350 | 100.00 |

Example 9

Stability of Various Sachet Dosage Forms

Certain embodiments of the sachet dosage forms of the present disclosure are illustrated in Table 18, with a comparison of the stability of different BH4 or BH4-related compounds packaged in foil pouches.

TABLE 18

Stability of BH4 Dihydrochloride Sachet Packaged in Foil Pouches 40° C./75% RH

| | T = 1 Month | | T = 3 Month | |
|---|---|---|---|---|
| Sample | Lot 11434-50 Orange (Sucrose base) | Lot 11434-51 Orange (Mannitol base) | Lot 11434-50 Orange (Sucrose base) | Lot 11434-51 Orange (Mannitol base) |
| Biopterin (RRT = .5) % | 0.029 | 0.026 | 0.106 | 0.138 |
| BH2 (RRT = .6) % | 0.132 | 0.123 | 0.162 | 0.304 |
| R-THBL (RRT = .79) % | 0.038 | 0.082 | 0.093 | 0.154 |
| S-THBL (RRT = .88) % | ND | ND | ND | 0.057 |
| BH4% | 91.75 | 97.74 | 48.48 | 96.37 |
| S-BH4 (RRT = 1.2) % | ND | ND | 0.009 | 0.010 |
| THP (RRT = 1.4) % | ND | ND | 0.057 | 0.105 |
| Unknown Impurity (RRT = 1.4) % | ND | ND | 0.012 | 0.036 |
| Unknown Impurity (RRT = .54) % | ND | ND | 0.030 | 0.068 |
| Unknown Impurity (RRT = .58) % | ND | ND | 0.018 | 0.013 |
| Unknown Impurity (RRT = .72) % | 0.062 | ND | 0.079 | 0.018 |
| Unknown Impurity (RRT = .81) % | ND | ND | 0.064 | ND |
| Total Unknown Impurity | 0.062 | ND | 0.203 | 0.135 |
| Total Impurity | 0.261 | 0.231 | 0.629 | 0.903 |

ND = Not Detected

Example 10

Sachet Dosage Form Data without Flavoring

Certain embodiments of the sachet dosage forms of the present disclosure are illustrated in Table 19, wherein the sachet formulation may consist of a BH4 or BH4-related compound, a sweetener, and flavor enhancers without a flavoring agent.

It is understood that every embodiment described herein can optionally be combined with any one or more of the other embodiments described herein.

Every patent literature and every non-patent literature cited herein are incorporated herein by reference in their entirety.

TABLE 19

Sachet dosage formulation without flavoring agents

| Ingredient | g/sachet | % |
|---|---|---|
| Sapropterin HCl | 0.2 | 32 |
| Mannitol | 0.35 | 56 |
| Potassium Citrate | 0.065 | 10.4 |
| Ascorbic Acid | 0.01 | 1.6 |
| TOTAL | 0.625 | 100 |

Numerous modifications and variations to the disclosure, as set forth in the embodiments and illustrative examples described herein, are expected to occur to those skilled in the art. Consequently, only such limitations as appear in the accompanying claims should be placed on the disclosure.

Example 11

Sachet Dosage Form Containing 200 mg BH4 Dihydrochloride

Table 20 describes the formulation of a stable sachet dosage form comprising 200 mg (6R)-L-erythro-tetrahydrobiopterin dihydrochloride in polymorphic form B. This sachet dosage form was prepared in a manner as provided in the Detailed Description.

TABLE 20

Sachet dosage formulation containing 200 mg BH4 Dihydrochloride

| Ingredient | mg/sachet | % |
|---|---|---|
| Sapropterin 2HCl | 200 | 32 |
| Sucralose micronized | 11.9 | 1.9 |
| Potassium citrate monohydrate | 65 | 10.4 |
| Ascorbic acid fine powder | 10 | 1.6 |
| TOTAL | 625 | 100 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A pharmaceutical composition, comprising a dry blend powder that comprises about 32% by weight of (6R)-L-erythro-tetrahydrobiopterin dihydrochloride, about 54% by weight of mannitol, about 1.9% by weight of sucralose, about 10.4% by weight of potassium citrate, and about 1.6% by weight of ascorbic acid; wherein at least 90% of the initial amount of (6R)-L-erythro-tetrahydrobiopterin dihydrochloride in the pharmaceutical composition remains after the pharmaceutical composition is stored at 40° C. and 75% relative humidity for a period of three months.

2. The pharmaceutical composition of claim 1, wherein the initial amount of (6R)-L-erythro-tetrahydrobiopterin dihydrochloride in the pharmaceutical composition is in a range from about 100 mg to about 500 mg.

3. The pharmaceutical composition of claim 1, wherein the initial amount of (6R)-L-erythro-tetrahydrobiopterin dihydrochloride in the pharmaceutical composition is about 100 mg.

4. The pharmaceutical composition of claim 1, wherein the initial amount of (6R)-L-erythro-tetrahydrobiopterin dihydrochloride in the pharmaceutical composition is about 500 mg.

* * * * *